(12) United States Patent
Naldini et al.

(10) Patent No.: US 8,501,464 B2
(45) Date of Patent: Aug. 6, 2013

(54) LENTIVIRAL VECTORS CARRYING SYNTHETIC BI-DIRECTIONAL PROMOTERS AND USES THEREOF

(75) Inventors: Luigi Naldini, Milan (IT); Mario Amendola, Milan (IT); Elisa Vigna, Milan (IT)

(73) Assignee: Ospedale San Raffaele S.r.l., Milan (IT)

( * ) Notice: Subject to any disclaimer, the term of this patent is extended or adjusted under 35 U.S.C. 154(b) by 623 days.

(21) Appl. No.: 10/554,181

(22) PCT Filed: Apr. 21, 2004

(86) PCT No.: PCT/IT2004/000227
§ 371 (c)(1),
(2), (4) Date: Dec. 27, 2005

(87) PCT Pub. No.: WO2004/094642
PCT Pub. Date: Nov. 4, 2004

(65) Prior Publication Data
US 2006/0200869 A1    Sep. 7, 2006

Related U.S. Application Data

(60) Provisional application No. 60/465,080, filed on Apr. 24, 2003.

(51) Int. Cl.
| C12N 15/00 | (2006.01) |
| C12P 21/06 | (2006.01) |
| C12P 21/04 | (2006.01) |
| C12N 15/74 | (2006.01) |
| C12P 21/00 | (2006.01) |

(52) U.S. Cl.
USPC ..... 435/320.1; 435/69.1; 435/70.1; 435/71.1; 435/440; 435/455; 435/471; 435/325

(58) Field of Classification Search
None
See application file for complete search history.

(56) References Cited

U.S. PATENT DOCUMENTS

| 6,136,597 | A  | * | 10/2000 | Hope et al. | 435/325 |
| 6,780,639 | B1 | * | 8/2004 | Chtarto et al. | 435/320.1 |
| 6,995,011 | B2 | * | 2/2006 | Itoh et al. | 435/320.1 |

FOREIGN PATENT DOCUMENTS

| WO | WO9712622 | 4/1997 |
| WO | WO9930742 | 6/1999 |
| WO | WO9931261 | 6/1999 |
| WO | WO0029421 | 5/2000 |
| WO | WO0029557 | 5/2000 |
| WO | WO0066769 | 11/2000 |
| WO | WO0189580 | 11/2001 |
| WO | WO-03/087294 | 4/2003 |

OTHER PUBLICATIONS

Xie, et al., "Bidirectionalization of polar promoters in plants", Nature Biotechnology, vol. 19, pp. 677-679 (Jul. 2001).

Amendola, et al., "Coordinate dual-gene transgenesis by lentiviral vectors carrying synthetic bidirectional promoters", Nature Biotechnology, vol. 23, No. 1, pp. 108-116 (Jan. 2005).

(Continued)

*Primary Examiner* — Anne M. Gussow
*Assistant Examiner* — Nancy J Leith
(74) *Attorney, Agent, or Firm* — Lucas & Mercanti, LLP

(57) ABSTRACT

It is described a bidirectional promoter for expression of at least two coding sequences in opposite direction in animal cells; bidirectional expression cassettes; expression constructs; gene transfer expression vectors, and methods for the use thereof.

16 Claims, 26 Drawing Sheets

OTHER PUBLICATIONS

Figure 1:
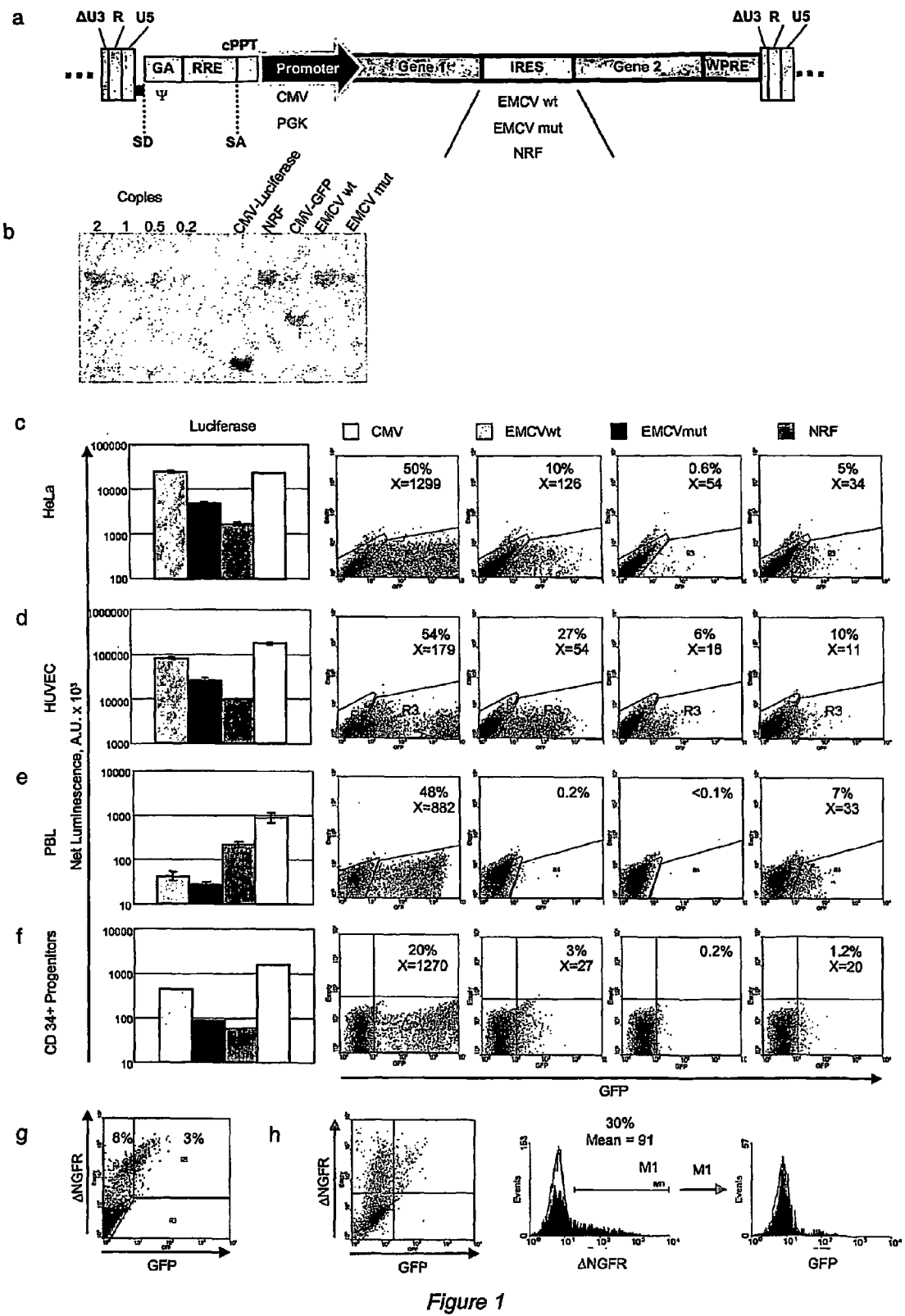

PCT International Search Report for Naldini, et al., Intl Application No. PCT/IT04/000227, Filed Apr. 21, 2004, Dated Oct. 12, 2004.

Yu, et al., "Lentiviral Vectors with Two Independent Internal Promoters Transfer High-Level Expression of Multiple Transgenes to Human Hematopoietic Stem-Progenitor Cells", Molecular Therapy, vol. 7, No. 6, pp. 827-838 (2003).

Fux, Cornelia and Fussenegger Martin "Bidirectional Expression Units Enable Streptogramin-Adjustable Gene Expression in Mammalian Cells", Biotechnology and Bioengineering, vol. 83, No. 5, pp. 618-625 (2003).

Fux, Cornelia and Fussenegger Martin "Toward Higher Order Control Modalities in Mammalian Cells-Independent Adjustment of Two Different Gene Activites", Biotechnolo. Prog, vol. 19, pp. 109-120 (2003).

Unsinger, et al., "Retroviral Vectors for the Transduction of Autoregulated Bidirectional Expression Cassettes", Molecular Therapy, vol. 4, No. 5, pp. 484-489 (2001).

Unsinger, et al., "Stable and strictly controlled expression of LTR-flanked autoregulated expression cassettes upon adenoviral transfer", Biochemical and Biophysical Research Communications, vol. 319, pp. 879-887 (2004)[.

* cited by examiner

Fig. 7b caggtggcacttttcggggaaatgtgcgcggaaccccctatttgtttattttctaaatacattcaaatatgtatccgctcatgaga
caataaccctgataaatgcttcaataatattgaaaaaggaagagtatgagtattcaacatttccgtgtcgcccttattcccttttt
gcggcattttgccttcctgttttgctcacccagaaacgctggtgaaagtaaaagatgctgaagatcagttgggtgcacgagt
gggttacatcgaactggatctcaacagcggtaagatccttgagagttttcgcccccgaagaacgttttccaatgatgagcacttt
taaagttctgctatgtggcgcggtattatcccgtattgacgccgggcaagagcaactcggtcgccgcatacactattctcaga
atgacttggttgagtactcaccagtcacagaaaagcatcttacggatggcatgacagtaagagaattatgcagtgctgccat
aaccatgagtgataacactgcggccaacttacttctgacaacgatcggaggaccgaaggagctaaccgcttttttgcacaac
atgggggatcatgtaactcgccttgatcgttgggaaccggagctgaatgaagccataccaaacgacgagcgtgacaccac
gatgcctgtagcaatggcaacaacgttgcgcaaactattaactggcgaactacttactctagcttcccggcaacaattaatag
actggatggaggcggataaagttgcaggaccacttctgcgctcggcccttccggctggctggtttattgctgataaatctgg
agccggtgagcgtgggtctcgcggtatcattgcagcactggggccagatggtaagccctcccgtatcgtagttatctacac
gacggggagtcaggcaactatggatgaacgaaatagacagatcgctgagataggtgcctcactgattaagcattggtaact
gtcagaccaagtttactcatatatactttagattgatttaaaacttcatttttaatttaaaaggatctaggtgaagatccttttgata
atctcatgaccaaaatcccttaacgtgagttttcgttccactgagcgtcagaccccgtagaaaagatcaaaggatcttcttgag
atcctttttttctgcgcgtaatctgctgcttgcaaacaaaaaaaccaccgctaccagcggtggtttgtttgccggatcaagagct
accaactctttttccgaaggtaactggcttcagcagagcgcagataccaaatactgtccttctagtgtagccgtagttaggcc
accacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcac
acagcccagcttggagcgaacgacctacaccgaactgagataccctacagcgtgagctatgagaaagcgccacgcttccc
gaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcagggggg
cggagcctatggaaaaacgccagcaacgcggcctttttacggttcctggccttttgctggccttttgctcacatgttcttcctg
cgttatcccctgattctgtggataaccgtattaccgcctttgagtgagctgataccgctcgccgcagccgaacgaccgagcg
cagcgagtcagtgagcgaggaagcggaagagcgcccaatacgcaaaccgcctctccccgcgcgttggccgattcattaa
tgcagctggcacgacaggtttcccgactggaaagcgggcagtgagcgcaacgcaattaatgtgagttagctcactcattag
gcaccccaggctttacactttatgcttccggctcgtatgttgtgtggaattgtgagcggataacaatttcacacaggaaacagc
tatgaccatgattacgccaagcgcgcaattaaccctcactaaagggaacaaaagctggagctgcaagcttaatgtagtctta
tgcaatactcttgtagtcttgcaacatggtaacgatgagttagcaacatgccttacaaggagagaaaaagcaccgtgcatgc
cgattggtggaagtaaggtggtacgatcgtgccttattaggaaggcaacagacgggtctgacatggattggacgaaccact
gaattgccgcattgcagagatattgtatttaagtgcctagctcgatacaataaacgggtctctctggttagaccagatctgagc
ctgggagctctctggctaactagggaacccactgcttaagcctcaataaagcttgccttgagtgcttcaagtagtgtgtgccc
gtctgttgtgtgactctggtaactagagatccctcagaccctttagtcagtgtggaaaatctctagcagtggcgcccgaaca
gggacctgaaagcgaaagggaaaccagagctctctcgacgcaggactcggcttgctgaagcgcgcacggcaagaggc
gaggggcggcgactggtgagtacgccaaaaattttgactagcggaggctagaaggagagagatgggtgcgagagcgtc
agtattaagcgggggagaattagatcgcgatgggaaaaaattcggttaaggccaggggggaaagaaaaaatataaattaaa
acatatagtatgggcaagcagggagctagaacgattcgcagttaatcctggcctgttagaaacatcagaaggctgtagaca
aatactgggacagctacaaccatcccttcagacaggatcagaagaacttagatcattatataatacagtagcaaccctctatt
gtgtgcatcaaaggatagagataaaagacaccaaggaagcttagacaagatagaggaagagcaaaacaaaagtaagac
caccgcacagcaagcggccgctgatcttcagacctggaggaggagatatgagggacaattggagaagtgaattatataaa
tataaagtagtaaaattgaaccattaggagtagcacccaccaaggcaaagagaagagtggtgcagagagaaaaaagag
cagtgggaataggagctttgttccttgggttcttgggagcagcaggaagcactatgggcgcagcctcaatgacgctgacgg
tacaggccagacaattattgtctggtatagtgcagcagcagaacaatttgctgagggctattgaggcgcaacagcatctgtt
gcaactcacagtctggggcatcaagcagctccaggcaagaatcctggctgtggaaagatacctaaaggatcaacagctcc
tggggatttggggttgctctggaaaactcatttgcaccactgctgtgccttggaatgctagttggagtaataaatctctggaac
agatttggaatcacacgacctggatggagtgggacagagaaattaacaattacacaagcttaatacactccttaattgaaga
atcgcaaaaccagcaagaaaagaatgaacaagaattattggaattagataaatgggcaagtttgtggaattggtttaacataa
caaattggctgtggtatataaaattattcataatgatagtaggaggcttggtaggtttaagaatagttttgctgtactttctatagt
gaatagagttaggcagggatattcaccattatcgtttcagacccacctcccaaccccgaggggacccgacaggcccgaag Fig. 7b (continued)

gaatagaagaagaaggtggagagagagagacagagacagatccatcgattagtgaacggatctcgacggtatcggttaact
tttaaaagaaaagggggggattggggggtacagtgcaggggaaagaatagtagacataatagcaacagacatacaaacta
aagaattacaaaaacaaattacaaaaattcaaaattttatcgatcacgagactagcctcgagagatctgatcataatcagccat
accacatttgtagaggttttacttgctttaaaaaacctcccacacctcccctgaacctgaaacataaaatgaatgcaattgttg
ttgttaacttgtttattgcagcttataatggttacaaataaggcaatagcatcacaaatttcacaaataaggcattttttcactgca
ttctagttttggtttgtccaaactcatcaatgtatcttatcatgtctggatctcaaatccctcggaagctgcgcctgtcttaggttgg
agtgatacattttatcacttttacccgtctttggattaggcagtagctctgacggccctcctgtcttaggttagtgaaaaatgtca
ctctcttacccgtcattggctgtccagcttagctcgcaggggaggtggtctggatcctctagaattacacggcgatctttccgc
ccttcttggcctttatgaggatctctctgattttcttgcgtcgagttttccggtaagacctttcggtacttcgtccacaaacacaa
ctcctccgcgcaacttttcgcggttgttacttgactggccacgtaatccacgatctcttttccgtcatcgtctttccgtgctcca
aaacaacaacggcggcgggaagttcaccggcgtcatcgtcgggaagacctgcgacacctgcgtcgaagatgttggggt
gttggagcaagatggattccaattcagcgggagccacctgatagcctttgtacttaatcagagacttcaggcggtcaacgat
gaagaagtgttcgtcttcgtcccagtaagctatgtctccagaatgtagccatccatccttgtcaatcaaggcgttggtcgcttc
cggattgtttacataaccggacataatcataggacctctcacacacagttcgcctctttgattaacgcccagcgttttcccggta
tccagatccacaaccttcgcttcaaaaaatggaacaactttaccgaccgcgcccggttatcatcccctcgggtgtaatcag
aatagctgatgtagtctcagtgagcccatatccttgcctgatacctggcagatggaacctcttggcaaccgcttcccgactt
ccttagagaggggagcgccaccagaagcaatttcgtgtaaattagataaatcgtatttgtcaatcagagtgcttttggcgaag
aaggagaatagggttggcaccagcagcgcactttgaatcttgtaatcctgaaggctcctcagaaacagctcttcttcaaatct
atacattaagacgactcgaaatccacatatcaaatatccgagtgtagtaaacattccaaaaccgtgatggaatggaacaaca
cttaaaatcgcagtatccggaatgatttgattgccaaaaataggatctctggcatgcgagaatctcacgcaggcagttctatg
aggcagagcgacacctttaggcagaccagtagatccagaggagttcatgatcagtgcaattgtcttgtccctatcgaagga
ctctggcacaaaatcgtattcattaaaaccgggaggtagatgagatgtgacgaacgtgtacatcgactgaaatccctggtaa
tccgttttagaatccatgataataattttttggatgattgggagcttttttgcacgttcaaaatttttgcaaccccttttggaaacg
aacaccacggtaggctgcgaaatgcccatactgttgagcaattcacgttcattataaatgtcgttcgcgggcgcaactgcaa
ctccgataaataacgcgcccaacaccggcataaagaattgaagagagttttcactgcatacgacgattctgtgatttgtattca
gcccatatcgtttcatagcttctgccaaccgaacggacatttcgaagtactcagcgtaagtgatgtccacctcgatatgtgcat
ctgtaaaagcaattgttccaggaaccagggcgtatctcttcatagccttatgcagttgctctccagcggttccatcttccagcg
gatagaatggcgccgggcctttctttatgtttttggcgtcttccatggtgaattccgcggaggctggatcggtcccggtgtcttc
tatggaggtcaaaacagcgtggatggcgtctccaggcgatctgacggttcactaaacgagctctgcttatataggcctccca
ccgtacacgcctaccctcgagaagcttgatatcgaattcccacggggttgggttgcgccttttccaaggcagccctgggtt
tgcgcagggacgcggctgctctgggcgtggttccgggaaacgcagcggcgccgaccctgggtctcgcacattcttcacg
tccgttcgcagcgtcacccggatcttcgccgctaccttgtgggcccccggcgacgcttcctgctccgccctaagtcgg
gaaggttccttgcggttcgcggcgtgccggacgtgacaaacggaagccgcacgtctcactagtaccctcgcagacggac
agcgccaggagcaatggcagcgcgccgaccgcgatgggctgtggccaatagcggctgctcagcggggcgcgccga
gagcagcggccgggaaggggcggtgcgggagcggggtgtggggcggtagtgtgggccctgttcctgcccgcgcgg
tgttccgcattctgcaagcctccggagcgcacgtcggcagtcggctccctcgttgaccgaatcaccgacctctctcccag
ggggatccaccggtcgccaccatggtgagcaaggcgaggagctgttcaccggggtggtgcccatcctggtcgagctg
gacggcgacgtaaacggccacaagttcagcgtgtccggcgagggcgagggcgatgccacctacggcaagctgaccct
gaagttcatctgcaccaccggcaagctgcccgtgccctggcccacactcgtgaccaccctgacctacggcgtgcagtgctt
cagccgctaccccgaccacatgaagcagcacgacttcttcaagtccgccatgcccgaaggctacgtccaggagcgcacc
atcttcttcaaggacgacggcaactacaagacccgcgccgaggtgaagttcgagggcgacaccctggtgaaccgcatcg
agctgaagggcatcgacttcaaggaggacggcaacatcctggggcacaagctggagtacaactacaacagccacaacg
tctatatcatggccgacaagcagaagaacggcatcaaggtgaacttcaagatccgccacaacatcgaggacggcagcgt
gcagctcgccgaccactaccagcagaacacccccatcggcgacggccccgtgctgctgcccgacaaccactacctgag
cacccagtccgccctgagcaaagaccccaacgagaagcgcgatcacatggtcctgctggagttcgtgaccgccgccgg
gatcactctcggcatggacgagctgtacaagtaaagcggccgcgtcgacaatcaacctctggattacaaaatttgtgaaag
attgactggtattcttaactatgttgctccttttacgctatgtggatacgctgctttaatgcctttgtatcatgctattgcttcccgtat
ggctttcattttctcctccttgtataaatcctggttgctgtctctttatgaggagttgtggcccgttgtcaggcaacgtggcgtggt Fig. 7b (continued)

gtgcactgtgtttgctgacgcaacccccactggttggggcattgccaccacctgtcagctcctttccgggactttcgctttccc
cctccctattgccacggcggaactcatcgccgcctgccttgcccgctgctggacagggggctcggctgttgggcactgaca
attccgtggtgttgtcggggaagctgacgtcctttccatggctgctcgcctgtgttgccacctggattctgcgcgggacgtcc
ttctgctacgtcccttcggccctcaatccagcggaccttccttcccgcggcctgctgccggctctgcggcctcttccgcgtctt
cgccttcgccctcagacgagtcggatctccctttgggccgcctccccgcctggaattcgagctcggtacctttaagaccaat
gacttacaaggcagctgtagatcttagccactttttaaaagaaaaggggggactggaagggctaattcactcccaacgaag
acaagatctgcttttgcttgtactgggtctctctggttagaccagatctgagcctgggagctctctggctaactagggaaccc
actgcttaagcctcaataaagcttgccttgagtgcttcaagtagtgtgtgcccgtctgttgtgtgactctggtaactagagatcc
ctcagacccttttagtcagtgtggaaaatctctagcagtagtagttcatgtcatcttattattcagtatttataacttgcaaagaaat
gaatatcagagagtgagaggaacttgtttattgcagcttataatggttacaaataaagcaatagcatcacaaatttcacaaata
aagcatttttttcactgcattctagttgtggtttgtccaaactcatcaatgtatcttatcatgtctggctctagctatcccgcccctaa
ctccgcccagttccgcccattctccgcccatggctgactaatttttttatttatgcagaggccgaggccgcctcggcctctg
agctattccagaagtagtgaggaggcttttttggaggcctaggcttttgcgtcgagacgtacccaattcgccctatagtgagt
cgtattacgcgcgctcactggccgtcgttttacaacgtcgtgactgggaaaaccctggcgttacccaacttaatcgccttgca
gcacatccccctttcgccagctggcgtaatagcgaagaggcccgcaccgatcgcccttcccaacagttgcgcagcctgaa
tggcgaatggcgcgacgcgccctgtagcggcgcattaagcgcggcgggtgtggtggttacgcgcagcgtgaccgctac
acttgccagcgccctagcgcccgctcctttcgctttcttcccttcctttctcgccacgttcgccggctttccccgtcaagctcta
aatcgggggctccctttagggttccgatttagtgctttacggcacctcgaccccaaaaaacttgattagggtgatggttcacgt
agtgggccatcgccctgatagacggtttttcgccctttgacgttggagtccacgttctttaatagtggactcttgttccaaactg
gaacaacactcaacccctatctcggtctattcttttgatttataagggattttgccgatttcggcctattggttaaaaaatgagctga
tttaacaaaaatttaacgcgaattttaacaaaatattaacgtttacaatttcc

Fig. 8b caggtggcacttttcggggaaatgtgcgcggaaccccctatttgtttattttttctaaatacattcaaatatgtatccgctcatgaga
caataaccctgataaatgcttcaataatatattgaaaaaggaagagtatgagtattcaacatttccgtgtcgcccttattcccttttt
gcggcattttgccttcctgttttgctcacccagaaacgctggtgaaagtaaaagatgctgaagatcagttgggtgcacgagt
gggttacatcgaactggatctcaacagcggtaagatccttgagagttttcgccccgaagaacgttttccaatgatgagcacttt
taaagttctgctatgtggcgcggtattatcccgtattgacgccgggcaagagcaactcggtcgccgcatacactattctcaga
atgacttggttgagtactcaccagtcacagaaaagcatcttacggatggcatgacagtaagagaattatgcagtgctgccat
aaccatgagtgataacactgcggccaacttacttctgacaacgatcggaggaccgaaggagctaaccgcttttttgcacaac
atgggggatcatgtaactcgccttgatcgttgggaaccggagctgaatgaagccataccaaacgacgagcgtgacaccac
gatgcctgtagcaatggcaacaacgttgcgcaaactattaactggcgaactacttactctagcttcccggcaacaattaatag
actggatggaggcggataaagttgcaggaccacttctgcgctcggcccttccggctggctggtttattgctgataaatctgg
agccggtgagcgtgggtctcgcggtatcattgcagcactggggccagatggtaagccctcccgtatcgtagttatctacac
gacggggagtcaggcaactatggatgaacgaaatagacagatcgctgagataggtgcctcactgattaagcattggtaact
gtcagaccaagtttactcatatatactttagattgatttaaaacttcattttttaatttaaaaggatctaggtgaagatccttttttgata
atctcatgaccaaaatcccttaacgtgagttttcgttccactgagcgtcagaccccgtagaaaagatcaaaggatcttcttgag
atcctttttttctgcgcgtaatctgctgcttgcaaacaaaaaaaccaccgctaccagcggtggtttgtttgccggatcaagagct
accaactctttttccgaaggtaactggcttcagcagagcgcagataccaaatactgtccttctagtgtagccgtagttaggcc
accacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcac
acagcccagcttggagcgaacgacctacaccgaactgagatacctacagcgtgagctatgagaaagcgccacgcttccc
gaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctg
cgttatcccctgattctgtggataaccgtattaccgcctttgagtgagctgataccgctcgccgcagccgaacgaccgagcg
cagcgagtcagtgagcgaggaagcggaagagcgcccaatacgcaaaccgcctctccccgcgcgttggccgattcattaa
tgcagctggcacgacaggtttcccgactggaaagcgggcagtgagcgcaacgcaattaatgtgagttagctcactcattag
gcaccccaggctttacactttatgcttccggctcgtatgttgtgtggaattgtgagcggataacaatttcacacaggaaacagc
tatgaccatgattacgccaagcgcgcaattaaccctcactaaagggaacaaaagctggagctgcaagcttggccattgcat
acgttgtatccatatcataatatgtacatttatattggctcatgtccaacattaccgccatgttgacattgattattgactagttatta
atagtaatcaattacggggtcattagttcatagcccatatatggagttccgcgttacataacttacggtaaatggcccgcctgg
ctgaccgcccaacgacccccgcccattgacgtcaataatgacgtatgttcccatagtaacgccaatagggactttccattga
cgtcaatgggtggagtatttacggtaaactgcccacttggcagtacatcaagtgtatcatatgccaagtacgccccctattga
cgtcaatgacggtaaatggcccgcctggcattatgcccagtacatgaccttatgggactttcctacttggcagtacatctacgt
attagtcatcgctattaccatggtgatgcggttttggcagtacatcaatgggcgtggatagcggtttgactcacggggatttcc
aagtctccaccccattgacgtcaatgggagtttgttttggcaccaaaatcaacgggactttccaaaatgtcgtaacaactccg
ccccattgacgcaaatgggcggtaggcgtgtacggtgggaggtctatataagcagagctcgtttagtgaaccggggtctct
ctggttagaccagatctgagcctgggagctctctggctaactagggaacccactgcttaagcctcaataaagcttgccttga
gtgcttcaagtagtgtgtgcccgtctgttgtgtgactctggtaactagagatccctcagacccttttagtcagtgtggaaaatct
ctagcagtggcgcccgaacagggacctgaaagcgaaagggaaaccagagctctctcgacgcaggactcggcttgctga
agcgcgcacggcaagaggcgaggggcggcgactggtgagtacgccaaaaattttgactagcggaggctagaaggaga
gagatgggtgcgagagcgtcagtattaagcgggggagaattagatcgcgatgggaaaaaattcggttaagccagggggg
aaagaaaaaatataaattaaaacatatagtatgggcaagcagggagctagaacgattcgcagttaatcctggcctgttagaa
acatcagaaggctgtagacaaatactgggacagctacaaccatcccttcagacaggatcagaagaacttagatcattatata
atacagtagcaaccctctattgtgtgcatcaaaggatagagataaaagacaccaaggaagctttagacaagatagaggaag
agcaaaacaaaagtaagaccaccgcacagcaagcggccgctgatcttcagacctggaggaggagatatgagggacaat
tggagaagtgaattatataaatataaagtagtaaaaattgaaccattaggagtagcacccaccaaggcaaagagaagagtg
gtgcagagagaaaaaagagcagtgggaataggagctttgttccttgggttcttgggagcagcaggaagcactatgggcgc
agcctcaatgacgctgacggtacaggccagacaattattgtctggtatagtgcagcagcagaacaatttgctgagggctatt Fig. 8b (continued)

gaggcgcaacagcatctgttgcaactcacagtctggggcatcaagcagctccaggcaagaatcctggctgtggaaagata
cctaaaggatcaacagctcctggggatttggggttgctctggaaaactcatttgcaccactgctgtgccttggaatgctagttg
gagtaataaatctctggaacagattggaatcacacgacctggatggagtgggacagagaaattaacaattacacaagctta
atacactccttaattgaagaatcgcaaaaccagcaagaaaagaatgaacaagaattattggaattagataaatgggcaagttt
gtggaattggttaacataacaaattggctgtggtatataaaattattcataatgatagtaggaggcttggtaggtttaagaatag
ttttgctgtactttctatagtgaatagagttaggcagggatattcaccattatcgtttcagacccacctcccaaccccgagggg
acccgacaggcccgaaggaatagaagaagaaggtggagagagagacagagacagatccattcgattagtgaacggatc
tcgacggtatcggttaacttttaaaagaaaaggggggattgggggggtacagtgcaggggaaagaatagtagacataatag
caacagacatacaaactaaagaattacaaaaacaaattacaaaaattcaaaattttatcgatcacgagactagcctcgagag
atctgatcataatcagccataccacatttgtagaggttttacttgctttaaaaaacctcccacacctcccctgaacctgaaaca
taaaatgaatgcaattgttgttgttaacttgtttattgcagcttataatggttacaaataaggcaatagcatcacaaatttcacaaa
taaggcattttttcactgcattctagttttggtttgtccaaactcatcaatgtatcttatcatgtctggatctcaaatccctcggaag
ctgcgcctgtcttaggttggagtgatacattttatcactttaccgtctttggattaggcagtagctctgacggccctcctgtct
taggttagtgaaaaatgtcactctcttacccgtcattggctgtccagcttagctcgcaggggaggtggtctggatccgagctc
gaattggccgctttacttgtacagctcgtccatgccgagagtgatcccggcggcggtcacgaactccagcaggaccatgtg
atcgcgcttctcgttggggtctttgctcagggcggactgggtgctcaggtagtggttgtcgggcagcagcacggggccgtc
gccgatgggggtgttctgctggtagtggtcggcgagctgcacgctgccgtcctcgatgttgtggcggatcttgaagttcacc
ttgatgccgttcttctgcttgtcggccatgatatagacgttgtggctgttgtagttgtactccagcttgtgcccaggatgttgcc
gtcctccttgaagtcgatgcccttcagctcgatgcggttcaccagggtgtcgccctcgaacttcacctcggcgcgggtcttgt
agttgccgtcgtccttgaagaagatggtgcgctcctggacgtagccttcgggcatggcggacttgaagaagtcgtgctgctt
catgtggtcggggtagcggctgaagcactgcacgccgtaggtcagggtggtcacgagggtgggccagggcacgggca
gcttgccggtggtgcagatgaacttcagggtcagcttgccgtaggtggcatcgccctcgccctcgccggacacgctgaact
tgtggccgtttacgtcgccgtccagctcgaccaggatgggcaccaccccggtgaacagctcctcgcccttgctcaccatgg
tgaattccgcggaggctggatcggtcccggtgtcttctatggaggtcaaaacagcgtggatggcgtctccaggcgatctga
cggttcactaaacgagctctgcttatataggcctcccaccgtacacgcctaccctgagaagcttgatatcgaattcccacgg
ggttggggttgcgccttttccaaggcagccctgggtttgcgcagggacgcggctgctctgggcgtggttccgggaaacgc
agcggcgccgaccctgggtctcgcacattcttcacgtccgttcgcagcgtcacccggatcttcgccgctaccctgtgggc
cccccggcgacgcttcctgctccgccccctaagtcgggaaggttccttgcggttcgcggcgtgccggacgtgacaaacgg
aagccgcacgtctcactagtaccctcgcagacggacagcgccagggagcaatggcagcgcgccgaccgcgatgggct
gtggccaatagcggctgctcagcggggcgcgccgagagcagcggccgggaaggggcggtgcgggaggcggggtgt
ggggcggtagtgtggccctgttcctgcccgcgcggtgttccgcattctgcaagcctccggagcgcacgtcggcagtcgg
ctccctcgttgaccgaatcaccgacctctctccccagggggatcccccgggctgcaggaattcgggccgcggccagctcc
ggcgggcagggggggcgctggagcgcagcgcagcgcagcccatcagtccgcaaagcggaccgagctggaagtcg
agcgctgccgcggggaggcgggcgatggggcaggtgccaccggccgcgccatggacgggccgcgcctgctgctgtt
gctgcttctgggggtgtcccttggaggtgccaaggaggcatgcccacaggcctgtacacacacagcggtgagtgctgca
aagcctgcaacctgggcgagggtgtggcccagccttgtggagccaaccagaccgtgtgtgagccctgcctggacagcgt
gacgttctccgacgtggtgagcgcgaccgagccgtgcaagccgtgcaccgagtgcgtggggctccagagcatgtcggc
gccgtgcgtggaggccgacgacgccgtgtgccgctgcgcctacggctactaccaggatgagacgactgggcgctgcga
ggcgtgccgcgtgtgcgaggcgggctcgggcctcgtgttctcctgccaggacaagcagaacaccgtgtgcgaggagtg
ccccgacggcacgtattccgacgaggccaaccacgtggacccgtgcctgccctgcaccgtgtgcgaggacaccgagcg
ccagctccgcgagtgcacacgctgggccgacgccgagtgcgaggagatccctggccgttggattacacggtccacacc
cccagagggctcggacagcacagcccccagcacccaggagcctgaggcacctccagaacaagacctcatagccagca
cggtggcaggtgtggtgaccacagtgatgggcagctcccagcccgtggtgacccgaggcaccacgacaacctcatcc
ctgtctattgctccatcctggctgctgtggttgtgggccttgtggcctacatagccttcaagaggtggaacagggggatcctct
agagtcgagtctagagtcgacaatcaacctctggattacaaaatttgtgaaagattgactggtattcttaactatgttgctcctttt
acgctatgtggatacgctgctttaatgcctttgtatcatgctattgcttcccgtatggctttcattttctcctccttgtataaatcctg
gttgctgtctctttatgaggagttgtggcccgttgtcaggcaacgtggcgtggtgtgcactgtgtttgctgacgcaacccca
ctggttggggcattgccaccacctgtcagctcctttccgggactttcgctttcccccctccctattgccacggcggaactcatcg Fig. 8b (continued)

ccgcctgccttgcccgctgctggacaggggctcggctgttgggcactgacaattccgtggtgttgtcggggaagctgacgt
cctttccatggctgctcgcctgtgttgccacctggattctgcgcgggacgtccttctgctacgtcccttcggccctcaatccag
cggaccttccttcccgcggcctgctgccggctctgcggcctcttccgcgtcttcgccttcgccctcagacgagtcggatctc
cctttgggccgcctccccgcctggaattcgagctcggtacctttaagaccaatgacttacaaggcagctgtagatcttagcca
cttttaaaagaaaaggggggactggaagggctaattcactcccaacgaagacaagatctgcttttgcttgtactgggtctct
ctggttagaccagatctgagcctgggagctctctggctaactagggaacccactgcttaagcctcaataaagcttgccttga
gtgcttcaagtagtgtgtgcccgtctgttgtgtgactctggtaactagagatccctcagacccttttagtcagtgtggaaaatct
ctagcagtagtagttcatgtcatcttattattcagtatttataacttgcaaagaaatgaatatcagagagtgagaggaacttgttta
ttgcagcttataatggttacaaataaagcaatagcatcacaaatttcacaaataaagcattttttcactgcattctagttgtggttt
gtccaaactcatcaatgtatcttatcatgtctggctctagctatcccgcccctaactccgcccagttccgcccattctccgcccc
atggctgactaattttttttatttatgcagaggccgaggccgcctcggcctctgagctattccagaagtagtgaggaggcttttt
tggaggcctaggcttttgcgtcgagacgtacccaattcgccctatagtgagtcgtattacgcgcgctcactggccgtcgtttta
caacgtcgtgactgggaaaaccctggcgttacccaacttaatcgccttgcagcacatccccctttcgccagctggcgtaata
gcgaagaggcccgcaccgatcgcccttcccaacagttgcgcagcctgaatggcgaatggcgcgacgcgcctgtagcg
gcgcattaagcgcggcgggtgtggtggttacgcgcagcgtgaccgctacacttgccagcgccctagcgcccgctccttc
gctttcttcccttcctttctcgccacgttcgccggctttccccgtcaagctctaaatcgggggctcccctttagggttccgatttag
tgctttacggcacctcgaccccaaaaaacttgattagggtgatggttcacgtagtgggccatcgccctgatagacggttttc
gccctttgacgttggagtccacgttctttaatagtggactcttgttccaaactggaacaacactcaacccctatctcggtctattct
tttgatttataagggattttgccgatttcggcctattggttaaaaaatgagctgatttaacaaaaatttaacgcgaattttaacaaa
atattaacgtttacaatttcc

Fig. 9b caggtggcacttttcggggaaatgtgcgcggaaccccctatttgtttattttctaaatacattcaaatatgtatccgctcatgaga
caataaccctgataaatgcttcaataatattgaaaaaggaagagtatgagtattcaacatttccgtgtcgcccttattccctttttt
gcggcattttgccttcctgttttgctcacccagaaacgctggtgaaagtaaaagatgctgaagatcagttgggtgcacgagt
gggttacatcgaactggatctcaacagcggtaagatccttgagagttttcgccccgaagaacgttttccaatgatgagcacttt
taaagttctgctatgtggcgcggtattatcccgtattgacgccgggcaagagcaactcggtcgccgcatacactattctcaga
atgacttggttgagtactcaccagtcacagaaaagcatcttacggatggcatgacagtaagagaattatgcagtgctgccat
aaccatgagtgataacactgcggccaacttacttctgacaacgatcggaggaccgaaggagctaaccgcttttttgcacaac
atgggggatcatgtaactcgccttgatcgttgggaaccggagctgaatgaagccataccaaacgacgagcgtgacaccac
gatgcctgtagcaatggcaacaacgttgcgcaaactattaactggcgaactacttactctagcttcccggcaacaattaatag
actggatggaggcggataaagttgcaggaccacttctgcgctcggcccttccggctggctggtttattgctgataaatctgg
agccggtgagcgtgggtctcgcggtatcattgcagcactggggccagatggtaagccctcccgtatcgtagttatctacac
gacggggagtcaggcaactatggatgaacgaaatagacagatcgctgagataggtgcctcactgattaagcattggtaact
gtcagaccaagttactcatatatactttagattgatttaaaacttcattttaattttaaaaggatctaggtgaagatccttttgata
atctcatgaccaaaatcccttaacgtgagttttcgttccactgagcgtcagaccccgtagaaaagatcaaaggatcttcttgag
atccttttttttctgcgcgtaatctgctgcttgcaaacaaaaaaaccaccgctaccagcggtggtttgtttgccggatcaagagct
accaactcttttccgaaggtaactggcttcagcagagcgcagataccaaatactgtccttctagtgtagccgtagttaggcc
accacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcac
acagcccagcttggagcgaacgacctacaccgaactgagatacctacagcgtgagctatgagaaagcgccacgcttccc
gaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcagggggg
cggagcctatggaaaaacgccagcaacgcggcctttttacggttcctggccttttgctggccttttgctcacatgttctttcctg
cgttatcccctgattctgtggataaccgtattaccgcctttgagtgagctgataccgctcgccgcagccgaacgaccgagcg
cagcgagtcagtgagcgaggaagcggaagagcgcccaatacgcaaaccgcctctccccgcgcgttggccgattcattaa
tgcagctggcacgacaggtttcccgactggaaagcgggcagtgagcgcaacgcaattaatgtgagttagctcactcattag
gcaccccaggctttacactttatgcttccggctcgtatgttgtgtggaattgtgagcggataacaatttcacacaggaaacagc
tatgaccatgattacgccaagcgcgcaattaaccctcactaaagggaacaaaagctggagctgcaagcttaatgtagtctta
tgcaatactcttgtagtcttgcaacatggtaacgatgagttagcaacatgccttacaaggagagaaaaagcaccgtgcatgc
cgattggtggaagtaaggtggtacgatcgtgccttattaggaaggcaacagacgggtctgacatggattggacgaaccact
gaattgccgcattgcagagatattgtatttaagtgcctagctcgatacaataaacgggtctctctggttagaccagatctgagc
ctgggagctctctggctaactagggaacccactgcttaagcctcaataaagcttgccttgagtgcttcaagtagtgtgtgccc
gtctgttgtgtgactctggtaactagagatccctcagaccctttagtcagtgtggaaaatctctagcagtggcgcccgaaca
gggacctgaaagcgaaagggaaaccagagctctctcgacgcaggactcggcttgctgaagcgcgcacggcaagaggc
gaggggcggcgactggtgagtacgccaaaaattttgactagcggaggctagaaggagagagatgggtgcgagagcgtc
agtattaagcggggggagaattagatcgcgatgggaaaaaattcggttaaggccagggggaaagaaaaaatataaattaaa
acatatagtatgggcaagcagggagctagaacgattcgcagttaatcctggcctgttagaaacatcagaaggctgtagaca
aatactgggacagctacaaccatcccttcagacaggatcagaagaacttagatcattatataatacagtagcaaccctctatt
gtgtgcatcaaaggatagagataaaagacaccaaggaagctttagacaagatagaggaagagcaaaacaaaagtaagac
caccgcacagcaagcggccgctgatcttcagacctggaggaggagatatgagggacaattggagaagtgaattatataaa
tataaagtagtaaaattgaaccattaggagtagcacccaccaaggcaaagagaagagtggtgcagagagaaaaaagag
cagtgggaataggagctttgttccttgggttcttgggagcagcaggaagcactatgggcgcagcctcaatgacgctgacgg
tacaggccagacaattattgtctggtatagtgcagcagcagaacaatttgctgagggctattgaggcgcaacagcatctgtt
gcaactcacagtctggggcatcaagcagctccaggcaagaatcctggctgtggaaagatacctaaaggatcaacagctcc
tggggatttggggttgctctggaaaactcatttgcaccactgctgtgccttggaatgctagttggagtaataaatctctggaac
agattggaatcacacgacctggatggagtgggacagagaaattaacaattcacaagcttaatacactccttaattgaagaa
tcgcaaaaccagcaagaaaagaatgaacaagaattattggaattagataaatgggcaagtttgtggaattggtttaacataac
aaaattggctgtggtatataaaattattcataatgatagtaggaggcttggtaggtttaagaatagttttgctgtactttctatagtg
aatagagttaggcagggatattcaccattatcgtttcagacccacctcccaaccccgaggggacccgacaggcccgaagg Fig. 9b (continued)

aatagaagaagaaggtggagagagagacagagacagatccattcgattagtgaacggatctcgacggtatcggttaactttt
taaaagaaaagggggggattgggggggtacagtgcaggggaaagaatagtagacataatagcaacagacatacaaactaaa
gaattacaaaaacaaattacaaaaattcaaaattttatcgatcacgagactagcctcgagagatctgatcataatcagccatac
cacatttgtagaggttttacttgctttaaaaaacctcccacacctcccccctgaacctgaaacataaaatgaatgcaattgttgttg
ttaacttgtttattgcagcttataatggttacaaataaggcaatagcatcacaaatttcacaaataaggcatttttttcactgcattc
tagttttggtttgtccaaactcatcaatgtatcttatcatgtctggatctcaaatccctcggaagctgcgcctgtcttaggttggag
tgatacatttttatcacttttacccgtctttggattaggcagtagctctgacggccctcctgtcttaggttagtgaaaaatgtcact
ctcttacccgtcattggctgtccagcttagctcgcaggggaggtggtctggatccctggatatcaagaattcgtcctcgagct
cagatcctctagaattacacggcgatctttccgcccttcttggcctttatgaggatctctctgattttcttgcgtcgagttttccgg
taagaccttttcggtacttcgtccacaaacacaactcctccgcgcaacttttttcgcggttgttacttgactggccacgtaatccac
gatctcttttccgtcatcgtctttccgtgctccaaaacaacaacggcggcgggaagttcaccggcgtcatcgtcgggaaga
cctgcgacacctgcgtcgaagatgttggggtgttggagcaagatggattccaattcagcgggagccacctgatagcctttgt
acttaatcagagacttcaggcggtcaacgatgaagaagtgttcgtcttcgtcccagtaagctatgtctccagaatgtagccat
ccatccttgtcaatcaaggcgttggtcgcttccggattgtttacataaccggacataatcataggacctctcacacacagttcg
cctctttgattaacgcccagcgttttcccggtatccagatccacaaccttcgcttcaaaaaatggaacaactttaccgaccgcg
cccggtttatcatcccctcgggtgtaatcagaatagctgatgtagtctcagtgagcccatatccttgcctgatacctggcaga
tggaacctcttggcaaccgcttccccgacttccttagagagggggagcgccaccagaagcaatttcgtgtaaattagataaat
cgtatttgtcaatcagagtgcttttggcgaagaaggagaatagggttggcaccagcagcgcactttgaatcttgtaatcctga
aggctcctcagaaacagctcttcttcaaatctatacattaagacgactcgaaatccacatatcaaatatccgagtgtagtaaac
attccaaaaccgtgatggaatggaacaacacttaaaatcgcagtatccggaatgatttgattgccaaaaataggatctctggc
atgcgagaatctcacgcaggcagttctatgaggcagagcgacaccttaggcagaccagtagatccagaggagttcatgat
cagtgcaattgtcttgtccctatcgaaggactctggcacaaaatcgtattcattaaaaccgggaggtagatgagatgtgacga
acgtgtacatcgactgaaatccctggtaatccgttttagaatccatgataataatttttttggatgattgggagcttttttgcacgtt
caaaatttttttgcaaccccttttttggaaacgaacaccacggtaggctgcgaaatgcccatactgttgagcaattcacgttcatta
taaatgtcgttcgcgggcgcaactgcaactccgataaataacgcgcccaacaccggcataaagaattgaagagagttttca
ctgcatacgacgattctgtgatttgtattcagcccatatcgtttcatagcttctgccaaccgaacggacatttcgaagtactcag
cgtaagtgatgtccacctcgatatgtgcatctgtaaaagcaattgttccaggaaccagggcgtatctcttcatagccttatgca
gttgctctccagcggttccatcttccagcggatagaatggcgccgggcctttctttatgttttttggcgtcttccatggtgaattcc
gatcccctggggagagaggtcggtgattcggtcaacgagggagccgactgccgacgtgcgctccggaggcttgcaga
atgcggaacaccgcgcgggcaggaacagggcccacactaccgccccacaccccgcctcccgcaccgccccttcccgg
ccgctgctctcggcgcgccccgctgagcagccgctattggccacagcccatcgcggtcggcgcgctgccattgctccctg
gcgctgtccgtctgcgagggtactagtgagacgtgcgggcttccgtttgtcacgtccggcacgccgcgaaccgcaaggaac
cttcccgacttaggggcggagcaggaagcgtcgccgggggggcccacaagggtagcggcgaagatccgggtgacgctg
cgaacggacgtgaagaatgtgcgagacccagggtcggcgccgctgcgtttcccggaaccacgcccagagcagccgcg
tccctgcgcaaacccagggctgccttggaaaaggcgcaaccccaacccgtgggaattcgatatcaagcttgcctatgttc
ttttggaatctatccaagtcttatgtaaatgcttatgtaaaccataatatataaagagtgctgattttttgagtaaacttgcaacagtc
ctaacattcttctctcgtgtgtttgtgtctgttcgccatcccgtctccgctcgtcacttatccttcacttttcagagggtccccccgc
agatcccggtcaccctcaggtcggtcgacaaccatggtgagcaagggcgaggagctgttcaccggggtggtgcccatc
ctggtcgagctggacggcgacgtaaacggccacaagttcagcgtgtccggcgagggcgagggcgatgccacctacgg
caagctgaccctgaagttcatctgcaccaccggcaagctgcccgtgccctggcccaccctcgtgaccaccctgacctacg
gcgtgcagtgcttcagccgctaccccgaccacatgaagcagcacgacttcttcaagtccgccatgcccgaaggctacgtc
caggagcgcaccatcttcttcaaggacgacggcaactacaagacccgcgccgaggtgaagttcgagggcgacaccctg
gtgaaccgcatcgagctgaagggcatcgacttcaaggaggacggcaacatcctggggcacaagctggagtacaactaca
acagccacaacgtctatatcatggccgacaagcagaagaacggcatcaaggtgaacttcaagatccgccacaacatcgag
gacggcagcgtgcagctcgccgaccactaccagcagaacacccccatcggcgacggccccgtgctgctgcccgacaac
cactacctgagcacccagtccgccctgagcaaagaccccaacgagaagcgcgatcacatggtcctgctggagttcgtga
ccgccgccgggatcactctcggcatggacgagctgtacaagtaaagcggcctcgacaatcaacctctggattacaaaattt
gtgaaagattgactggtattcttaactatgttgctccttttacgctatgtggatacgctgctttaatgcctttgtatcatgctattgct Fig. 9b (continued)

tcccgtatggctttcattttctcctccttgtataaatcctggttgctgtctctttatgaggagttgtggcccgttgtcaggcaacgtg
gcgtggtgtgcactgtgtttgctgacgcaaccccactggttggggcattgccaccacctgtcagctccttccgggactttc
gctttccccctccctattgccacggcggaactcatcgccgcctgccttgcccgctgctggacaggggctcggctgttgggc
actgacaattccgtggtgttgtcggggaagctgacgtcctttccatggctgctcgcctgtgttgccacctggattctgcgcgg
gacgtccttctgctacgtcccttcggccctcaatccagcggaccttccttcccgcggcctgctgccggctctgcggcctcttc
cgcgtcttcgccttcgccctcagacgagtcggatctccctttgggccgcctccccgcctggaattcgagctcggtaccctttaa
gaccaatgacttacaaggcagctgtagatcttagccacttttaaaagaaaagggggggactggaagggctaattcactccca
acgaagacaagatctgcttttgcttgtactgggtctctctggttagaccagatctgagcctgggagctctctggctaactagg
gaacccactgcttaagcctcaataaagcttgccttgagtgcttcaagtagtgtgtgcccgtctgttgtgtgactctggtaactag
agatccctcagacccttttagtcagtgtggaaaatctctagcagtagtagttcatgtcatcttattattcagtatttataacttgcaa
agaaatgaatatcagagagtgagaggaacttgtttattgcagcttataatggttacaaataaagcaatagcatcacaaatttca
caaataaagcattttttcactgcattctagttgtggtttgtccaaactcatcaatgtatcttatcatgtctggctctagctatcccgc
ccctaactccgcccagttccgcccattctccgccccatggctgactaattttttttatttatgcagaggccgaggccgcctcgg
cctctgagctattccagaagtagtgaggaggcttttttggaggcctaggcttttgcgtcgagacgtacccaattcgccctatag
tgagtcgtattacgcgcgctcactggccgtcgttttacaacgtcgtgactgggaaaaccctggcgttacccaacttaatcgcc
ttgcagcacatccccctttcgccagctggcgtaatagcgaagaggcccgcaccgatcgcccttcccaacagttgcgcagc
ctgaatggcgaatggcgcgacgcgccctgtagcggcgcattaagcgcggcgggtgtggtggttacgcgcagcgtgacc
gctacacttgccagcgccctagcgcccgctcctttcgctttcttcccttcctttctcgccacgttcgccggctttccccgtcaag
ctctaaatcggggggctcccctttagggttccgatttagtgctttacggcacctcgaccccaaaaaacttgattagggtgatggtt
cacgtagtgggccatcgccctgatagacggtttttcgccctttgacgttggagtccacgttctttaatagtggactcttgttcca
aactggaacaacactcaaccctatctcggtctattcttttgatttataagggattttgccgatttcggcctattggttaaaaaatga
gctgatttaacaaaaatttaacgcgaattttaacaaaatattaacgtttacaatttcc

Fig. 10b caggtggcacttttcggggaaatgtgcgcggaaccccctatttgtttattttttctaaatacattcaaatatgtatccgctcatgaga
caataaccctgataaatgcttcaataatattgaaaaaggaagagtatgagtattcaacatttccgtgtcgcccttattcccttttt
gcggcatttgccttcctgttttgctcacccagaaacgctggtgaaagtaaaagatgctgaagatcagttgggtgcacgagt
gggttacatcgaactggatctcaacagcggtaagatccttgagagttttcgccccgaagaacgttttccaatgatgagcacttt
taaagttctgctatgtggcgcggtattatcccgtattgacgccgggcaagagcaactcggtcgccgcatacactattctcaga
atgacttggttgagtactcaccagtcacagaaaagcatcttacggatggcatgacagtaagagaattatgcagtgctgccat
aaccatgagtgataacactgcggccaacttacttctgacaacgatcggaggaccgaaggagctaaccgcttttttgcacaac
atgggggatcatgtaactcgccttgatcgttgggaaccggagctgaatgaagccataccaaacgacgagcgtgacaccac
gatgcctgtagcaatggcaacaacgttgcgcaaactattaactggcgaactacttactctagcttcccggcaacaattaatag
actggatggaggcggataaagttgcaggaccacttctgcgctcggcccttccggctggctggtttattgctgataaatctgg
agccggtgagcgtgggtctcgcggtatcattgcagcactggggccagatggtaagccctcccgtatcgtagttatctacac
gacggggagtcaggcaactatggatgaacgaaatagacagatcgctgagataggtgcctcactgattaagcattggtaact
gtcagaccaagttactcatatatactttagattgatttaaaacttcattttaatttaaaaggatctaggtgaagatcctttttgata
atctcatgaccaaaatcccttaacgtgagttttcgttccactgagcgtcagaccccgtagaaaagatcaaaggatcttcttgag
atcctttttttctgcgcgtaatctgctgcttgcaaacaaaaaaaccaccgctaccagcggtggtttgtttgccggatcaagagct
accaactctttttccgaaggtaactggcttcagcagagcgcagataccaaatactgtccttctagtgtagccgtagttaggcc
accacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcac
acagcccagcttggagcgaacgacctacaccgaactgagatacctacagcgtgagctatgagaaagcgccacgcttccc
gaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctg
cgttatcccctgattctgtggataaccgtattaccgcctttgagtgagctgataccgctcgccgcagccgaacgaccgagcg
cagcgagtcagtgagcgaggaagcggaagagcgcccaatacgcaaaccgcctctccccgcgcgttggccgattcattaa
tgcagctggcacgacaggtttcccgactggaaagcgggcagtgagcgcaacgcaattaatgtgagttagctcactcattag
gcaccccaggctttacactttatgcttccggctcgtatgttgtgtggaattgtgagcggataacaatttcacacaggaaacagc
tatgaccatgattacgccaagcgcgcaattaaccctcactaaagggaacaaaagctggagctgcaagcttggccattgcat
acgttgtatccatatcataatatgtacatttatattggctcatgtccaacattaccgccatgttgacattgattattgactagttatta
atagtaatcaattacggggtcattagttcatagcccatatatggagttccgcgttacataacttacggtaaatggcccgcctgg
ctgaccgcccaacgacccccgcccattgacgtcaataatgacgtatgttcccatagtaacgccaatagggactttccattga
cgtcaatggtggagtatttacggtaaactgcccacttggcagtacatcaagtgtatcatatgccaagtacgccccctattga
cgtcaatgacggtaaatggcccgcctggcattatgcccagtacatgaccttatgggactttcctacttggcagtacatctacgt
attagtcatcgctattaccatggtgatgcggttttggcagtacatcaatgggcgtggatagcggtttgactcacggggatttcc
aagtctccaccccattgacgtcaatgggagtttgttttggcaccaaaatcaacgggactttccaaaatgtcgtaacaactccg
ccccattgacgcaaatgggcggtaggcgtgtacggtgggaggtctatataagcagagctcgtttagtgaaccggggtctct
ctggttagaccagatctgagcctgggagctctctggctaactagggaacccactgcttaagcctcaataaagcttgccttga
gtgcttcaagtagtgtgtgcccgtctgttgtgtgactctggtaactagagatccctcagacccttttagtcagtgtggaaaatct
ctagcagtggcgcccgaacagggacctgaaagcgaaagggaaaccagagctctctcgacgcaggactcggcttgctga
agcgcgcacggcaagaggcgaggggcggcgactggtgagtacgccaaaaattttgactagcggaggctagaaggaga
gagatgggtgcgagagcgtcagtattaagcgggggagaattagatcgcgatgggaaaaaattcggttaaggccagggggg
aaagaaaaaatataaattaaaacatatagtatgggcaagcagggagctagaacgattcgcagttaatcctggcctgttagaa
acatcagaaggctgtagacaaatactgggacagctacaaccatcccttcagacaggatcagaagaacttagatcattatata
atacagtagcaaccctctattgtgtgcatcaaaggatagagataaaagacaccaaggaagctttagacaagatagaggaag
agcaaaacaaaagtaagaccaccgcacagcaagcggccgctgatcttcagacctggaggaggagatatgagggacaat
tggagaagtgaattatataaatataaagtagtaaaaattgaaccattaggagtagcacccaccaaggcaaagagaagagtg
gtgcagagagaaaaaagagcagtgggaataggagctttgttccttgggttcttgggagcagcaggaagcactatgggcgc
agcctcaatgacgctgacggtacaggccagacaattattgtctggtatagtgcagcagcagaacaatttgctgagggctatt
gaggcgcaacagcatctgttgcaactcacagtctggggcatcaagcagctccaggcaagaatcctggctgtggaaagata Fig. 10b (continued)

cctaaaggatcaacagctcctggggatttggggttgctctggaaaactcatttgcaccactgctgtgccttggaatgctagttg
gagtaataaatctctggaacagatttggaatcacacgacctggatggagtgggacagagaaattaacaattacacaagctta
atacactccttaattgaagaatcgcaaaaccagcaagaaaagaatgaacaagaattattggaattagataaatgggcaagttt
gtggaattggtttaacataacaaattggctgtggtatataaaattattcataatgatagtaggaggcttggtaggtttaagaatag
tttttgctgtactttctatagtgaatagagttaggcagggatattcaccattatcgtttcagacccacctcccaaccccgagggg
acccgacaggcccgaaggaatagaagaagaaggtggagagagagacagagacagatccattcgattagtgaacggatc
tcgacggtatcggttaacttttaaaagaaaaggggggattgggggtacagtgcaggggaaagaatagtagacataatag
caacagacatacaaactaaagaattacaaaaacaaattacaaaaatttcaaaattttatcgatcacgagactagcctcgagga
gatctgatcataatcagccataccacatttgtagaggttttacttgctttaaaaaacctcccacacctcccccctgaacctgaaac
ataaaatgaatgcaattgttgttgttaacttgtttattgcagcttataatggttacaaataaggcaatagcatcacaaatttcacaa
ataaggcattttttttcactgcattctagtttggtttgtccaaactcatcaatgtatcttatcatgtctggatctcaaatccctcggaa
gctgcgcctgtcttaggttggagtgatacatttttatcacttttacccgtctttggattaggcagtagctctgacggccctcctgt
cttaggttagtgaaaaatgtcactctcttaccgtcattggctgtccagcttagctcgcagggaggtggtctggatccaccat
gtctagagaataggaacttcggaataggaacttcgcggccgcttacttgtacagctcgtccatgccgagagtgatcccggc
ggcggtcacgaactccagcaggaccatgtgatcgcgcttctcgttggggtctttgctcagggcggactgggtgctcaggta
gtggttgtcgggcagcagcacggggccgtcgccgatgggggtgttctgctggtagtggtcggcgagctgcacgctgccg
tcctcgatgttgtggcggatcttgaagttcaccttgatgccgttcttctgcttgtcggccatgatatagacgttgtggctgttgta
gttgtactccagcttgtgccccaggatgttgccgtcctccttgaagtcgatgcccttcagctcgatgcggttcaccagggtgtc
gccctcgaacttcacctcggcgcgggtcttgtagttgccgtcgtccttgaagaagatggtgcgctcctggacgtagccttcg
ggcatggcggacttgaagaagtcgtgctgcttcatgtggtcggggtagcggctgaagcactgcacgccgtaggtcagggt
ggtcacgagggtgggccagggcacgggcagcttgccggtggtgcagatgaacttcaggggtcagcttgccgtaggtggc
atcgccctcgccctcgccggacacgctgaacttgtggccgtttacgtcgccgtccagctcgaccaggatgggcaccacc
cggtgaacagctcctcgcccttgctcaccatggttgtcgacccgacctgagggtgacccgggatctgcgggggggaccctct
gaaaagtgaaggataagtgacgagcggagacgggatggcgaacagacacaaacacacgagagaagaatgttaggact
gttgcaagtttactcaaaaaatcagcactcttttatattatggtttacataagcatttacataagacttggatagattccaaaagaa
cataggcaagcttgatatcgaattcccacggggttggggttgcgccttttccaaggcagccctgggtttgcgcagggacgc
ggctgctctgggcgtggttccgggaaacgcagcggcgccgaccctgggtctcgcacattcttcacgtccgttcgcagcgt
cacccgatcttcgccgctaccccttgtgggccccccggcgacgcttcctgctccgcccctaagtcgggaaggttccttgcg
gttcgcggcgtgccggacgtgacaaacggaagccgcacgtctcactagtaccctcgcagacggacagcgccagggagc
aatggcagcgcgccgaccgcgatgggctgtggccaatagcggctgctcagcggggcgcgccgagagcagcggccgg
gaaggggcggtgcgggaggcggggtgtggggcggtagtgtgggccctgttcctgcccgcgcggtgttccgcattctgca
agcctccggagcgcacgtcggcagtcggctccctcgttgaccgaatcaccgacctctctcccagggggatccccgggg
ctgcaggaattcggggccgcggccagctccggcgggcagggggggcgctggagcgcagcgcagcgcagcccccatcag
tccgcaaagcggaccgagctggaagtcgagcgctgccgcggggaggcgggcgatgggggcaggtgccaccggccgc
gccatggacgggccgcgcctgctgctgttgctgcttctggggggtgtcccttggaggtgccaaggaggcatgccccacagg
cctgtacacacacagcggtgagtgctgcaaagcctgcaacctgggcgagggtgtggcccagccttgtggagccaaccag
accgtgtgtgagccctgcctggacagcgtgacgttctccgacgtggtgagcgcgaccgagccgtgcaagccgtgcaccg
agtgcgtggggctccagagcatgtcggcgccgtgcgtggaggccgacgacgccgtgtgccgctgcgcctacggctact
accaggatgagacgactgggcgctgcgaggcgtgccgcgtgtgcgaggcgggctcgggcctcgtgttctcctgccagg
acaagcagaacaccgtgtgcgaggagtgccccgacggcacgtattccgacgaggccaaccacgtggacccgtgcctgc
cctgcaccgtgtgcgaggacaccgagcgccagctccgcgagtgcacacgctgggccgacgccgagtgcgaggagatc
cctggccgttggattacacggtccacaccccagagggctcggacagcacagcccccagcacccaggagcctgaggca
cctccagaacaagacctcatagccagcacggtggcaggtgtggtgaccacagtgatgggcagctcccagcccgtggtga
cccgaggcaccaccgacaacctcatccctgtctattgctccatcctggctgctgtggttgtgggccttgtggcctacatagcc
ttcaagaggtggaacaggggggatcctctagagtcgagtctagagtcgacaatcaacctctggattacaaaattgtgaaaga
ttgactggtattcttaactatgttgctccttttacgctatgtggatacgctgctttaatgcctttgtatcatgctattgcttcccgtatg
gctttcatttctcctccttgtataaatcctggttgctgtctctttatgaggagttgtggcccgttgtcaggcaacgtggcgtggtg
tgcactgtgtttgctgacgcaacccccactggttggggcattgccaccacctgtcagctcctttccgggactttcgctttcccc Fig. 10b (continued)

ctccctattgccacggcggaactcatcgccgcctgccttgcccgctgctggacaggggctcggctgttgggcactgacaat
tccgtggtgttgtcggggaagctgacgtcctttccatggctgctcgcctgtgttgccacctggattctgcgcgggacgtcctt
ctgctacgtcccttcggccctcaatccagcggaccttccttcccgcggcctgctgccggctctgcggcctcttccgcgtcttc
gccttcgccctcagacgagtcggatctccctttgggccgcctccccgcctggaattcgagctcggtacctttaagaccaatg
acttacaaggcagctgtagatcttagccacttttaaaagaaaagggggactggaaggctaattcactcccaacgaaga
caagatctgcttttgcttgtactgggtctctctggttagaccagatctgagcctgggagctctctggctaactagggaaccca
ctgcttaagcctcaataaagcttgccttgagtgcttcaagtagtgtgtgcccgtctgttgtgtgactctggtaactagagatccc
tcagacccttttagtcagtgtggaaaatctctagcagtagtagttcatgtcatcttattattcagtatttataacttgcaaagaaatg
aatatcagagagtgagaggaacttgtttattgcagcttataatggttacaaataaagcaatagcatcacaaatttcacaaataa
agcatttttttcactgcattctagttgtggtttgtccaaactcatcaatgtatcttatcatgtctggctctagctatcccgcccctaac
tccgcccagttccgcccattctccgccccatggctgactaatttttttatttatgcagaggccgaggccgcctcggcctctga
gctattccagaagtagtgaggaggcttttttggaggcctaggcttttgcgtcgagacgtacccaattcgccctatagtgagtc
gtattacgcgcgctcactggccgtcgttttacaacgtcgtgactgggaaaaccctggcgttacccaacttaatcgccttgcag
cacatccccctttcgccagctggcgtaatagcgaagaggcccgcaccgatcgcccttcccaacagttgcgcagcctgaat
ggcgaatggcgcgacgcgcctgtagcggcgcattaagcgcggcgggtgtggtggttacgcgcagcgtgaccgctaca
cttgccagcgccctagcgcccgctcctttcgctttcttcccttcctttctcgccacgttcgccggctttccccgtcaagctctaa
atcgggggctccctttagggttccgatttagtgctttacggcacctcgaccccaaaaaacttgattagggtgatggttcacgta
gtgggccatcgccctgatagacggtttttcgccctttgacgttggagtccacgttctttaatagtggactcttgttccaaactgg
aacaacactcaaccctatctcggtctattcttttgatttataagggattttgccgatttcggcctattggttaaaaaatgagctgatt
taacaaaatttaacgcgaattttaacaaaatattaacgtttacaatttcc

Fig. 11b caggtggcacttttcggggaaatgtgcgcggaaccccctatttgtttatttttctaaatacattcaaatatgtatccgctcatgaga
caataaccctgataaatgcttcaataatattgaaaaaggaagagtatgagtattcaacatttccgtgtcgcccttattccctttttt
gcggcatttttgccttcctgttttttgctcacccagaaacgctggtgaaagtaaaagatgctgaagatcagttgggtgcacgagt
gggttacatcgaactggatctcaacagcggtaagatccttgagagttttcgccccgaagaacgttttccaatgatgagcacttt
taaagttctgctatgtggcgcggtattatcccgtattgacgccgggcaagagcaactcggtcgccgcatacactattctcaga
atgacttggttgagtactcaccagtcacagaaaagcatcttacggatggcatgacagtaagagaattatgcagtgctgccat
aaccatgagtgataacactgcggccaacttacttctgacaacgatcggaggaccgaaggagctaaccgcttttttgcacaac
atgggggatcatgtaactcgccttgatcgttgggaaccggagctgaatgaagccataccaaacgacgagcgtgacaccac
gatgcctgtagcaatggcaacaacgttgcgcaaactattaactggcgaactacttactctagcttcccggcaacaattaatag
actggatggaggcggataaagttgcaggaccacttctgcgctcggcccttccggctggctggtttattgctgataaatctgg
agccggtgagcgtgggtctcgcggtatcattgcagcactggggccagatggtaagccctcccgtatcgtagttatctacac
gacggggagtcaggcaactatggatgaacgaaatagacagatcgctgagataggtgcctcactgattaagcattggtaact
gtcagaccaagtttactcatatatactttagattgatttaaaacttcattttaatttaaaaggatctaggtgaagatcctttttgata
atctcatgaccaaaatcccttaacgtgagttttcgttccactgagcgtcagaccccgtagaaaagatcaaaggatcttcttgag
atccttttttctgcgcgtaatctgctgcttgcaaacaaaaaaaccaccgctaccagcggtggtttgtttgccggatcaagagct
accaactctttttccgaaggtaactggcttcagcagagcgcagataccaaatactgtccttctagtgtagccgtagttaggcc
accacttcaagaactctgtagcaccgcctacatacctcgctctgctaatcctgttaccagtggctgctgccagtggcgataag
tcgtgtcttaccgggttggactcaagacgatagttaccggataaggcgcagcggtcgggctgaacggggggttcgtgcac
acagcccagcttggagcgaacgacctacaccgaactgagatacctacagcgtgagctatgagaaagcgccacgcttccc
gaagggagaaaggcggacaggtatccggtaagcggcagggtcggaacaggagagcgcacgagggagcttccaggg
ggaaacgcctggtatctttatagtcctgtcgggtttcgccacctctgacttgagcgtcgatttttgtgatgctcgtcaggggggg
cggagcctatggaaaaacgccagcaacgcggcctttttacggttcctggccttttgctggccttttgctcacatgttctttcctg
cgttatcccctgattctgtggataaccgtattaccgcctttgagtgagctgataccgctcgccgcagccgaacgaccgagcg
cagcgagtcagtgagcgaggaagcggaagagcgcccaatacgcaaaccgcctctccccgcgcgttggccgattcattaa
tgcagctggcacgacaggtttcccgactggaaagcgggcagtgagcgcaacgcaattaatgtgagttagctcactcattag
gcaccccaggctttacactttatgcttccggctcgtatgttgtgtggaattgtgagcggataacaatttcacacaggaaacagc
tatgaccatgattacgccaagcgcgcaattaaccctcactaaagggaacaaaagctggagctgcaagcttggccattgcat
acgttgtatccatatcataatatgtacatttatattggctcatgtccaacattaccgccatgttgacattgattattgactagttatta
atagtaatcaattacggggtcattagttcatagcccatatatggagttccgcgttacataacttacggtaaatggcccgcctgg
ctgaccgcccaacgacccccgcccattgacgtcaataatgacgtatgttcccatagtaacgccaatagggactttccattga
cgtcaatgggtggagtatttacggtaaactgcccacttggcagtacatcaagtgtatcatatgccaagtacgccccctattga
cgtcaatgacggtaaatggcccgcctggcattatgcccagtacatgaccttatgggactttcctacttggcagtacatctacgt
attagtcatcgctattaccatggtgatgcggttttggcagtacatcaatgggcgtggatagcggtttgactcacggggatttcc
aagtctccaccccattgacgtcaatgggagtttgttttggcaccaaaatcaacgggactttccaaaatgtcgtaacaactccg
ccccattgacgcaaatgggcggtaggcgtgtacggtgggaggtctatataagcagagctcgtttagtgaaccggggtctct
ctggttagaccagatctgagcctgggagctctctggctaactagggaacccactgcttaagcctcaataaagcttgccttga
gtgcttcaagtagtgtgtgcccgtctgttgtgtgactctggtaactagagatccctcagacccttttagtcagtgtggaaaatct
ctagcagtggcgcccgaacaggggacctgaaagcgaaagggaaaccagagctctctcgacgcaggactcggcttgctga
agcgcgcacggcaagaggcgaggggcggcgactggtgagtacgccaaaaattttgactagcggaggctagaaggaga
gagatgggtgcgagagcgtcagtattaagcggggagaattagatcgcgatgggaaaaaattcggttaaggccagggggg
aaagaaaaaatataaattaaaacatatagtatgggcaagcagggagctagaacgattcgcagttaatcctggcctgttagaa
acatcagaaggctgtagacaaatactgggacagctacaaccatcccttcagacaggatcagaagaacttagatcattatata
atacagtagcaaccctctattgtgtgcatcaaaggatagagataaaagacaccaaggaagctttagacaagatagaggaag
agcaaaacaaaagtaagaccaccgcacagcaagcggccgctgatcttcagacctggaggaggagatatgagggacaat
tggagaagtgaattatataaatataaagtagtaaaaattgaaccattaggagtagcacccaccaaggcaaagaagaagagtg
gtgcagagagaaaaaagagcagtgggaataggagctttgttccttgggttcttgggagcagcaggaagcactatgggcgc
agcctcaatgacgctgacggtacaggccagacaattattgtctggtatagtgcagcagcagaacaatttgctgagggctatt
gaggcgcaacagcatctgttgcaactcacagtctggggcatcaagcagctccaggcaagaatcctggctgtggaaagata Fig. 11b (continued)

cctaaaggatcaacagctcctggggatttggggttgctctggaaaactcatttgcaccactgctgtgccttggaatgctagttg
gagtaataaatctctggaacagattggaatcacacgacctggatggagtgggacagagaaattaacaattacacaagctta
atacactccttaattgaagaatcgcaaaaccagcaagaaaagaatgaacaagaattattggaattagataaatgggcaagttt
gtggaattggtttaacataacaaattggctgtggtatataaaattattcataatgatagtaggaggcttggtaggtttaagaatag
tttttgctgtactttctatagtgaatagagttaggcagggatattcaccattatcgtttcagacccacctcccaaccccgagggg
acccgacaggcccgaaggaatagaagaagaaggtggagagagagacagagacagatccattcgattagtgaacggatc
tcgacggtatcggttaactttaaaagaaaaggggggattggggggtacagtgcaggggaaagaatagtagacataatag
caacagacatacaaactaaagaattacaaaaacaaattacaaaaattcaaaattttatcgatcacgagactagcctcgagag
atctgatcataatcagccataccacatttgtagaggttttacttgctttaaaaaacctcccacacctcccctgaacctgaaaca
taaaatgaatgcaattgttgttgttaacttgtttattgcagcttataatggttacaaataaggcaatagcatcacaaatttcacaaa
taaggcatttttttcactgcattctagttttggtttgtccaaactcatcaatgtatcttatcatgtctggatctcaaatccctcggaag
ctgcgcctgtcttaggttggagtgatacattttttatcacttttacccgtctttggattaggcagtagctctgacggccctcctgtct
taggttagtgaaaaatgtcactctcttacccgtcattggctgtccagcttagctcgcaggggaggtggtctggatccgagctc
gaattggccgctttacttgtacagctcgtccatgccgagagtgatcccggcggcggtcacgaactccagcaggaccatgtg
atcgcgcttctcgttggggtcttgctcagggcggactgggtgctcaggtagtggttgtcgggcagcagcacggggccgtc
gccgatggggtgttctgctggtagtggtcggcgagctgcacgctgccgtcctcgatgttgtggcggatcttgaagttcacc
ttgatgccgttcttctgcttgtcggccatgatatagacgttgtggctgttgtagttgtactccagcttgtgccccaggatgttgcc
gtcctccttgaagtcgatgcccttcagctcgatgcggttcaccagggtgtcgccctcgaacttcacctcggcgcgggtcttgt
agttgccgtcgtccttgaagaagatggtgcgctcctggacgtagccttcgggcatggcggacttgaagaagtcgtgctgctt
catgtggtcggggtagcggctgaagcactgcacgccgtaggtcagggtggtcacgagggtgggccagggcacgggca
gcttgccggtggtgcagatgaacttcagggtcagcttgccgtaggtggcatcgccctcgccctcgccgacacgctgaact
tgtggccgtttacgtcgccgtccagctcgaccaggatgggcaccaccccggtgaacagctcctcgcccttgctcaccatgg
tgaattccgcggaggctggatcggtcccggtgtcttctatggaggtcaaaacagcgtggatggcgtctccaggcgatctga
cggttcactaaacgagctctgcttatataggcctccaccgtacacgcctacccctcgagaagcttgattaaccgtgtcggct
ccagatctggcctccgcgccgggttttggcgcctcccgcgggcgcccccctcctcacggcgagcgctgccacgtcagac
gaagggcgcagcgagcgtcctgatccttccgcccgacgctcaggacagcggcccgctgctcataagactcggccttag
aaccccagtatcagcagaaggacatttaggacgggacttgggtgactctagggcactggttttctttccagagagcggaac
aggcgaggaaaagtagtcccttctcggcgattctgcggagggatctccgtggggcggtgaacgccgatgattatataagg
acgcgccgggtgtggcacagctagttccgtcgcagccgggatttgggtcgcggttcttgtttgtggatcgctgtgatcgtca
cttggtgagttgcgggctgctgggctggccggggcttttcgtggccgccggccgctcggtgggacggaagcgtgtggag
agaccgccaagggctgtagtctgggtccgcgagcaaggttgccctgaactgggggttgggggagcgcacaaaatggc
ggctgttcccgagtcttgaatggaagacgcttgtaaggcgggctgtgaggtcgttgaaacaaggtgggggcatggtggg
cggcaagaacccaaggtcttgaggccttcgctaatgcgggaaagctcttattcgggtgagatgggctggggcaccatctg
gggaccctgacgtgaagtttgtcactgactggagaactcgggtttgtcgtctggttgcgggggcggcagttatgcggtgcc
gttgggcagtgcacccgtacctttgggagcgcgcgcctcgtcgtgtcgtgacgtcacccgttctgttggcttataatgcagg
gtggggccacctgccggtaggtgtgcggtaggcttttctccgtcgcaggacgcagggttcgggcctagggtaggctctcct
gaatcgacaggcgccggacctctggtgaggggagggataagtgaggcgtcagtttctttggtcggttttatgtacctatcttc
ttaagtagctgaagctccggttttgaactatgcgctcggggttggcgagtgtgttttgtgaagttttttaggcaccttttgaaatgt
aatcatttgggtcaatatgtaattttcagtgttagactagtaaattgtccgctaaattctggccgttttggcttttttgttagacgaa
gcttgggctgcaggaattcgggccgcggccagctccggcgggcaggggggcgctggagcgcagcgcagcgcagcc
ccatcagtccgcaaagcggaccgagctggaagtcgagcgctgccgcgggaggcggcgatggggcaggtgccacc
ggccgcgccatgacgggccgcgcctgctgctgttgctgcttctgggggtgtcccttggaggtgccaaggaggcatgcc
ccacaggcctgtacacacacagcggtgagtgctgcaaagcctgcaacctgggcgagggtgtggcccagccttgtggagc
caaccagaccgtgtgtgagccctgcctggacagcgtgacgttctccgacgtggtgagcgcgaccgagccgtgcaagccg
tgcaccgagtgcgtggggctccagagcatgtcggcgccgtgcgtggaggccgacgacgccgtgcgcgctgcgcctac
ggctactaccaggatgagacgactgggcgctgcgaggcgtgccgcgtgtgcgaggcgggctcgggcctcgtgttctcct
gccaggacaagcagaacaccgtgtgcgaggagtgccccgacggcacgtattccgacgaggccaaccacgtggacccg
tgcctgccctgcaccgtgtgcgaggacaccgagcgccagctccgcgagtgcacacgctgggccgacgccgagtgcga Fig. 11b (continued)

```
ggagatccctggccgttggattacacggtccacaccccagagggctcggacagcacagcccccagcacccaggagcc
tgaggcacctccagaacaagacctcatagccagcacggtggcaggtgtggtgaccacagtgatgggcagctcccagccc
gtggtgacccgaggcaccaccgacaacctcatccctgtctattgctccatcctggctgctgtggttgtgggccttgtggccta
catagccttcaagaggtggaacagggggatcctctagagtcgagtctagagtcgacaatcaacctctggattacaaaatttg
tgaaagattgactggtattcttaactatgttgctccttttacgctatgtggatacgctgctttaatgcctttgtatcatgctattgcttc
ccgtatggctttcattttctcctccttgtataaatcctggttgctgtctctttatgaggagttgtggcccgttgtcaggcaacgtgg
cgtggtgtgcactgtgtttgctgacgcaaccccactggttggggcattgccaccacctgtcagctcctttccgggactttcg
ctttccccctccctattgccacggcggaactcatcgccgcctgccttgcccgctgctggacaggggctcggctgttgggca
ctgacaattccgtggtgttgtcggggaagctgacgtcctttccatggctgctcgcctgtgttgccacctggattctgcgcggg
acgtccttctgctacgtcccttcggccctcaatccagcggaccttccttcccgcggcctgctgccggctctgcggcctcttcc
gcgtcttcgccttcgccctcagacgagtcggatctcccttgggccgcctcccgcctggaattcgagctcggtacctttaag
accaatgacttacaaggcagctgtagatcttagccactttttaaaagaaaagggggactggaagggctaattcactcccaa
cgaagacaagatctgcttttgcttgtactgggtctctctggttagaccagatctgagcctgggagctctctggctaactaggg
aacccactgcttaagcctcaataaagcttgccttgagtgcttcaagtagtgtgtgcccgtctgttgtgtgactctggtaactaga
gatccctcagacccttttagtcagtgtggaaaatctctagcagtagtagttcatgtcatcttattattcagtatttataacttgcaaa
gaaatgaatatcagagagtgagaggaacttgtttattgcagcttataatggttacaaataaagcaatagcatcacaaatttcac
aaataaagcatttttttcactgcattctagttgtggtttgtccaaactcatcaatgtatcttatcatgtctggctctagctatcccgcc
cctaactccgcccagttccgcccattctccgccccatggctgactaatttttttttatttatgcagaggccgaggccgcctcggc
ctctgagctattccagaagtagtgaggaggcttttttggaggcctaggcttttgcgtcgagacgtacccaattcgccctatagt
gagtcgtattacgcgcgctcactggccgtcgttttacaacgtcgtgactgggaaaaccctggcgttacccaacttaatcgcct
tgcagcacatccccctttcgccagctggcgtaatagcgaagaggcccgcaccgatcgcccttcccaacagttgcgcagcc
tgaatggcgaatggcgcgacgcgccctgtagcggcgcattaagcgcggcgggtgtggtggttacgcgcagcgtgaccg
ctacacttgccagcgccctagcgcccgctcctttcgctttcttcccttcctttctcgccacgttcgccggctttccccgtcaagc
tctaaatcgggggctccctttagggttccgatttagtgctttacggcacctcgaccccaaaaaacttgattagggtgatggttc
acgtagtgggccatcgccctgatagacggtttttcgccctttgacgttggagtccacgttctttaatagtggactcttgttccaa
actggaacaacactcaaccctatctcggtctattcttttgatttataagggattttgccgatttcggcctattggttaaaaaatgag
ctgatttaacaaaaatttaacgcgaattttaacaaaatattaacgtttacaatttcc
```

LENTIVIRAL VECTORS CARRYING SYNTHETIC BI-DIRECTIONAL PROMOTERS AND USES THEREOF

This application is a National Stage Application of International Application No. No. PCT/IT04/000227, filed Apr. 21, 2004, claiming the benefit of U.S. Ser. No. 60/465,080, filed Apr. 24, 2003 the contents of the preceding applications are incorporated by reference into this application.

The present invention relates to bidirectional promoters allowing efficient and coordinate expression of two or more genes, to gene transfer vectors containing these promoters, to particles transducing said vectors into a cell, to the use of said vectors for the delivery and expression of multiple genes in target cells, also for gene therapy, and for the manufacturing of medicaments.

TECHNICAL BACKGROUND

Expression of multiple transgenes within the same target cells is required for several gene transfer and therapy applications[1]. Gene-function studies are best performed by expressing cDNAs together with a marker gene; by this approach, genetically-modified cells can be identified and monitored in vitro and in vivo. Similarly, gene therapy applications can be improved by purification of gene-corrected cells before in vivo administration, taking advantage of coordinate expression of selectable markers. Genetically-modified cells can be amplified ex vivo or in vivo by introducing growth-promoting or drug-resistance genes together with the therapeutic gene, as recently shown by MGMT-mediated selection of transduced Hematopoietic Stem Cells (HSC)[2]; using this approach, the efficacy of gene therapy can be increased, and its application potentially extended to a wide spectrum of diseases[3,4]. Conversely, genetically-modified cells expressing conditionally cytotoxic genes, together with the therapeutic gene, can be eliminated in vivo, if adverse events occur; this approach is used to control graft-versus-host disease following donor T-lymphocytes infusion to treat leukemia relapse[5]; it may also provide an important safety provision in HSC gene transfer, given the recent occurrence of leukemia related to vector integration in a successful clinical trial of X-linked Severe Combined ImmunoDeficiency[6]. Coordinate expression of more than one transgene is essential when the activity to be reconstituted by gene transfer depends on multiple subunits encoded by different genes, or requires the synergism of separate molecules. For instance, reconstitution of the dopamine biosynthetic pathway in striatal neurons of Parkinson's disease patients requires co-expression of tyrosine hydroxylase with GTp-cyclohydrolase I and/or DOPA decarboxylase[7]; cancer gene therapy may require co-expression of multiple antigens and/or cytokines in antigen-presenting cells for immunotherapy, and of two T-cell receptor chains in T-cells engineered for adoptive transfer[8].

In spite of such well-recognized needs, reaching coordinate, high-level expression of multiple transgenes in the majority of target cells has been a significant challenge for gene transfer technology. Two different transgenes have been expressed by two separate vectors; yet, only a fraction of target cells was transduced by both vectors and a heterogeneous population of cells was obtained that expressed either one or two genes in different ratios, preventing reliable studies and/or efficacious applications. Alternatively, two or more transgenes have been expressed by different promoters within the same vector[9]; yet, different tissue specificity and mutual interference between promoters often prevented efficient co-expression in the same target cells[10]. Differential splicing generates multiple transcripts from the same promoter, but it has proven difficult to adapt to viral delivery of multiple transgenes[11]. Chimeric polyproteins that self-process co-translationally into separate components have been generated using the self-cleaving peptide of the Foot and Mouth Disease Virus 2A[12,13]; however, application of this technology to multiple gene transfer has been limited until now because it requires sophisticated engineering, restricts both proteins to the same cellular compartment, and introduces sequence changes that may affect protein activity, stability, and immunogenicity. The most satisfactory approach to multiple gene transfer until now has relied on using internal ribosome entry sites (IRES's)[14]. These sequences, identified in viral and cellular transcripts, control translation in a $^{mRNA}$-Cap-independent manner and, when inserted between two genes in a bicistronic messenger RNA, allow translation of the downstream gene. The authors tested the performance of different IRES's in the context of self-inactivating (SIN) lentiviral vectors (LVs), and found significant limitations of this approach.

WO 02/064804 describes bi-directional dual promoter complexes that are effective for enhancing transcriptional activity of transgenes in plants.

The bi-directional promoters of the invention include a modified enhancer region with at least two core promoters on either side of the modified enhancer in a divergent orientation. The application refers to gene expression in plants. In addition, the approach requires the duplication of tandem oriented enhancer sequences in a modified internal region of the construct, to be joined by two identical or homologous minimal promoters on either sides. The instant invention does not require duplication of enhancer or any other sequences in the efficient promoter of the bi-directional construct, nor are need that the core promoters on either sides of it to share at least 30% identity. Finally, tandem duplication may be incompatible with retro/lentiviral delivery.

U.S. Pat. No. 6,388,170 discloses plant vectors, having bi-directional promoters, comprising a minimal promoter and a common promoter, wherein said minimal promoters is operably linked to said common promoter, in opposite orientation to said common promoter, and 5' to said common promoter. Promoter sequences derived from plants and plant-infecting viruses are disclosed dnd tested in plant cells or plant parts. Given the substantial evolutionary distance between plants and animals, U.S. Pat. No. 6,388,170 does not teach how to engineer animal promoters for bi-directional activity and whether bi-directional promoters may effectively work in animal cells. In addition, U.S. Pat. No. 6,388,170 does not teach how to engineer bi-directional promoters for gene expression in animals and in animal cells using the available gene transfer methods.

WO01/34825 discloses cell lines, plasmids and vectors useful for the production of recombinant viruses such as adenoviruses, which are useful in gene therapy. The cell lines, plasmids and vectors comprise inducible promoters, such as bi-directional promoters for the coordinate expression of bidirectionally cloned gene. However only bi-directional Tet-regulated constructs are disclosed.

Thus, the authors explored novel strategies to take full advantage of gene transfer systems, such as LV, that allow efficient ex vivo transduction and direct in vivo administration.

DESCRIPTION OF THE INVENTION

The authors developed a novel vector design in which synthetic bi-directional promoters mediated coordinate transcription of two divergent RNAs. The authors show that LVs carrying bi-directional promoters coordinately expressed two transgenes in the vast majority of transduced cells clearly outperforming the bicistronic vectors. The efficient performance of the new bi-directional LVs in primary hematopoietic cells, assayed ex vivo and after transplantation, and in several tissues in vivo, after direct vector delivery or transgenesis was established. The invention overcomes a long-standing hurdle in the quest for improved gene-expression tools and are expected to advance the reach and safety of gene therapy. It is therefore an object of the instant invention a bidirectional promoter for expression of at least two coding sequences in opposite direction in animal cells comprising 5' end to 3' end:

a) a first minimal promoter sequence derived from cytomegalovirus (CMV) or mouse mammary tumor virus (MMTV) genomes;
b) a full efficient promoter sequence derived from an animal gene; the two promoter sequences driving a coordinate transcription of said coding sequences in the opposite orientation.

In the ambit of the instant invention a full efficient promoter sequence means a sequence driving an efficient transcription of primary transcript. Preferably It comprises an enhancer region and a minimal promoter sequence, either distinct or overlapping. More preferably the full efficient promoter sequence derives from the phosphoglycerate kinase or from the ubiquitin promoter.

It is an object of the invention a bidirectional expression cassette essentially comprising the bidirectional promoter as above disclosed, convenient insertion sites positioned downstream to each promoter, and polyadenylation sites positioned downstream to each insertion site.

Preferably the bidirectional expression cassette further comprises at least one post-transcriptional regulatory element positioned upstream to one or each polyadenylation site. More preferably the bidirectional expression cassette further comprises at least one internal ribosome entry site (IRES) sequence to express three or more genes.

It is an object of the invention an expression construct containing the bidirectional promoter, as above disclosed.

It is an object of the invention an expression construct containing the bidirectional expression cassette, as above disclosed.

It is an object of the invention a gene transfer expression vector containing the expression construct as above disclosed further comprising lentiviral or retroviral sequences.

It is an object of the invention the use of the gene transfer expression vector for the delivery and expression of multiple genes in animal cells, preferably in vivo tissue animal cells, more preferably, brain neurons.

It is an object of the invention a method for the coordinate expression of two exogeneous coding sequences into an animal cell comprising the following steps:

a) cloning said coding sequences into the gene transfer expression vector according to claim 8, each coding sequence under the control of one of the two promoters of the bidirectional promoter;
b) transforming animal cells by means of said vectors;
c) allowing the expression of the vector.

Preferably the animal cell is a human cell, more preferably the human cell is a retransplantable human cell, even more preferably the retransplantable human cell is an hematopoietic cell.

Alternatively, the transformation of tissue cells in vivo may be performed by direct delivery of the vector, such as into brain neurons.

It is an object of the invention a method for generating a transgenic non human organism comprising the step of transforming appropriate cells by means of the gene transfer expression vector as disclosed above.

The vectors of the invention can be advantageously utilized for gene function and target validation studies in vitro and in vivo; gene therapy; expression of multiple genes in animal cells; generation of transgenic animals and eventually knock down of multiple genes; and for manufacturing of medicaments, as well.

FIGURE LEGENDS

The invention will be now described with reference to following Figures:

FIG. 1. Gene transfer performance of bicistronic lentiviral vectors. (a) Scheme of the proviral vector form. A bicistronic expression cassette containing an internal ribosome entry site (QRS) derived either from the encephalomyocarditis virus (EMCV), with wild-type (wt) or mutated (mut) translation start site, or from the 5' untranslated NF-kB repressing factor mRNA (NRF) was driven by the human immediate early cytomegalovirus (CMV) or phosphoglycerate kinase (PGK) promoter. ΔU3, R and U5, LTR regions with deletion in U3; SD and SA, splice donor and acceptor site; Ψ, encapsidation signal including the 5' portion of the gag gene (GA); RRE, Rev-response element; cPPT, central polypurine tract; WPRE, woodchuck hepatitis virus post-transcription regulatory element. (b) Southern blot analysis of HeLa cells transduced by the indicated monocistronic (CMV) or bicistronic vectors expressing luciferase (gene 1) and GFP (gene 2) from the CMV promoter, probed for the WPRE sequence. All vector integrated with the expected length of DNA. Vector copy number was determined relative to a plasmid standard curve and used to normalize vector stocks and ensure similar levels of integration for each vector in a given target cell type in the experiments shown in c-f. (c-f) Luciferase and GFP expression in human HeLa cells (c), umbilical vein endothelial cells (HUVEC, d), peripheral blood lymphocytes (PBL, e), and cord blood-derived CD34+ progenitors (f) transduced 5-7 days before with a monocistronic (□, CMV) or the indicated bicistronic CMV-luciferase-GFP vector. Left column, histograms representing net luciferase activity in cells extracts, mean±SD. Right panel, dot plots representing GFP expression by FACS analysis, the frequency and the mean fluorescence intensity (MFI, X) of GFP+ cells is indicated. The control monocistronic vector expressed luciferase in the histogram (O), and GFP in the left-most dot plot (CMV) for each cell type. (g, h) FACS analysis of ΔNGFR and GFP expression in 293T cells (g) and CD34+ progenitors (h) transduced by a EMCV wt IRES vector expressing ΔNGFR and GFP from the PGK promoter. Histograms in panel (h) show the distribution of ΔNGFR expression in all viable cells analysed (left), and of GFP expression in the gated (MI) ΔNGFR+ cells (right). Experiments shown are representative of at least three performed with similar results.

Figure 2:
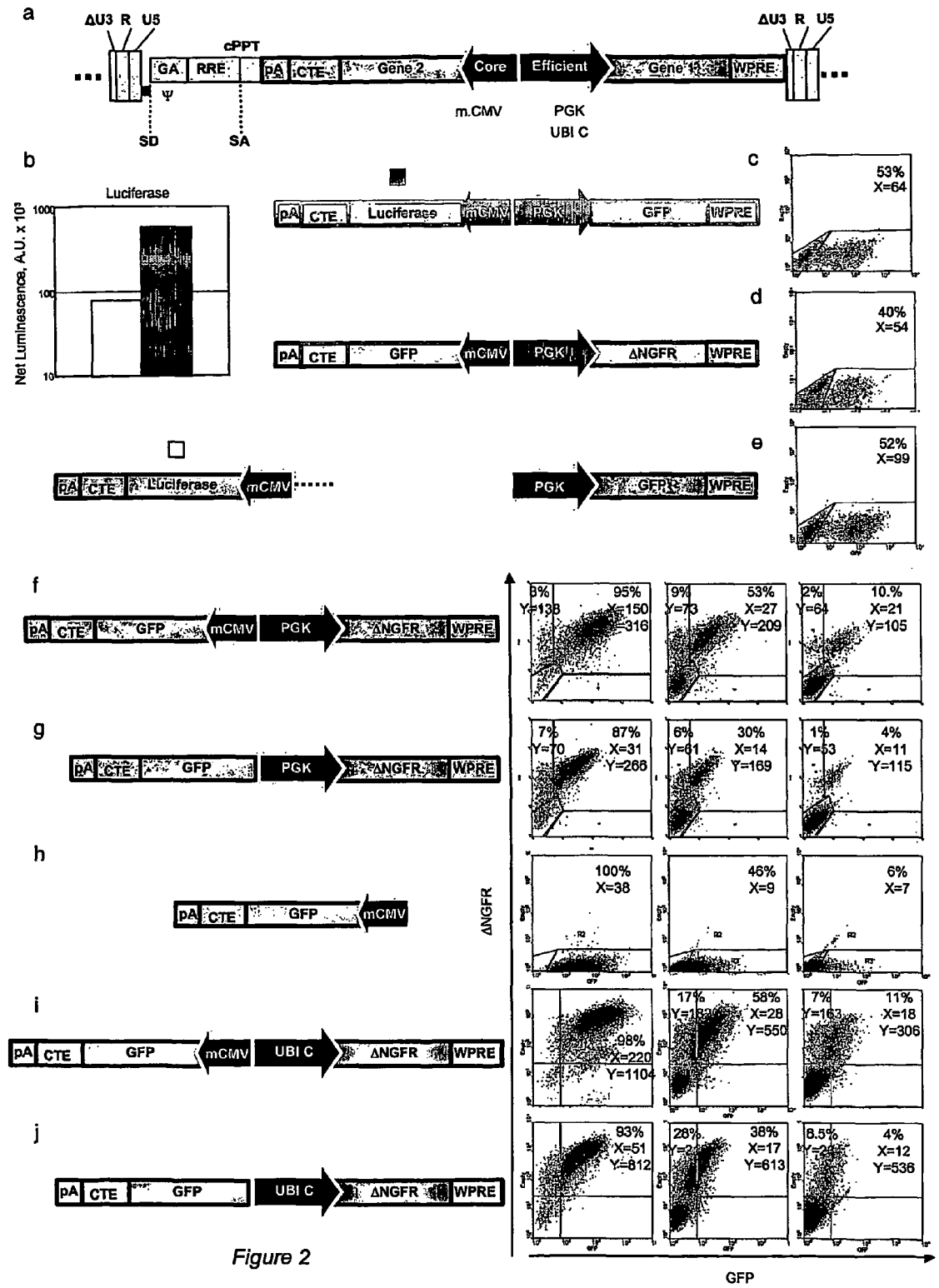

FIG. 2. Gene transfer performance of bidirectional lentiviral vectors. (a) Scheme of the proviral vector form. A bidirectional promoter made by minimal core promoter elements from the human cytomegalovirus (mCMV) joined upstream, and in opposite orientation, to an efficient promoter, derived from the human phosphoglycerate kinase (PGK) or polyubiquitin UBI-C gene, was driving divergent transcription of two RNAs. CTE, constitutive transport element from the Mason-Pfizer monkey virus; pA, polyadenylation site A from the Simian Virus 40. Other vector features as in the legend to FIG. 1. (b) Net luciferase activity and (c-e) GFP expression in HeLa cells transduced 5-7 days before with LVs carrying the indicated bi-directional or control expression cassettes. The frequency and MFI (X) of GFP+ cells at FACS analysis is indicated in the dot plots to the right. Luciferase activity was determined for the two marked vectors (□, ■). (f-j) ΔNGFR and GFP expression in HeLa cells transduced 5-7 days before with serial 10-fold dilutions of LVs carrying the indicated expression cassette. The frequency of ΔNGFR+ (upper left region) and ΔNGFR/GFP double positive (upper right region) cells, with the respective MFI of ΔNGFR (Y) and GFP (X), are indicated in the FACS dot plots. Experiments shown are representative of at least three performed with similar results.

Figure 3:
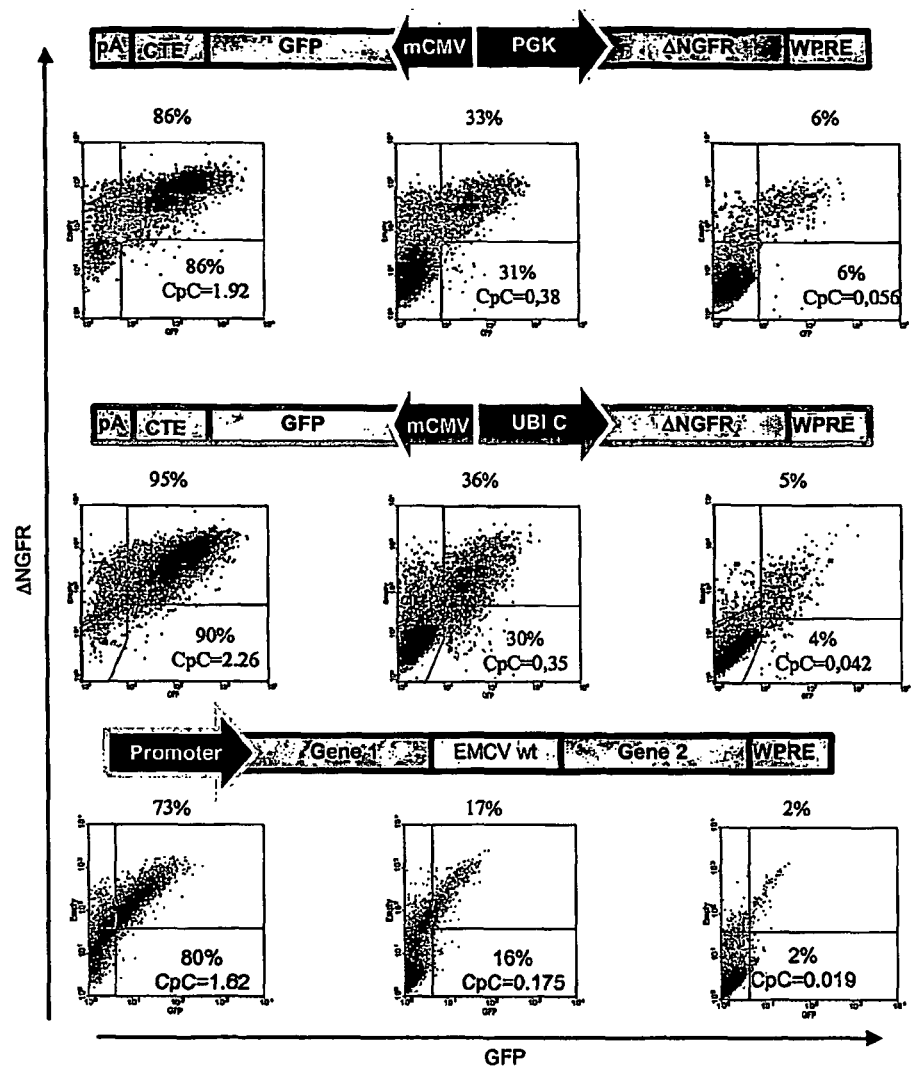

FIG. 3. Comparison of bi-directional and bicistronic lentiviral vectors performance. ΔNGFR and GFP expression in 293T cells transduced 3 weeks before with serial 10-fold dilutions of LVs carrying the indicated expression cassette. The total percentage of ΔLNGFR-expressing cells and of ΔLNGFR/GFP double positive cells (in brackets) are indicated above the FACS dot plots. The average number of vector Copies per Cell (CpC) is indicated in each plot, with the expected frequency of transduced cells according to the Poisson's distribution of random independent events. Although virtually all integrated vectors expressed ΔNGFR, its level of expression and the fraction of transduced cells co-expressing GFP were much higher for the two bi-directional vectors tested (MA1 and MA4) as compared to the EMCV wt IRES bicistronic vector.

Figure 4:
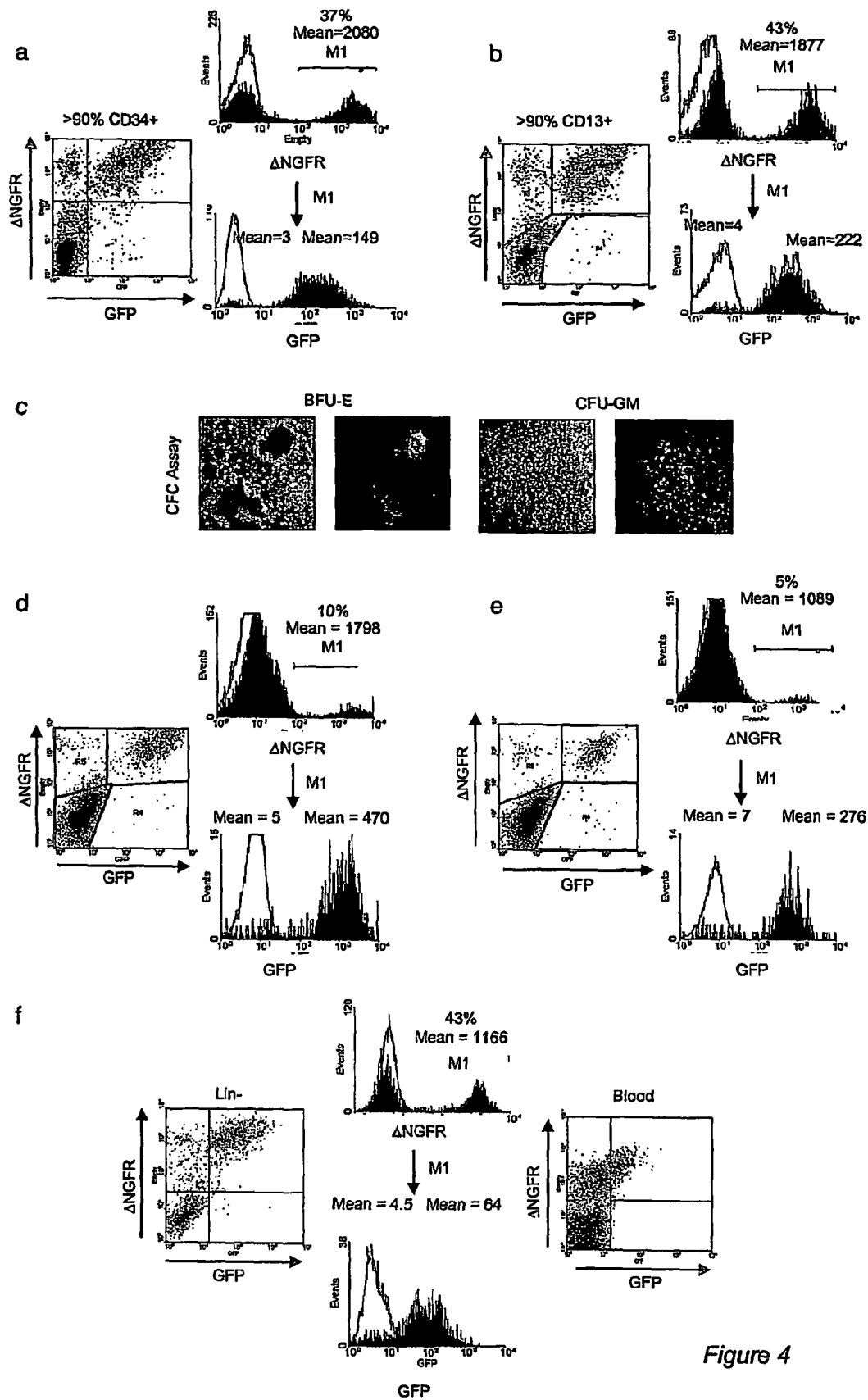

FIG. 4. Dual-gene transfer in hematopoietic cells by bi-directional vectors. (a-c) Human cord blood CD34+ progenitors were transduced by the GFP-ΔNGFR MA1 vector in the presence of early acting cytokines as described[23], and analysed either after 7 days of culture in the same medium (a), and after additional 10 days in medium promoting myeloid differentiation (b), or after seeding in methylcellulose-based clonogenic medium. For (a) and (b), a dot plot showing ΔNGFR and GFP expression by FACS analysis is shown, together with histograms showing the distribution of ΔNGFR expression in all viable cells analysed (top), and of GFP expression in the gated (M1) ΔNGFR+ cells (bottom). The percentage of immature progenitors expressing CD34, and of differentiating cells expressing the CD13 myeloid marker at the time of analysis is indicated. For (c), representative light (left) and fluorescent (right) micrograph of the indicated type of CFC are shown. (d, e) Human peripheral blood lymphocytes were transduced either after 2-day activation with anti-CD3 and anti-CD28 antibodies (d), or after 4-day treatment with interleukin-7, as described[24], (e), and analyzed for ΔNGFR and GFP expression as described above. (f, g) Purified (lin-) murine bone marrow progenitors were transduced without cytokine stimulation as described[48], and analyzed for ΔNGFR and GFP expression after 7 days in liquid culture (f), or immediately transplanted into lethally-irradiated syngenic recipients. FACS analysis of the peripheral blood of a representative mouse 2 months after transplant is shown in g. Experiments shown are representative of three performed with similar results. In d-f, cells transduced to low vector copy numbers are shown for more stringent performance analysis.

Figure 5:
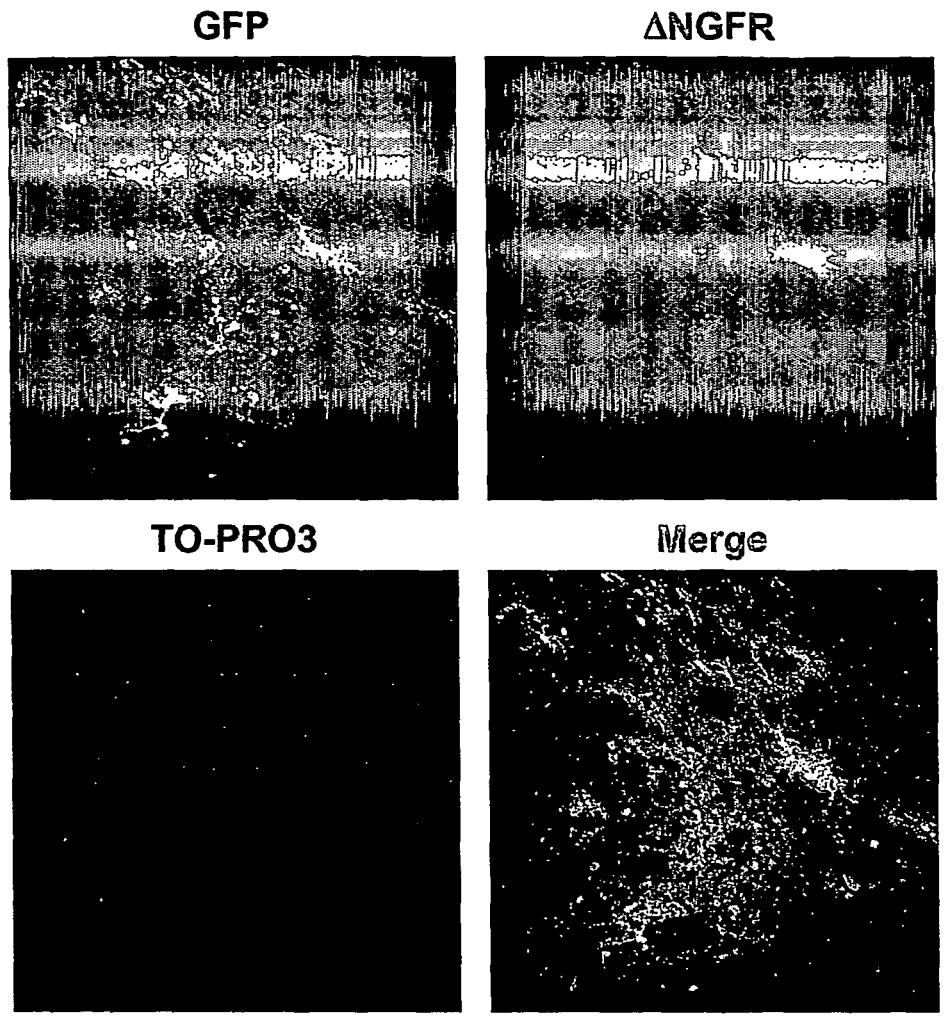

FIG. 5 In vivo dual-gene transfer by bi-directional vectors. High-titer of GFP-ΔNGFR MA1 LV were stereotactically injected into the striatum of adult mice. Cryostatic brain sections were obtained two months after injection and analyzed by immunofluorescence and confocal microscopy. Representative pictures of the injected area are shown, after immunostaining for ΔNGFR (red), GFP (green), and TO-PRO3 staining for nuclear DNA (blue). Fluorescent signals were sequentially acquired from single optical sections and are shown individually and after merging (merge). Original magnification 200× (Scale bar=120 μm)

Figure 6:
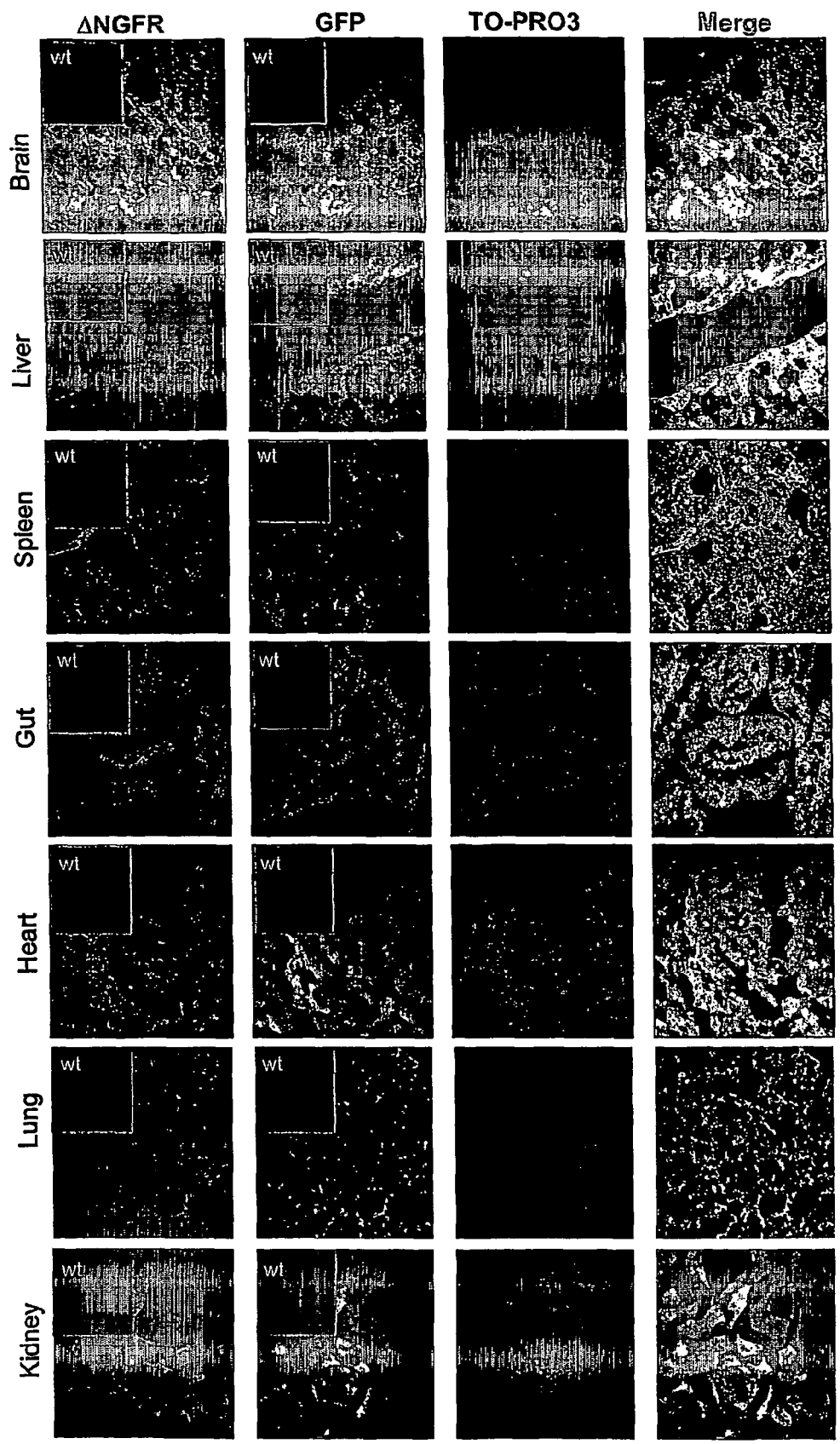

FIG. 6 Dual-transgenesis by bi-directional vector. Transgenic mouse lines were generated by direct injection of GFP-ΔNGFR MA1 LV into the perivitelline space of single-cell embryos, as described[19], and the indicated tissues were analyzed for ΔNGFR (red) and GFP (green) expression by immunofluorescence and confocal microscopy on cryostatic sections. Nuclei were stained by TO-PRO3 (blue). Fluorescent signals were sequentially acquired from single optical sections and are shown individually and after merging (merge). The pictures shown were obtained from an F1 mouse carrying two vector genomes integrated into the germ-line. Similar pictures were obtained from other transgenic mice analyzed that carried similar or higher number of vector copies. Original magnification 200× (spleen, lung), 400× (hearth, kidney, brain, liver), 630× (gut) (Scale bar=120 μm)

Figure 7A:
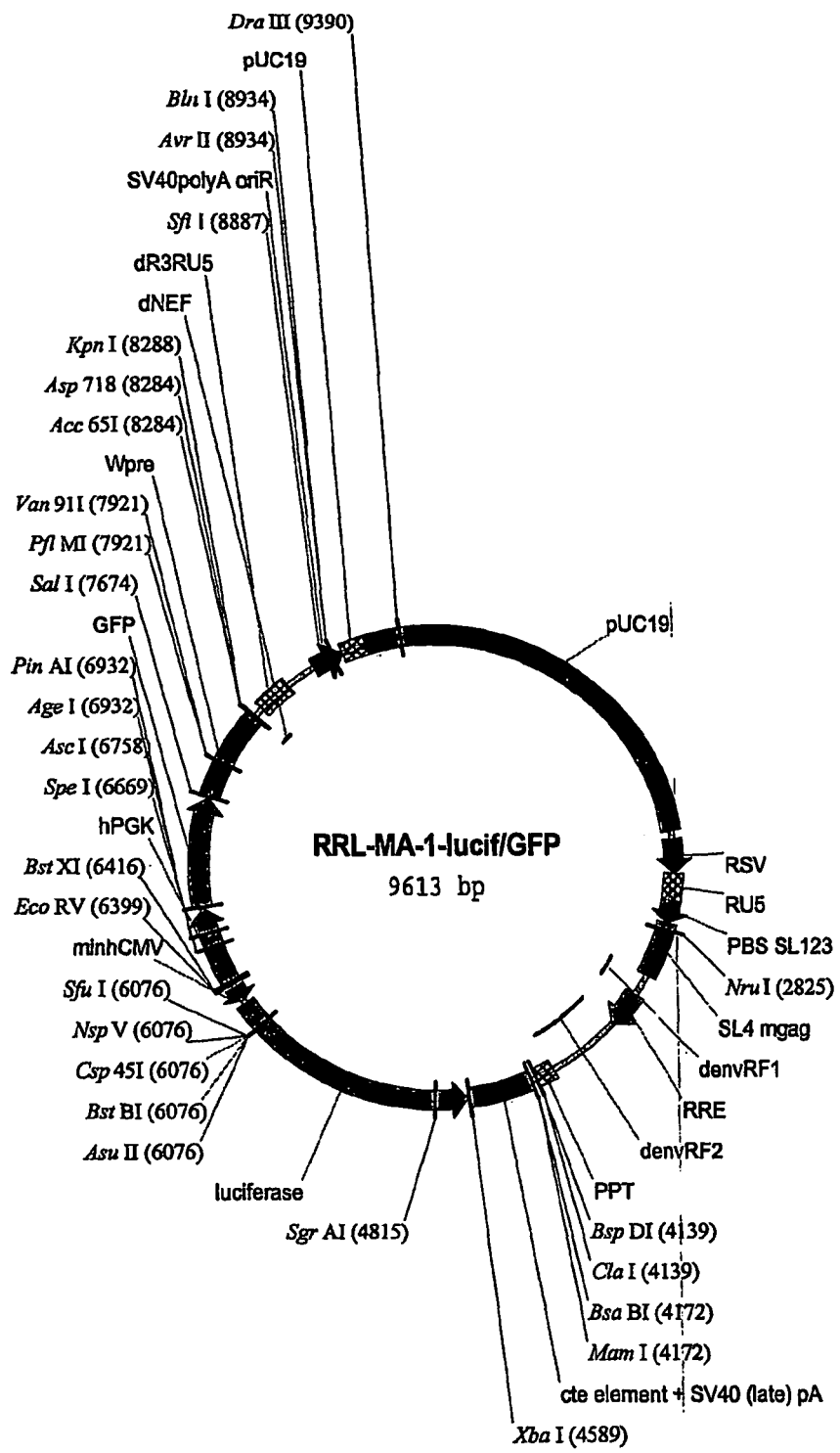

FIG. 7a Map of the plasmid containing the lentiviral vector construct RRL-MA1-lucif/GFP.

FIG. 7b Sequence of the plasmid containing the lentiviral vector construct RRL-MA1-lucif/GFP (SEQ. ID No. 4).

Figure 8A:
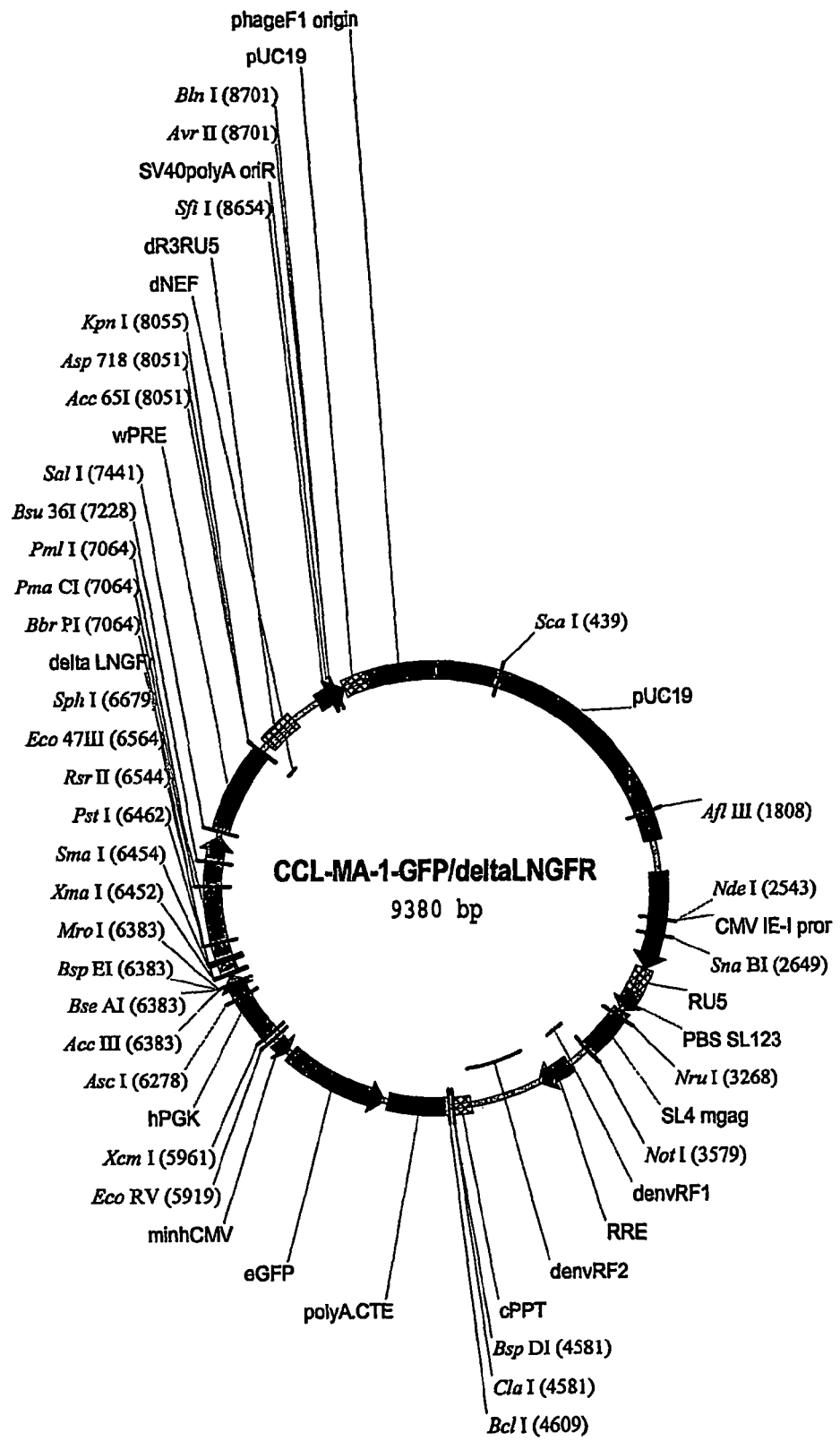

FIG. 8a Map of the plasmid containing the lentiviral vector construct CCL-MA1-GFP/deltaLNGFR.

FIG. 8b Sequence of the plasmid containing the lentiviral vector construct CCL-MA1-GFP/deltaLNGFR (SEQ. ID No. 5).

Figure 9A:
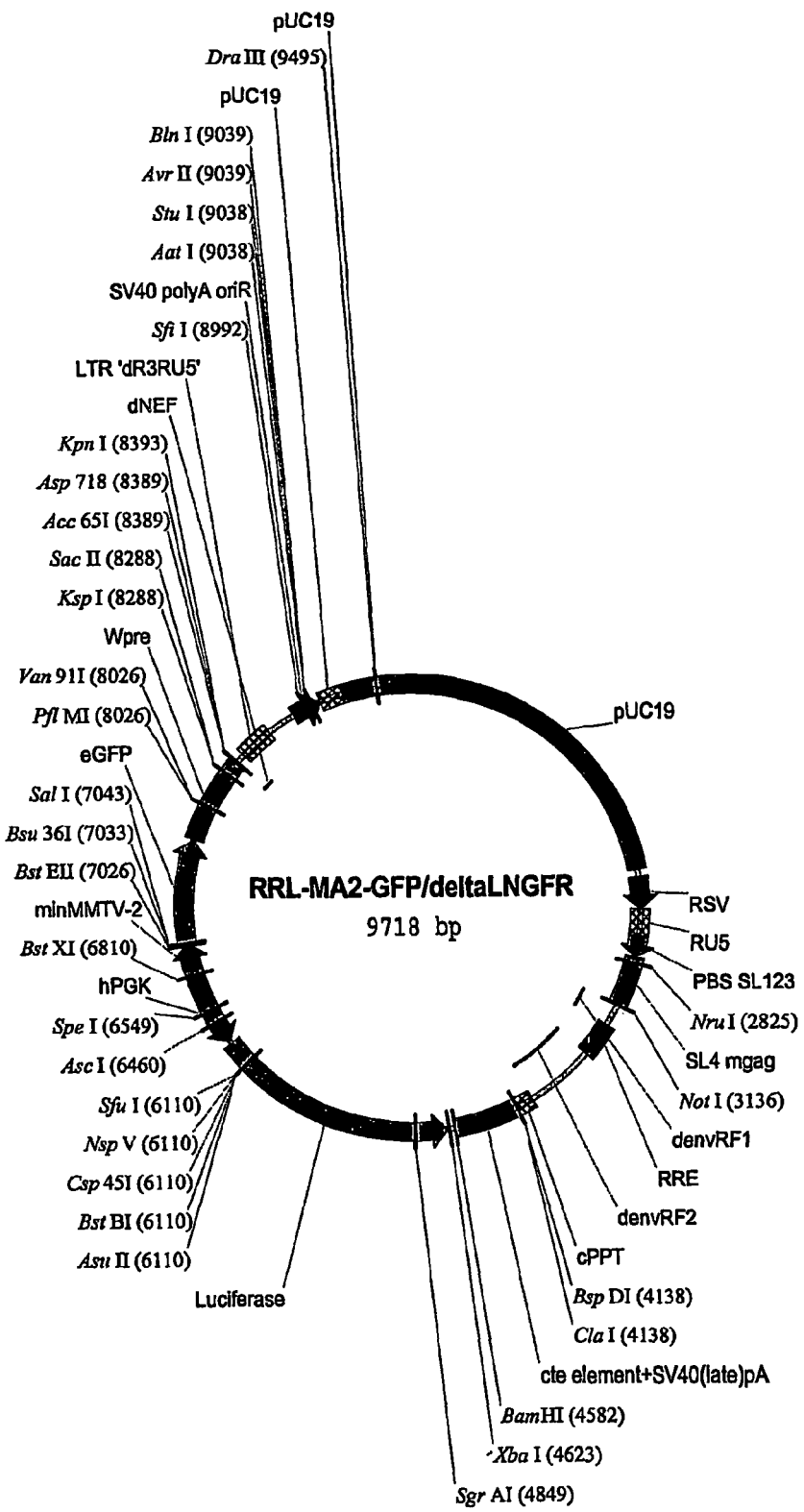

FIG. 9a Map of the plasmid containing the lentiviral vector construct RRL-MA2-lucif/GFP.

FIG. 9b Sequence of the plasmid containing the lentiviral vector construct RRL-MA2-luCif/GFP (SEQ. ID No. 6).

Figure 10A:
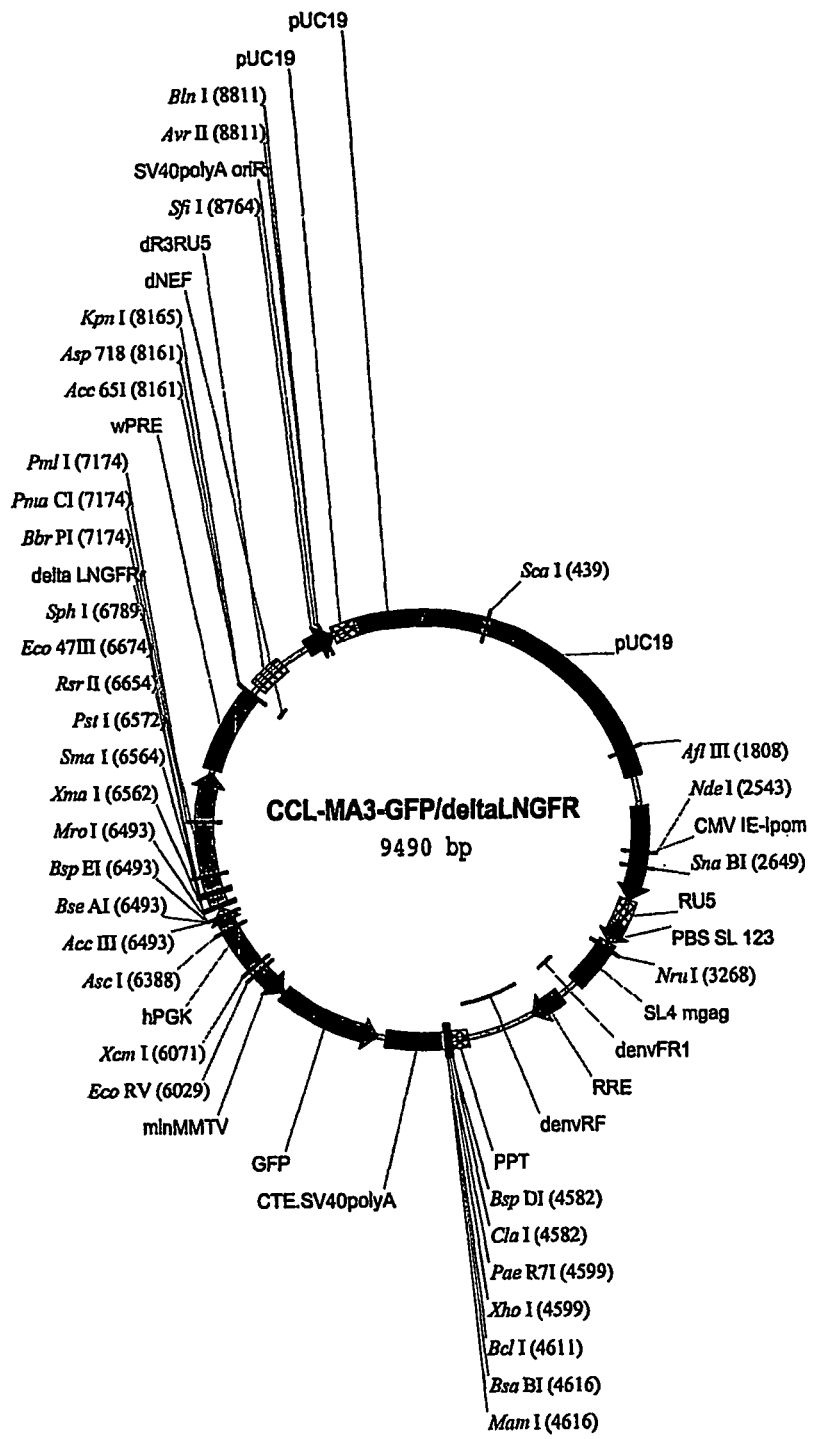

FIG. 10a Map of the plasmid containing the lentiviral vector construct CCL-MA3-GFP/deltaLNGFR.

FIG. 10b Sequence of the plasmid containing the lentiviral vector construct CCL-MA3-GFP/deltaLNGFR (SEQ. ID No. 7).

Figure 11A:
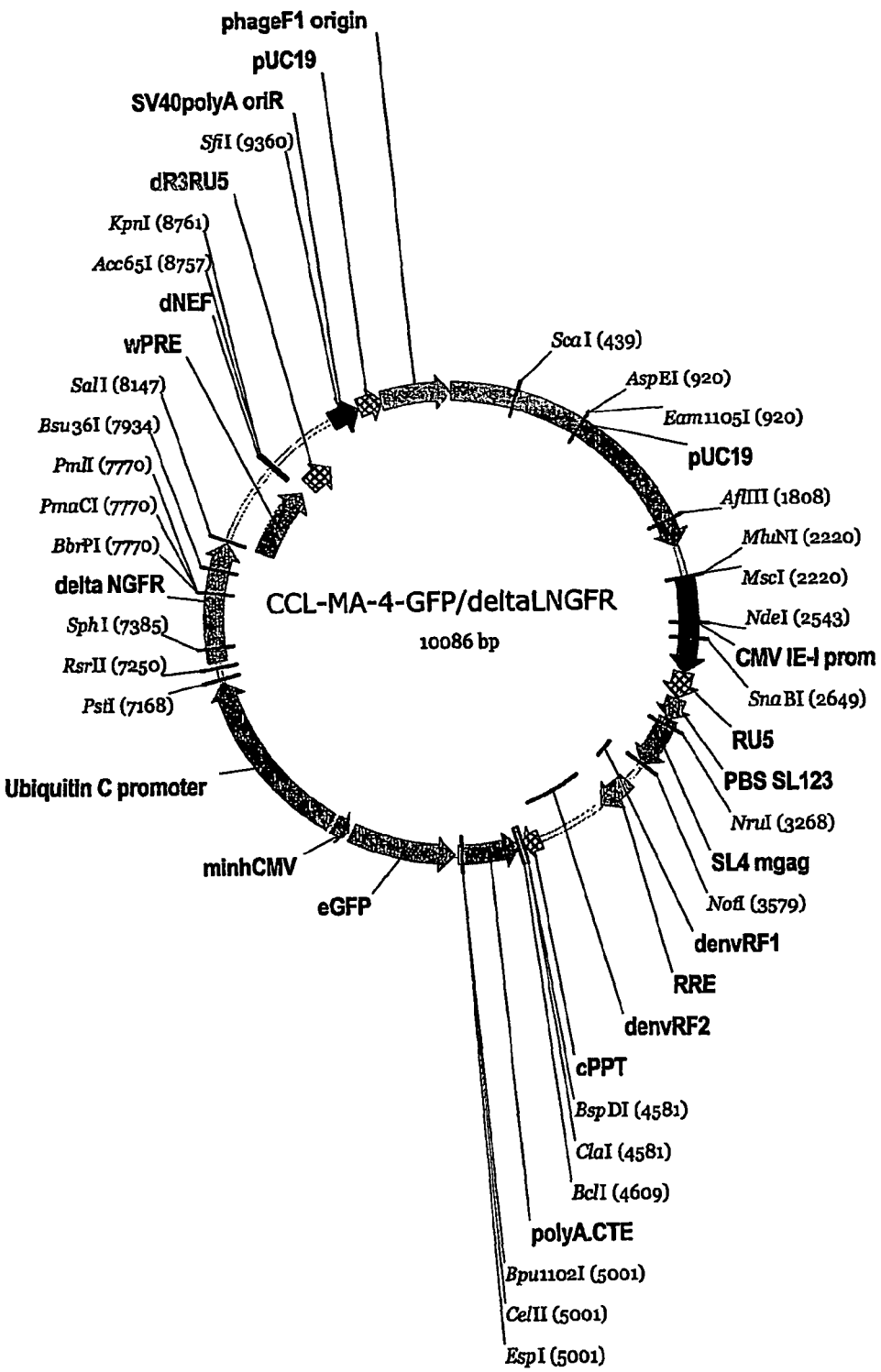

FIG. 11a Map of the plasmid containing the lentiviral vector construct CCL-MA4-GFP/deltaLNGFR.

FIG. 11b Sequence of the plasmid containing the lentiviral vector construct CCL-MA4-GFP/deltaLNGFR (SEQ. ID No. 8).

EXAMPLE 1

Materials and Methods
Plasmid Construction

All transfer vectors were built from plasmid pCCL.sin.cPPT.PGK.GFP.WPRE[15] using the following previously described sequence elements: EMCV IRES's with the downstream gene coding sequence starting at the $11^{th}$ ATG of the IRES (wt) or with the $11^{th}$ ATG of IRES mutated to create a Hindi cloning site and allow translation initiation at the downstream transgene ATG[16](EMCVmut), the NRF IRES[18], the MPMV CTE[21], a minimal CMV core promoters[20], a 1226 bp fragment from the Ubiquitin-C promoter[19].

Construction of Lentiviral Vector with Bi-directional Promoters

To generate the lentiviral construct RRL-MA1, an XhoI-XhoI fragment containing the SV40polyA.CTE.Luciferase.minhCMV elements (derived from the lentiviral construct pRRL.sin.cPPT.SV40polyA.CTE.Luciferase.minhCMV.TetO7.minMMTV.eGFP) was cloned into the lentiviral vector construct pRRL.sin.cPPT.hPGK.eGFP.Wpre (Follenzi et al., 2000) cut with the same enzyme to obtain RRL-MA1-lucif/GFP (pRRL.sin.cPPT.SV40polyA.CTE.Luciferase.minhCMV.hPGK.eGFP.Wpre). To generate the lentiviral construct CCL-MA, two fragments were cloned into the lentiviral construct pRRL.sin.cPPT.hPGK.ΔLNGFRWpre first cut with KpnI, blunted and then cut with XhoI, the first fragment containing the minhCMV.eGFP elements was derived from the lentiviral construct pRRL.sin.cPPT.SV40polyA.CTE.Luciferase.minMMTV.TetO7.minhCMV.eGFP cut with KpnI, blunted and then with XhoI and the second derived from the construct pRRL.sin.cPPT.SV40polyA.CTE.tTA2.Wpre cut with BamHI, blunted and then cut with NotI. The resulting lentiviral construct pRRL.sin.cPPT.SV40polyA.CTE.Luciferase.minMMTV.TetO7.minhCMV.eGFP was cut with NotI and AvrII and the fragment containing the cPPT.SV40polyA.CTE.eGFP.minhCMV.hPGK.ΔLNGFRWpre was cloned into the lentiviral construct pCCL.sin.cPPT.hPGK.eGFP.Wpre cut with the same enzymes to obtain CCL-MA1-GFP/ΔLNGFR (pCCL.sincPPT.SV40polyA.CTE.eGFP.minhCMV.hPGK.ΔLNGFRWpre).

To generate the lentiviral construct RRL-MA2, a HindIII-BamHI fragment containing the hPGK.Luciferase elements (derived from the lentiviral vector construct pRRL.sin.cPPT.hPGKLuciferase.IRES.Wpre) was cloned into the retroviral construct SF2-cLCM2G (obtained from Rainer Loew, University of Heidelberg, FRG) cut with the same enzymes to obtain the construct cPPT.SV40polyA.CTE.Luciferase.hPGK.minMMTV.eGFP. This construct was first cut with SalI, blunted and then cut with BamHI and the fragment containing the Luciferase.hPGK in MMTV.eGFP elements was cloned into the lentiviral vector construct pRRL.sin.cPPT.SV40polyA.CTE.tTA2.Wpre cut in the same way, to obtain RRL-MA2-lucif/GFP (pRRL.sin.cPPT.SV40polyA.CTE.Luciferase.hPGK.minMMTV.eGFP.Wpre).

To generate the lentiviral construct CCL-MA3, two fragments were cloned into the pBLKS+ cut with HindIII and XhoI, the first fragment containing the CTE.SV40polyA elements was derived from the lentiviral vector construct pRRL.sin.cPPT.SV40polyA.CTE.tTA2 cut with Hindi and XbaI and the second fragment containing the minMMTV.GFP elements derived from the construct cPPT.SV40polyA.CTE.Luciferase.hPGK.minMMTV.eGFP cut with XhoI and XbaI to obtain the construct pBLKS+ minMMTV.GFP.CTE.SV40polyA. The resulting construct was cut with EcoRV and XhoI and the fragment containing the minMMTV.GFP.CTE.SV40polyA was cloned into the lentiviral vector construct pCCL.sin.cPPT.hPGK.ΔNGFR.Wpre cut with the same enzymes, to obtain the final lentiviral vector construct CCL-MA3-GFP/ΔNGFR (pCCL.sin.cPPT.SV40polyA.CTE.GFP.minMMTV.hPGK.ΔNGFR.Wpre)

To generate the lentiviral construct CCL-MA4 the fragment derived from pHR'.UBI-C.eGFP cut with PacI, blunted and cut with PstI, containing the UBI-C promoter sequence, was inserted into the place of the PGK promoter into construct pCCL.sin.cPPT.SV40polyA.CTE.GFP.minCMV.PGK.ΔNGFR.Wpre cut with EcoRV and PstI to obtain the final lentiviral vector construct CCL-MA4-GFP/ΔNGFR (pCCL.sin.cPPT.SV40polyA.CTE.GFP.minCMV.UBI-C.Δ-NGFR.Wpre)

The maps and the nucleotide sequences of the RRL-MA1-lucif/GFP, CCL-MA1-GFP/ΔLNGFR, RRL-MA2-lucif/GFP; CCL-MA3-GFP/ΔLNGFR; CCL-MA4-GFP/ΔL-NGFR constructs are shown respectively in FIGS. 7a-11a and FIGS. 7b-11b.

Vector Production and Titration

VSV-pseudotyped third-generation LV were produced by transient 4-plasmid co-transfection into 293T cells and purified by ultracentrifugation as described[15], with the modification that 1 mM NaButyrate was added to the cultures for vector collection[47]. Expression titer of GFP or ΔLNGFR vectors were estimated on HeLa cells by limiting dilution. Vector particle was measured by HIV-1 gag p24 antigen immunocapture (NEN Life Science Products). Vector infectivity was calculated as the ratio between titer and particle for the vector expressing GFP or ΔNGFR Vector expression titer in the 293T supernatant ranged from 0.7 to $1 \times 10^7$ Transducing Units$^{HeLa}$(TU)/ml for monocistronic CMV or PGK vector, from 3 to $8 \times 10^6$ TU/ml for bicistronic vectors and bidirectional vectors. Vector infectivity ranged from 0.5 to $1 \times 10^5$ TU/ng of p24 for monocistronic CMV or PGK vector, and from 2 to $6 \times 10^4$ TU/ng of p24 for bicistronic and bi-directional vectors.

Cell Cultures

Continuous cultures of HeLa and 293T cells were maintained in Iscove's modified Dulbecco's medium (IMDM; Sigma, Milan, Italy) supplemented with 10% fetal bovine serum (FBS; Gibco, Invitrogen Corporation, UK) and a combination of penicillin-streptomycin and glutamine. Primary cultures of human umbilical vein endothelial cells HUVECs), peripheral blood lymphocytes, and cord blood CD34+ progenitors were obtained and maintained as described[15]. CD34+ progenitors were transduced with $5 \times 10^7$ TU/ml of LV and cultured for at least 7 days in the presence of recombinant human interleukin 6 (rhIL6, 20 ng/ml), recombinant human stem cell factor (rhSCF, 100 ng/ml), recombinant human FLT-3 ligand (rhFLT-3 ligand, 100 ng/ml), all from PeproTech (Rocky Hill, N.J.), and recombinant human thrombopoietin (rhTPO, 20 ng/ml; Amgen, Thousand Oaks, Calif.) as described[23]. For differentiating conditions, transduced progenitors were cultured for 10 days in the presence of rhSCF, 50 ng/ml, recombinant human granulocyte monocyte-colony stimulating factor (rhGM-CSF, 20 ng/ml), recombinant human monocyte-colony stimulating factor (rhG-CSF, 20 ng/ml), all from PeproTech. For clonogenic assays, transduced cells were plated at a density of 800 cells/ml in human complete MethoCult medium (StemCell Technologies, Vancouver, Calif.) and were scored by light and fluorescence microscopy 14 days later.

Human peripheral blood lymphocytes were purified by Ficoll gradient and transduced with $0.5-5 \times 10^7$ TU/ml of vector either after 2-day activation with 30 ng/ml anti-CD3 antibodies (Orthoclone, Milan, Italy) plus 1 µg/ml anti-CD28 antibodies (PharMingen, San Diego, Calif.), or after 4-day treatment with 5 ng/ml interleukin-7 (Boehringer Mannheim-Roche GmbH, Mannheim, Germany), as described[24].

Purification of lineage marker-negative cells from C57BL/6 mouse bone marrow with a magnetic cell depletion technique (StemCell Technologies, Vancouver, Calif.), ex vivo transduction in serum-free StemSpan medium (StemCell Technologies, Vancouver, Calif.) with $0.5-2 \times 10^7$ TU/ml of vector, and transplantation into lethally irradiated syngenic recipients were performed as described[48].

Mice

CD1, C57BL/6 and FVB mice were purchased from Charles Rivers Laboratories (Calco, Italy) and maintained in SPF conditions. All animal procedures were performed according to protocols approved by the Hospital San Raffaele Institutional Animal Care and Use Committee.

DNA analysis: Southern and Real Time PCR

Vector copies per genome were quantified by Real-Time PCR from 300 ng template DNA extracted from cells by a commercial kit (Qiagen), using one set of primers and probe to detect the LV backbone:

LV forward primer, 5'-TGAAAGCGAAAGGGAAACCA-3' (SEQ. ID No. 1);
LV reverse primer, 5'-CCGTGCGCGCTTCAG-3' (SEQ. ID No. 2);
LV probe, 5'-(VIC)-CTCTCTCGACGCAGGACT (SEQ. ID No. 3) -(TAMRA)-3'.

Reactions were carried out according to manufacturer instructions and analysed using the ABI Prism 7700 sequence detection system (PE-Applied Biosystem). For Southern blot, DNA was extracted from transduced cells, digested with Afl-II to release the expression cassette from integrated vector DNA and analysed with a WPRE probe to detect vector sequences. The average number of integrated vector copies was determined relative to a plasmid standard curve.

These numbers were used to calculate vector integration titer and normalize vector stocks for all subsequent transduction experiments to ensure similar levels of integration for each vector tested.

Experimental Design and Stereotactic Injection.

Nine weeks-old C57BL/6 mice were anesthetized with intraperitoneal injection of Tribromoethanol 1.25% (SIGMA), positioned in a stereotactic frame (David Kopf Instruments, Tujunga, Calif.) and the skull exposed by a small incision. Two µl of vector concentrate ($2\times10^6$ TU/µl) was injected by a Hamilton syringe with a 33G blunt tip needle (Hamilton, Reno, Nev.) into the left hemisphere striatum (stereotactic coordinates in mm from bregma: AP=+0.74, ML=−1.9 and DV=−3.5 from skull surface) at a rate of 0.2 µl/min. The needle was left in place for additional 5 minutes before slow removal.

Transgenesis

Transgenic mice were generated using LV as described by Lois et al.[19]. Briefly, female FVB mice were superovulated with a combination of pregnant mare serum and human chorionic gonadotropin. On average between 20 and 30 embryos were collected per female and microinjected into the perivitelline space with 10-100 pL of $5\times10^7$ TU/ml LV stock on the same day. Manipulated embryos were immediately implanted into the oviduct of pseudopregnant CD1 mice. Pups were genotyped for the presence of the GFP sequence by PCR analysis as described[49]. Positive mice were bred to test germ-line trasmission of the transgene. DNA was extracted from the tail and used to quantify vector copy number by real time PCR in founder and F1 progeny mice.

Flow Cytometry and Luciferase Assay

Transduced cells were grown for at least 4 days before FACS analysis to reach steady state GFP expression and to rule out pseudotransduction. Before FACS analysis, adherent cells were detached with 0.05% trypsin-EDTA, washed, and fixed in phosphate buffer saline (PBS) containing 1% paraformaldehyde (PAF) and 2% FBS. Cells grown in suspension were washed and resuspended in PBS containing 2 µg/ml propidium iodide (PI) (BD Bioscience PharMingen, San Diego, Calif.) and 2% FBS. For immunostaining, $10^5$ cells were blocked in PBS 5% mouse serum, 5% human serum, 2% FBS for 15 min at 4° C. After blocking, 10 µl of R-phycoerythrin (RPE)-conjugated antibodies (anti-CD34 and anti-CD13, Dako, Glostrup, Denmark, and anti-ΔLNGFR, BD Bioscience PharMingen, San Diego, Calif.) were added and the cells were incubated for 30 min at 4° C., washed, stained with PI, and analyzed by three-color flow cytometry. Only viable, PI-negative cells were used for the analysis. Luciferase was assayed in cell lysates prepared as described by the manufacturer (luciferase assay system, Promega). RLU were measured with a Lumat LB9507 luminometer (Berthold) after mixing cell lysates (normalized for protein content measured by BCA Protein Assay Reagent kit Pierce) with Luciferase Substrate (Promega).

Tissue Analysis

Anesthetized mice were perfused with 0.9% NaCl followed by 4% PAF in PBS. Tissue samples were collected, equilibrated in 20% sucrose in PBS for 48 h at 4° C., and embedded in optimal-cutting-temperature compound (OCT) for quick freezing. 10 µm (for transgenic mice) and 20 µm (for stereotactic injected mice) thick cryostatic sections were post-fixed in PAF and frozen at −80° C. Sections were blocked with 5% goat serum (Vector Laboratories) in PBS containing 1% bovine serum albumine (BSA) and 0.1% Triton X-100 (PBS-T), and incubated with rabbit affinity-purified GFP antibody (Molecular Probes) and R-phycoerythrin (RPE)-conjugated ΔLNGFR monoclonal antibody (BD Bioscience PharMingen, San Diego, Calif.) for 1 h, washed and stained with AlexaFluor488-conjugated goat anti-rabbit antibody (Molecular Probes) in PBS-T and 1% BSA for 1 h. Cell nuclei were stained with TOPRO-3 after 1 h of RNAse treatment (Molecular Probes). Sections were mounted and analyzed by three-laser confocal microscope (Radiance 2100; BioRad). Fluorescent signals from single optical sections were sequentially acquired and analyzed by PhotoShop 7.0 (Adobe).

Results

Bicistronic LVs

In order to express more than one transgene from a single vector, the authors first evaluated the performance of different IRES's in the context of late-generation self-inactivating LVs[15]. They used the strong CMV and PGK promoters to drive expression of bicistronic transcripts encoding, from the 5' to the 3' end, the luciferase reporter, an IRES, and the cell-associated GFP marker (FIG. 1a). Two IRES's were derived from the Encephalomyocarditis virus; a wild-type (EMCVwt) and a mutant (EMCVmut) form[16, 17], that differed for the ATG from which downstream translation started. Another IRES was derived from the 5' untranslated sequence of the NF-kB transcription Repressing Factor (NRF) mRNA[18].

They generated high-titer VSV-pseudotyped stocks of all bicistronic and control monocistronic vectors, and normalized them for transducing activity measuring integration in HeLa cells by Southern blot (FIG. 1b). They then compared gene expression in cells transduced to equal vector copy numbers (FIG. 1c-f). Although luciferase activity was similar in HeLa cells transduced by CMV-luciferase vector and in cells transduced by the best performing bicistronic vector, only a small fraction of the latter cells expressed the IRES-dependent GFP gene, with a ten-fold decrease in expression titer as compared to cells transduced by the control CMV-GFP vector (FIG. 1c). Moreover, the GFP mean fluorescence intensity (MFI) was significantly lower in cells expressing the protein from the IRES's than in cells expressing it from the $^{mRNA}$Cap. They then tested bicistronic LVs in primary human cells, including umbilical vein endothelial cells, peripheral blood lymphocytes, and CD34+ cord blood hematopoietic progenitors (HPC) (FIG. 1d-f). All cell types were transduced efficiently, as indicated by the frequency of GFP-positive cells in cultures transduced by control CMV-GFP vector, but IRES-dependent GFP expression was only observed in a fraction of cells transduced by bicistronic vectors. IRES activity varied extensively with the target cell type; the NRF IRES was the only one reaching detectable downstream gene expression in lymphocytes, while the EMCVwt IRES was the most efficient in the other cell types. In addition, all IRES's decreased, in some cases more than one log, upstream gene expression, as compared to the control CMV-luciferase vector.

They also evaluated IRES-based vectors by expressing two cell-associated markers, GFP and a truncated version of the low-affinity NGF receptor (ΔLNGFR) (FIG. 1g,h). Among HeLa cells transduced by a low dose of the best-performing bicistronic vector, only the cells expressing high levels of ΔLNGFR also expressed GFP, with an average of one out of four ΔNGFR-positive cells expressing GFP to detectable levels (FIG. 1g). Similarly, only a small fraction of transduced CD34+ progenitors expressing ΔNGFR also expressed GFP to detectable levels (FIG. 1h). Overall, these results indicated that IRES-based bicistronic vectors failed to ensure coordinate expression of two transgenes in most target cell types tested, and that multi-copy transduction or selection of transduced cells for downstream gene expression were required to obtain a population expressing both transgenes in the majority of cells.

Bidirectional LVs

To overcome the limitations of bicistronic vectors, the authors explored a new promoter design for coordinate transgene expression. They joined a minimal core promoter upstream, and in opposite orientation, to an efficient promoter. Rationale of this design was that upstream elements in the efficient promoter, when closely flanked by core promoters on both sides, may drive transcriptional activity in both directions. If such bi-directional activation occurred, expression of both transcripts would be coordinately regulated. They tested two ubiquitously expressed promoters, previously shown to drive robust and efficient transgene expression in LV; the above mentioned 516 bp fragment from the human phosphoglycerate kinase promoter (PGK)[15] and a 1226 bp fragment from the human ubiquitin C promoter (UBI C)[19]. They joined them to a minimal core promoter derived from the cytomegalovirus (minCMV) that was previously developed to couple initiation of eukaryotic transcription to tetracycline (Tc)-dependent operators[20]. They flanked the bi-directional promoter with two expression cassettes optimized for LV-mediated gene delivery (FIG. 2a). The upstream cassette—in anti-sense orientation relative to the vector LTR—included the constitutive transport element (CTE) of the Mason-Pfizer virus[21], and a polyadenylation site from the Simian Virus 40 (SV40). The downstream cassette included the woodchuck hepatitis virus post-transcriptional regulatory element (WPRE)[22] and the SIN HIV-1 LTR polyadenylation site.

As described above for bicistronic LVs, they verified correct transfer and normalized transduction of each vector by Southern blot analysis and real-time PCR of transduced cells. LV carrying bi-directional expression cassettes were produced to high titer and infectivity, similar to those obtained with standard vectors (see Methods). The bi-directional design significantly enhanced transcription from the upstream minimal promoter without affecting downstream expression from the efficient promoter (FIG. 2b-h). Luciferase expression from the minCMV promoter, for instance, was increased at least one log when fused upstream to the PGK promoter (FIG. 2b). Remarkably, the bi-directional PGK promoter allowed detecting GFF (or ΔLNGFR, not shown) to the same frequency and to similar expression levels in cells transduced by the bi-directional vector and expressing the protein from either side of the promoter (FIG. 2c,d), as in cells transduced by the control PGK vector (FIG. 2e). Using two cell-associated markers, ΔLNGFR and GFP, they showed stable, efficient and coordinate expression of bi-directional LVs, both at high and low vector copy number (FIG. 2f). At high vector input, they reached high-level expression of both transgenes in virtually every target cell. At low vector input, when most transduced cells carried one proviral copy, they showed transgene co-expression in virtually every labeled cell, indicating the occurrence of divergent transcription from the bi-directional promoter. In both conditions, transgene expression was maintained to similar levels in cells analyzed at early and late times post-transduction (not shown, and FIG. 3 below). Transgene-expressing cells tended to distribute along a diagonal line in the two-color FACS plot, indicating that expression of the two transgenes was coordinately regulated.

Intriguingly, they observed coordinate bi-directional expression, although to significantly lower efficiency on the upstream side than the downstream side, when they tested the sole PGK promoter in the context of the bi-directional expression cassette that they developed (FIG. 2g). They reproduced this finding after swapping the position of the two transgenes on each sides of the PGK promoter (not shown). These results indicated that transcription-activating elements in the PGK promoter are intrinsically capable of triggering divergent transcription and thus provide the main driving force for dual-gene expression in the new LV, ensuring coordinate regulation of transcription on both sides of the bi-directional promoter. Apposition of the minCMV core promoter, which had a very low activity per se (FIG. 2h, and 2b above), enhanced upstream transcription from the PGK promoter possibly because of more efficient initiation (compare FIGS. 2g and 2f). When they changed the driving promoter in bi-directional vectors from PGK to UBI-C, they reproduced the findings observed with the PGK promoter (FIG. 2i). They revealed an intrinsic bi-directional activity of the UBI-C promoter (FIG. 2j) that was significantly enhanced by the upstream addition of the minCMV promoter.

They then compared directly the performance of bi-directional and bicistronic vectors in relation to the number of integrated copies, as measured by real-time PCR (FIG. 3). By analyzing 293T cells transduced with increasing vector doses, they proved that the vast majority of integrated bi-directional vectors based on the PGK (MA1) or UBI-C (MA4) promoter efficiently expressed both transgenes, clearly outperforming the best IRES-based bicistronic vector.

Ex Vivo and In Vivo Dual-Gene Transfer

They then assessed the performance of the bi-directional MA1 LV in more relevant targets for gene therapy applications and by different delivery strategies. They transduced human cord-blood HPC and PBL with ΔLNGFR-GFP MA1 LV ex vivo, according to previously optimized protocols[23, 24] (FIG. 4). Both gene products were coordinately expressed to high-levels in a large fraction of HPC scored both as immature cells grown in the presence of early-acting cytokines (FIG. 4a), and after differentiation in liquid culture (FIG. 4b) or clonogenic assay (FIG. 4c, GFP only). Similarly, they obtained coordinate ΔLNGFR and GFP expression in PBL transduced in standard conditions of proliferation, triggered by CD3/CD28 co-stimulation (FIG. 4d), and as non-proliferating cells, treated only with IL-7 to maintain naïve cell properties (FIG. 4e). They also performed transplantation studies with transduced murine HPC, enriched from the bone marrow by negative selection, to prove stable dual-transgene expression in the progeny of long-term repopulating HSC (FIG. 4f). ΔLNGFR and GFP were coordinately expressed to similar levels in the ex vivo transduced cells, before transplantation, and in the white blood cells of long-term engrafted mice. Overall, these results validated the new LV for proficient dual gene transfer in primitive, committed, and differentiated hematopoietic cells.

They injected concentrated ΔLNGFR-GFP MA1 LV in the striatum of adult mice and scored transgene expression 4 weeks after injection by confocal microscopy of brain sections immuno-stained for GFP and ΔLNGFR (FIG. 5). They observed robust co-expression of both transgenes in the brain tissue surrounding the injection site. As previously reported after striatal injection of VSV-pseudotyped LV[25-27], the vast majority of cells expressing the markers had the typical morphology of striatal neurons. Thus, the new bi-directional LV enabled efficient in vivo dual-gene transfer.

Dual-Transgenesis

They evaluated whether the new bi-directional LV allowed generation of dual-transgenic mouse lines. As previously described by Lois et al[19], they microinjected the ΔNGFR-GFP LV into the perivitelline space of single-cell embryos, and implanted them into pseudopregnant females. We obtained transgenic mice to high frequency, as assessed by the presence of vector DNA (more than 50% of newborns), and proved vector integration in the germ line by crossing some founder mice and analyzing their progeny for vector DNA content and transgene expression (FIG. 6). In the two F1 mice analyzed, carrying 2 and 5 vector copies in the genome, they found remarkably consistent expression of both transgenes in virtually every cell in the tissues studied, which included brain, liver, spleen, gut, heart, skeletal muscle, and kidney. Vector expression was also well detectable in the bone marrow and peripheral blood of the same mice, although in less than 100% of the cells, and more clearly for ΔNGFR than GFP (not shown). These data indicated that bi-directional LV transgenesis is a rapid and efficient method to obtain robust, stable and coordinate expression of two transgenes in genetically-engineered mice. In addition, they show that the minCMV-PGK bi-directional promoter that they developed governs dual transgene expression in the majority of differentiated tissues of the mouse, and maintains expression after inheritance through the germ-line.

Discussion

In the pursuit of strategies enabling efficient dual-gene transfer, they initially faced significant limitations of IRES-based approaches. When tested in the context of bicistronic LV, IRES-dependent gene expression was significantly lower than that dependent on the $^{mRNA}$Cap, and required multi-copy transduction to co-express the downstream gene in a sizable fraction of transduced cells. In addition, IRES's decreased expression of the upstream gene in the transcript, and displayed significant cell type-dependent variation in activity. Similar limitations have been reported when incorporating IRES's into other types of gene transfer vectors[14, 28-32]. Thus, selection for downstream gene expression is likely to be required when using IRES to ensure co-expression in all target cells. Although selection protocols are compatible with some ex vivo gene transfer and therapy applications, they may adversely affect the biological properties of gene-corrected cells, in particular when selectable marker expression is inefficient. In fact, prolonged ex vivo culture and a limited size or clonal composition of the transduced cell population may reduce engraftment, long-term survival and tissue repopulation after transplantation[33]. Even more important, the inefficiency of IRES-dependent expression prevents most application of bicistronic vectors to direct in vivo gene transfer. Thus, authors explored novel strategies to take full advantage of gene transfer systems, such as LV, that allow efficient ex vivo transduction and direct in vivo administration[34].

They have developed a new promoter design based on the juxtaposition of core promoter elements upstream, and in opposite orientation, to an efficient promoter. The bi-directional assembly drove divergent transcription, indicating that upstream enhancer/promoter elements within the efficient promoter were capable of promoting transcription in an orientation-independent manner and from both sides simultaneously. Upon incorporation of these promoters into LV, they reached efficient dual-gene transfer and coordinate expression in continuous cell lines and primary cells ex vivo. Because both transgenes were expressed in the vast majority of transduced cells, they did not need to select cells to ensure transgene co-expression. Upon direct injection of bi-directional LV into the CNS, the authors showed coordinate expression of two transgenes in neural cells in vivo. In addition, bi-directional LV allowed robust dual transgenesis, leading to pan-cellular expression of both transgenes in all tissues examined. All these results could not be reached until now using currently available technologies.

By monitoring transduced cells carrying a single vector copy, authors proved that divergent transcription occurred from a single bi-directional promoter, that expression of both transgenes was functionally linked and coordinately regulated, and that bi-directional promoters were consistently active in all types of target cells tested, without being silenced or randomly fixed in one direction of transcription, even after cellular differentiation. Although they did not map how close the two opposite core promoters must be for operational linkage, they may expect that close juxtaposition of the fused minimal core promoter to some of the upstream elements in the efficient promoter, as observed in natural promoters between core and upstream elements, may be required. Both the PGK and UBI-C promoters tested in this work drove divergent transcription when fused to a minimal core promoter in the opposite orientation. Intriguingly, both of these promoters were shown to be intrinsically capable of promoting divergent transcription, although to lower efficiency on the upstream than the downstream side, when incorporated into the bi-directional expression cassette that they developed. This surprising observation may indicate a specific feature of a class of ubiquitously-expressed housekeeping promoters, possibly related to their content of CpG islands (see below and[35-37]). However, they should not forget that both the promoter placement between two efficient expression cassettes endowed with post-transcriptional regulatory elements enhancing translation, and LV-mediated integration, which has been shown to preferentially target transcribed genes in the chromatin, may contribute to unravel latent transcriptional activity. Although the intrinsic bi-directional activity of the housekeeping promoters tested may not be efficient enough for exploitation per se, without the upstream assembly of core promoter elements described in this work, it provides the basis for the coordinate regulation of dual-gene expression reached by our new vectors. On the other hand, the propensity of these promoters to drive divergent transcription should be kept in mind when engineering vectors and analyzing transduced cells or tissues[38], and may provide a possible mechanism for the frequently observed interference between nearby promoters in the same vector construct[10, 39]. It is possible that the bi-directional design described here may be successfully applied to tissue-specific promoters to obtain coordinated expression of two transgenes in specific tissues. In addition, by combining bi-directional promoters with bicistronic transcripts one could express more than two transgenes within the same cell, although with the limitations described above for IRES-dependent vectors. Inducible bi-directional promoters were originally developed in Tet-regulated expression systems, by duplicating a minimal promoter on both sides of a series of Tet operator repeats, to obtain exogenously regulated expression of two transgenes[36, 40, 41]. This design was recently applied to other systems that also combine prokaryotic enhancer elements with chimeric trans-activators to regulate gene expression. Although these inducible expression systems represent powerful tools for gene-function studies, they are dependent on co-expression and functional activity of protein trans-activators, and pose several challenges when applied to vector-based delivery and in vivo applications. A constitutive bi-directional promoter was recently tested for exogenous gene expression in plant biotechnology[43]. Our results provide the first description of synthetic bi-directional promoters that exploit the endogenous transcriptional machinery available to most animal cell types to drive robust and constitutive expression of two divergent transcripts. In nature, few instances of bi-directional promoters had been documented until recently. Intriguingly, a recent survey of the human genome indicated an abundance of divergently transcribed gene pairs, whose transcription start sites are separated by less than 1 kb[44, 45]. It is likely that many of the promoter elements found between these gene pairs can initiate transcription in both directions, and contain shared elements that regulate both genes[46]. Thus, the synthetic bi-directional promoters that they have developed may mimic a well-represented and evolutionary conserved feature of eukaryotic transcription, providing a structural basis for their robust performance. The new lentiviral vectors built around these bi-directional promoters will likely advance the reach and the safety of gene therapy, the power of gene-function and target validation studies, and the applications of animal transgenesis. If adapted for the expression of short interfering RNA, they may also enable coordinate knock-down of multiple genes.

References

1. Kay, M. A., Glorioso, J. C. & Naldini, L. *Nat Med* 7, 33-40 (2001).
2. Neff, T. et al. *J Clin Invest* 112, 1581-1588 (2003).
3. Bordignon, C. & Roncarolo, M. G. *Nat. Immunol.* 3, 318-321 (2002).
4. Sadelain, M. *J Gene Med* 4, 113-121 (2002).
5. Bonini, C. et al. *Science* 276, 1719-1724 (1997).
6. Hacein-Bey-Abina, S. et al. *Science* 302, 415-419 (2003).
7. Burton, E. A., Glorioso, J. C. & Fink, D. *J Gene Ther* 10, 1721-1727 (2003).
8. Sadelain, M., Riviere, I. & Brentjens, R. *Nat Rev Cancer* 3, 35-45 (2003).
9. Miller, A. D. in Retrovinses. (eds. J. Coffin, S. H. Hughes & H. E. Varmus) 437-474 (Cold Spring Harbor Laboratory Press, Plainview; 2000).
10. Emerman, M. & Temin, H. M. *Mol Cell Biol* 6, 792-800 (1986).
11. Zhu, Y., et al. *Mol. Ther.* 4, 375-382 (2001).
12. Klump, H. et al. *Gene Ther.* 8, 811-817 (2001).
13. Furler, S., et al. *Gene Ther* 8, 864-873 (2001).
14. Marfinez-Salas, E. *Curr. Opin. Biotechnol.* 10, 458-464 (1999).
15. Follenzi, A., et al. *Nat Genet* 25, 217-222 (2000).
16. Ghattas, I. R., Sanes, J. R. & Majors, J. E. *Mol. Cell Biol.* 11, 5848-5859 (1991).
17. Qiao, J., et al. *Hum Gene Ther* 13, 881-887 (2002).
18. Oumard, A., et al. 20, 2755-2759 (2000).
19. Lois, C., et al. *Science* 295, 868-872 (2002).
20. Baron, U. & Bujard, H. *Methods Enzymol.* 327, 401-421 (2000).
21. Bray, M. et al. *Proc Natl Acad Sci USA* 91, 1256-1260 (1994).
22. Zufferey, R., et al. *J. Virol.* 73, 2886-2892 (1999).
23. Ailles, L. et al. *Mol Ther* 6, 615-626 (2002).
24. Cavalieri, S. et al. *Blood* 102, 497-505 (2003).
25. Naldini, L., et al. *Proc Natl Acad Sci U S A* 93, 11382-11388 (1996).
26. Baekelandt, V. et al. *Hum Gene Ther* 13, 841-853 (2002).
27. Degion, N. et al. *Hum. Gene Ther.* 11, 179-190 (2000).
28. Sokolic, R. A. et al. *Blood* 87, 42-50 (1996).
29. Wong, E. T., Ngoi, S. M. & Lee, C. G. *Gene Ther* 9, 337-344 (2002).
30. Kozak, M. *Gene* 318, 1-23 (2003).
31. Mizuguchi, H., et al. *Mol Ther* 1, 376-382 (2000).
32. Hennecke, M. et al. *Nucleic Acids Res* 29, 3327-3334 (2001).
33. Mazurier, F., et al. *Blood* 103, 545-552 (2004).
34. Vigna, E. & Naldini, L. *J Gene Med* 2, 308-316 (2000).
35. Gardiner-Garden, M. & Frommer, M. *J Mol Biol* 196, 261-282 (1987).
36. Lavia, P., Macleod, D. & Bird, A. *EMBO J.* 6, 2773-2779 (1987).
37. Johnson, P. & Friedmann, T. *Gene* 88, 207-213 (1990).
38. Scacheri, P. C. et al. *Genesis* 30, 259-263 (2001).
39. Vigna, E. et al. *Mol Ther* 5, 252-261 (2002).
40. Baron, U., et al. *Nucleic. Acids. Res.* 23, 3605-3606 (1995).
41. Unsinger, J., et al. *Mol Ther* 4, 484489 (2001).
42. Fux, C. et al. *J Gene Med* 5, 1067-1079 (2003).
43. Xie, M., He, Y. & Gan, S *Nat Biotechnol* 19, 677-679 (2001).
44. Trinklein, N. D. et al. *Genome Res* 14, 62-66 (2004).
45. Takai, D. & Jones, P. A. *Mol Biol Evol* 21, 463467 (2004).
46. Adachi, N. & Lieber, M. R. *Cell* 109, 807-809 (2002).
47. Farson, D. et al. *Hum Gene Ther* 12, 981-997 (2001).
48. De Palma, M., et al. *Nat Med* 9, 789-795 (2003).
49. Follenzi, A., et al. *Hum Gene Ther* 13, 243-260 (2002).

The invention claimed is:

1. A synthetic bidirectional promoter for expression of at least two coding sequences in opposite direction in animal cells comprising 5' end to 3' end:
   a) a first minimal promoter sequence of cytomegalovirus (CMV) or mouse mammary tumor virus (MMTV) genomes;
   b) a promoter sequence of an animal gene comprising an enhancer region and a second minimal promoter sequence;
   the promoter sequences a) and b) driving a coordinate transcription of at least two coding sequences in the opposite orientation, and
   wherein the synthetic bidirectional promoter is endogenously regulated.

2. The bidirectional promoter according to claim 1 wherein the animal gene is a ubiquitously expressed gene comprising the phosphoglycerate kinase gene or the ubiquitin gene.

3. A bidirectional expression cassette comprising the bidirectional promoter according to claim 1, insertion sites positioned downstream to each of the promoter sequences a) and b), and polyadenylation sites positioned downstream to each of the insertion sites, wherein at least one transcriptional regulatory element is positioned upstream to one or each of the polyadenylation sites.

4. The bidirectional expression cassette according to claim 3 further comprising at least one internal ribosome entry site (IRES) sequence to express three or more genes.

5. An expression construct containing the bidirectional promoter according to claim 1.

6. An expression construct containing the bidirectional expression cassette according to claim 3.

7. A gene transfer expression vector containing the expression construct according to claim 5 further comprising lentiviral or retroviral sequences.

8. A method for the delivery and expression of multiple genes in animal cells comprising transforming the animal cells ex vivo with the gene transfer vector according to claim 7; and expressing the genes ex vivo.

9. The method according to claim 8 wherein the animal cells are tissue animal cells.

10. The method according to claim 9 wherein the tissue animal cells are brain neurons.

11. A method for the coordinate expression of two exogeneous coding sequences in an animal cell comprising the following steps:

a) cloning two exogeneous coding sequences into the gene transfer expression vector according to claim 7, each coding sequence under the control of one of the promoter sequences a) and b) of the bidirectional promoter:

b) transforming animal cells with the cloned vector; and c) expressing the cloned vector.

12. The method for the coordinate expression of two exogeneous coding sequences according to claim 11 wherein the animal cell is a human cell.

13. The method for the coordinate expression of two exogeneous coding sequences according to claim 12 wherein the human cell is a retransplantable human cell.

14. The method for the coordinate expression of two exogeneous coding sequences according to claim 13 wherein the retransplantable human cell is an hematopoietic cell.

15. A method for generating a transgenic non-human organism comprising the step of transforming non-human animal cells with an expression construct containing the bidirectional expression cassette according to claim 3.

16. A method for generating a transgenic non-human organism comprising the step of transforming non-human animal cells with the gene transfer expression vector according to claim 7.

* * * * *

UNITED STATES PATENT AND TRADEMARK OFFICE
CERTIFICATE OF CORRECTION

PATENT NO. : 8,501,464 B2  Page 1 of 1
APPLICATION NO. : 10/554181
DATED : August 6, 2013
INVENTOR(S) : Naldini et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 880 days.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(20)
<223> OTHER INFORMATION: LV forward primer

<400> SEQUENCE: 1
```

-continued

| tgaaagcgaa agggaaacca | 20 |

```
<210> SEQ ID NO 2
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(15)
<223> OTHER INFORMATION: LV reverse primer

<400> SEQUENCE: 2
```

| ccgtgcgcgc ttcag | 15 |

```
<210> SEQ ID NO 3
<211> LENGTH: 18
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: (1)..(18)
<223> OTHER INFORMATION:
<220> FEATURE:
<221> NAME/KEY: misc_feature
<222> LOCATION: (1)..(18)
<223> OTHER INFORMATION: LV probe

<400> SEQUENCE: 3
```

| ctctctcgac gcaggact | 18 |

```
<210> SEQ ID NO 4
<211> LENGTH: 9613
<212> TYPE: DNA
<213> ORGANISM: Artificial Sequence
<220> FEATURE:
<223> OTHER INFORMATION: plasmid
<220> FEATURE:
<221> NAME/KEY: misc_feature
<222> LOCATION: (1)..(9613)
<223> OTHER INFORMATION: plasmid containing the lentiviral vector
      construct RRL-MA1-lucif/GFP

<400> SEQUENCE: 4
```

| caggtggcac ttttcgggga aatgtgcgcg gaacccctat ttgtttattt ttctaaatac | 60 |
| attcaaatat gtatccgctc atgagacaat aaccctgata aatgcttcaa taatattgaa | 120 |
| aaaggaagag tatgagtatt caacatttcc gtgtcgccct tattcccttt tttgcggcat | 180 |
| tttgccttcc tgttttttgct cacccagaaa cgctggtgaa agtaaaagat gctgaagatc | 240 |
| agttgggtgc acgagtgggt tacatcgaac tggatctcaa cagcggtaag atccttgaga | 300 |
| gttttcgccc cgaagaacgt tttccaatga tgagcacttt taaagttctg ctatgtggcg | 360 |
| cggtattatc ccgtattgac gccgggcaag agcaactcgg tcgccgcata cactattctc | 420 |
| agaatgactt ggttgagtac tcaccagtca cagaaaagca tcttacggat ggcatgacag | 480 |
| taagagaatt atgcagtgct gccataacca tgagtgataa cactgcggcc aacttacttc | 540 |
| tgacaacgat cggaggaccg aaggagctaa ccgcttttttt gcacaacatg gggatcatg | 600 |
| taactcgcct tgatcgttgg gaaccggagc tgaatgaagc cataccaaac gacgagcgtg | 660 |
| acaccacgat gcctgtagca atggcaacaa cgttgcgcaa actattaact ggcgaactac | 720 |
| ttactctagc ttcccggcaa caattaatag actggatgga gcggataaa gttgcaggac | 780 |
| cacttctgcg ctcggccctt ccggctggct ggtttattgc tgataaatct ggagccggtg | 840 |

```
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt catttttaat ttaaaaggat ctaggtgaag atcctttttg   1080
ataatctcat gaccaaaatc ccttaacgtg agttttcgtt ccactgagcg tcagaccccg   1140
tagaaaagat caaaggatct tcttgagatc ctttttttct gcgcgtaatc tgctgcttgc   1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagctatgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgatt   2160
acgccaagcg cgcaattaac cctcactaaa gggaacaaaa gctggagctg caagcttaat   2220
gtagtcttat gcaatactct tgtagtcttg caacatggta acgatgagtt agcaacatgc   2280
cttacaagga gagaaaaagc accgtgcatg ccgattggtg gaagtaaggt ggtacgatcg   2340
tgccttatta ggaaggcaac agacgggtct gacatggatt ggacgaacca ctgaattgcc   2400
gcattgcaga gatattgtat ttaagtgcct agctcgatac aataaacggg tctctctggt   2460
tagaccagat ctgagcctgg gagctctctg gctaactagg gaacccactg cttaagcctc   2520
aataaagctt gccttgagtg cttcaagtag tgtgtgcccg tctgttgtgt gactctggta   2580
actagagatc cctcagaccc ttttagtcag tgtggaaaat ctctagcagt ggcgcccgaa   2640
cagggacctg aaagcgaaag ggaaaccaga gctctctcga cgcaggactc ggcttgctga   2700
agcgcgcacg gcaagaggcg aggggcggcg actggtgagt acgccaaaaa ttttgactag   2760
cggaggctag aaggagagag atgggtgcga gagcgtcagt attaagcggg ggagaattag   2820
atcgcgatgg gaaaaaattc ggttaaggcc agggggaaag aaaaaatata aattaaaaca   2880
tatagtatgg gcaagcaggg agctagaacg attcgcagtt aatcctggcc tgttagaaac   2940
atcagaaggc tgtagacaaa tactgggaca gctacaacca tcccttcaga caggatcaga   3000
agaacttaga tcattatata atacagtagc aaccctctat tgtgtgcatc aaaggataga   3060
gataaaagac accaaggaag ctttagacaa gatagaggaa gagcaaaaca aaagtaagac   3120
caccgcacag caagcggccg ctgatcttca gacctgagg aggagatatg agggacaatt   3180
ggagaagtga attatataaa tataaagtag taaaaattga accattagga gtagcaccca   3240
```

```
ccaaggcaaa gagaagagtg gtgcagagag aaaaaagagc agtgggaata ggagctttgt    3300
tccttgggtt cttgggagca gcaggaagca ctatgggcgc agcctcaatg acgctgacgg    3360
tacaggccag acaattattg tctggtatag tgcagcagca gaacaatttg ctgagggcta    3420
ttgaggcgca acagcatctg ttgcaactca cagtctgggg catcaagcag ctccaggcaa    3480
gaatcctggc tgtggaaaga tacctaaagg atcaacagct cctggggatt tggggttgct    3540
ctggaaaact catttgcacc actgctgtgc cttggaatgc tagttggagt aataaatctc    3600
tggaacagat ttggaatcac acgacctgga tggagtggga cagagaaatt aacaattaca    3660
caagcttaat acactcctta attgaagaat cgcaaaacca gcaagaaaag aatgaacaag    3720
aattattgga attagataaa tgggcaagtt tgtggaattg gtttaacata acaaattggc    3780
tgtggtatat aaaattattc ataatgatag taggaggctt ggtaggttta agaatagttt    3840
ttgctgtact ttctatagtg aatagagtta ggcaggata ttcaccatta tcgtttcaga    3900
cccacctccc aaccccgagg ggacccgaca ggcccgaagg aatagaagaa gaaggtggag    3960
agagagacag agacagatcc attcgattag tgaacggatc tcgacggtat cggttaactt    4020
ttaaaagaaa aggggggatt ggggggtaca gtgcagggga aagaatagta gacataatag    4080
caacagacat acaaactaaa gaattacaaa acaaattac aaaaattcaa aattttatcg    4140
atcacgagac tagcctcgag agatctgatc ataatcagcc ataccacatt tgtagaggtt    4200
ttacttgctt taaaaaacct cccacacctc cccctgaacc tgaaacataa aatgaatgca    4260
attgttgttg ttaacttgtt tattgcagct tataatggtt acaataagg caatagcatc    4320
acaaatttca caaataaggc attttttca ctgcattcta gttttggttt gtccaaactc    4380
atcaatgtat cttatcatgt ctggatctca aatccctcgg aagctgcgcc tgtcttaggt    4440
tggagtgata cattttatc acttttaccc gtctttggat taggcagtag ctctgacggc    4500
cctcctgtct taggttagtg aaaaatgtca ctctcttacc cgtcattggc tgtccagctt    4560
agctcgcagg ggaggtggtc tggatcctct agaattacac ggcgatcttt ccgcccttct    4620
tggcctttat gaggatctct ctgattttc ttgcgtcgag ttttccggta agacctttcg    4680
gtacttcgtc cacaaacaca actcctccgc gcaactttt cgcggttgtt acttgactgg    4740
ccacgtaatc cacgatctct ttttccgtca tcgtctttcc gtgctccaaa acaacaacgg    4800
cggcgggaag ttcaccggcg tcatcgtcgg gaagacctgc gacacctgcg tcgaagatgt    4860
tggggtgttg gagcaagatg gattccaatt cagcgggagc cacctgatag cctttgtact    4920
taatcagaga cttcaggcgg tcaacgatga agaagtgttc gtcttcgtcc cagtaagcta    4980
tgtctccaga atgtagccat ccatccttgt caatcaaggc gttggtcgct tccggattgt    5040
ttacataacc ggacataatc ataggacctc tcacacacag ttcgcctctt tgattaacgc    5100
ccagcgtttt cccggtatcc agatccacaa ccttcgcttc aaaaaatgga acaactttac    5160
cgaccgcgcc cggtttatca tcccctcgg gtgtaatcag aatagctgat gtagtctcag    5220
tgagcccata tccttgcctg atacctggca gatggaacct cttggcaacc gcttccccga    5280
cttccttaga gaggggagcg ccaccagaag caatttcgtg taaattagat aaatcgtatt    5340
tgtcaatcag agtgcttttg gcgaagaagg agaatagggt tggcaccagc agcgcacttt    5400
gaatcttgta atcctgaagg ctcctcagaa acagctcttc ttcaaatcta tacattaaga    5460
cgactcgaaa tccacatatc aaatatccga gtgtagtaaa cattccaaaa ccgtgatgga    5520
atggaacaac acttaaaatc gcagtatccg gaatgatttg attgccaaaa ataggatctc    5580
tggcatgcga gaatctcacg caggcagttc tatgaggcag agcgacacct ttaggcagac    5640
```

```
cagtagatcc agaggagttc atgatcagtg caattgtctt gtcccwtatcg aaggactctg   5700
gcacaaaatc gtattcatta aaaccgggag gtagatgaga tgtgacgaac gtgtacatcg   5760
actgaaatcc ctggtaatcc gttttagaat ccatgataat aatttttttgg atgattggga  5820
gcttttttttg cacgttcaaa atttttttgca accccttttt ggaaacgaac accacggtag  5880
gctgcgaaat gcccatactg ttgagcaatt cacgttcatt ataaatgtcg ttcgcgggcg   5940
caactgcaac tccgataaat aacgcgccca acaccggcat aaagaattga agagagtttt   6000
cactgcatac gacgattctg tgatttgtat tcagcccata tcgtttcata gcttctgcca   6060
accgaacgga catttcgaag tactcagcgt aagtgatgtc cacctcgata tgtgcatctg   6120
taaaagcaat tgttccagga accagggcgt atctcttcat agccttatgc agttgctctc   6180
cagcggttcc atcttccagc ggatagaatg gcgccgggcc tttctttatg ttttttggcgt   6240
cttccatggt gaattccgcg gaggctggat cggtcccggt gtcttctatg gaggtcaaaa   6300
cagcgtggat ggcgtctcca ggcgatctga cggttcacta aacgagctct gcttatatag   6360
gcctcccacc gtacacgcct accctcgaga agcttgatat cgaattccca cggggttggg   6420
gttgcgcctt ttcaaggca gccctgggtt tgcgcaggga cgcggctgct ctgggcgtgg    6480
ttccgggaaa cgcagcggcg ccgaccctgg gtctcgcaca ttcttcacgt ccgttcgcag    6540
cgtcacccgg atcttcgccg ctacccttgt gggcccccccg cgacgcttc ctgctccgcc    6600
cctaagtcgg gaaggttcct tgcggttcgc ggcgtgccgg acgtgacaaa cggaagccgc    6660
acgtctcact agtaccctcg cagacggaca gcgccaggga gcaatggcag cgcgccgacc    6720
gcgatgggct gtggccaata gcggctgctc agcggggcgc gccgagagca gcggccggga    6780
aggggcggtg cgggaggcgg ggtgtggggc ggtagtgtgg gccctgttcc tgcccgcgcg    6840
gtgttccgca ttctgcaagc ctccggagcg cacgtcggca gtcggctccc tcgttgaccg    6900
aatcaccgac ctctctcccc aggggggatcc accggtcgcc accatggtga gcaagggcga    6960
ggagctgttc accggggtgg tgcccatcct ggtcgagctg gacggcgacg taaacggcca    7020
caagttcagc gtgtccggcg agggcgaggg cgatgccacc tacggcaagc tgaccctgaa    7080
gttcatctgc accaccggca agctgcccgt gccctggccc accctcgtga ccaccctgac    7140
ctacggcgtg cagtgcttca gccgctaccc cgaccacatg aagcagcacg acttcttcaa    7200
gtccgccatg cccgaaggct acgtccagga gcgcaccatc ttcttcaagg acgacggcaa    7260
ctacaagacc cgcgccgagg tgaagttcga gggcgacacc ctggtgaacc gcatcgagct    7320
gaagggcatc gacttcaagg aggacggcaa catcctgggg cacaagctgg agtacaacta    7380
caacagccac aacgtctata tcatggccga caagcagaag aacggcatca aggtgaactt    7440
caagatccgc cacaacatcg aggacggcag cgtgcagctc gccgaccact accagcagaa    7500
cacccccatc ggcgacggcc ccgtgctgct gcccgacaac cactacctga gcacccagtc    7560
cgccctgagc aaagacccca acgagaagcg cgatcacatg gtcctgctgg agttcgtgac    7620
cgccgccggg atcactctcg gcatggacga gctgtacaag taaagcggcc gcgtcgacaa    7680
tcaacctctg gattacaaaa tttgtgaaag attgactggt attcttaact atgttgctcc    7740
ttttacgcta tgtggatacg ctgctttaat gcctttgtat catgctattg cttcccgtat    7800
ggctttcatt ttctcctcct tgtataaatc ctggttgctg tctctttatg aggagttgtg    7860
gcccgttgtc aggcaacgtg gcgtggtgtg cactgtgttt gctgacgcaa cccccactgg    7920
ttggggcatt gccaccacct gtcagctcct ttccgggact ttcgctttcc cctcccctat    7980
tgccacggcg gaactcatcg ccgcctgcct tgcccgctgc tggacagggg ctcggctgtt    8040
```

```
gggcactgac aattccgtgg tgttgtcggg gaagctgacg tcctttccat ggctgctcgc      8100
ctgtgttgcc acctggattc tgcgcgggac gtccttctgc tacgtccctt cggccctcaa      8160
tccagcggac cttccttccc gcggcctgct gccggctctg cggcctcttc cgcgtcttcg      8220
ccttcgccct cagacgagtc ggatctccct ttgggccgcc tccccgcctg gaattcgagc      8280
tcggtacctt taagaccaat gacttacaag gcagctgtag atcttagcca cttttttaaaa     8340 gaaaaggggg gactggaagg gctaattcac tcccaacgaa gacaagatct gcttttttgct     8400 tgtactgggt ctctctggtt agaccagatc tgagcctggg agctctctgg ctaactaggg      8460
aacccactgc ttaagcctca ataaagcttg ccttgagtgc ttcaagtagt gtgtgcccgt      8520
ctgttgtgtg actctggtaa ctagagatcc ctcagaccct tttagtcagt gtggaaaatc      8580
tctagcagta gtagttcatg tcatcttatt attcagtatt tataacttgc aaagaaatga      8640
atatcagaga gtgagaggaa cttgtttatt gcagcttata atggttacaa ataaagcaat      8700
agcatcacaa atttcacaaa taaagcattt ttttcactgc attctagttg tggtttgtcc      8760
aaactcatca atgtatctta tcatgtctgg ctctagctat cccgccccta actccgccca      8820
gttccgccca ttctccgccc catggctgac taattttttt tatttatgca gaggccgagg      8880
ccgcctcggc ctctgagcta ttccagaagt agtgaggagg cttttttgga ggcctaggct      8940
tttgcgtcga cgtacccca attcgcccta tagtgagtcg tattacgcgc gctcactggc       9000
cgtcgtttta caacgtcgtg actgggaaaa ccctggcgtt acccaactta atcgccttgc      9060
agcacatccc cctttcgcca gctggcgtaa tagcgaagag gcccgcaccg atcgcccttc      9120
ccaacagttg cgcagcctga atggcgaatg gcgcgacgcg cctgtagcg gcgcattaag       9180 cgcggcgggt gtggtggtta cgcgcagcgt gaccgctaca cttgccagcg ccctagcgcc      9240
cgctcctttc gctttcttcc cttcctttct cgccacgttc gccggctttc cccgtcaagc      9300
tctaaatcgg gggctccctt tagggttccg atttagtgct ttacggcacc tcgaccccaa      9360
aaaacttgat tagggtgatg gttcacgtag tgggccatcg ccctgataga cggttttttcg     9420 ccctttgacg ttggagtcca cgttctttaa tagtggactc ttgttccaaa ctggaacaac      9480
actcaaccct atctcggtct attcttttga tttataaggg attttgccga tttcggccta      9540
ttggttaaaa aatgagctga tttaacaaaa atttaacgcg aattttaaca aaatattaac      9600
gtttacaatt tcc                                                         9613

<210> SEQ ID NO 5
<211> LENGTH: 9380
<212> TYPE: DNA
<213> ORGANISM: Artificial Sequence
<220> FEATURE:
<223> OTHER INFORMATION: plasmid
<220> FEATURE:
<221> NAME/KEY: misc_feature
<222> LOCATION: (1)..(9380)
<223> OTHER INFORMATION:
<220> FEATURE:
<221> NAME/KEY: misc_feature
<222> LOCATION: (1)..(9380)
<223> OTHER INFORMATION: plasmid containing the lentiviral vector
      construct CCL-MA1-GFP/de ltaLNGFR

<400> SEQUENCE: 5
caggtggcac ttttcgggga aatgtgcgcg gaacccctat ttgtttattt ttctaaatac        60
attcaaatat gtatccgctc atgagacaat aaccctgata aatgcttcaa taatattgaa       120
aaaggaagag tatgagtatt caacatttcc gtgtcgccct tattcccttt tttgcggcat       180
```

```
tttgccttcc tgttttttgct cacccagaaa cgctggtgaa agtaaaagat gctgaagatc    240
agttgggtgc acgagtgggt tacatcgaac tggatctcaa cagcggtaag atccttgaga    300
gttttcgccc cgaagaacgt tttccaatga tgagcacttt taaagttctg ctatgtggcg    360
cggtattatc ccgtattgac gccgggcaag agcaactcgg tcgccgcata cactattctc    420
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgcttttttt gcacaacatg ggggatcatg    600
taactcgcct tgatcgttgg gaaccggagc tgaatgaagc cataccaaac gacgagcgtg    660
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac    1020
tttagattga tttaaaactt cattttttaat ttaaaaggat ctaggtgaag atcctttttg    1080
ataatctcat gaccaaaatc ccttaacgtg agttttcgtt ccactgagcg tcagaccccg    1140
tagaaaagat caaaggatct tcttgagatc ctttttttct gcgcgtaatc tgctgcttgc    1200
aaacaaaaaa accaccgcta ccagcggtgg tttgtttgcc ggatcaagag ctaccaactc    1260
tttttccgaa ggtaactggc ttcagcagag cgcagatacc aaatactgtc cttctagtgt    1320
agccgtagtt aggccaccac ttcaagaact ctgtagcacc gcctacatac ctcgctctgc    1380
taatcctgtt accagtggct gctgccagtg gcgataagtc gtgtcttacc gggttggact    1440
caagacgata gttaccggat aaggcgcagc ggtcgggctg aacggggggt tcgtgcacac    1500
agcccagctt ggagcgaacg acctacaccg aactgagata cctacagcgt gagctatgag    1560
aaagcgccac gcttcccgaa gggagaaagg cggacaggta tccggtaagc ggcagggtcg    1620
gaacaggaga gcgcacgagg gagcttccag ggggaaacgc ctggtatctt tatagtcctg    1680
tcgggtttcg ccacctctga cttgagcgtc gatttttgtg atgctcgtca gggggggcgga    1740 gcctatggaa aaacgccagc aacgcggcct ttttacggtt cctggccttt tgctggcctt    1800
ttgctcacat gttctttcct gcgttatccc ctgattctgt ggataaccgt attaccgcct    1860
ttgagtgagc tgataccgct cgccgcagcc gaacgaccga gcgcagcgag tcagtgagcg    1920
aggaagcgga agagcgccca atacgcaaac cgcctctccc cgcgcgttgg ccgattcatt    1980
aatgcagctg gcacgacagg tttcccgact ggaaagcggg cagtgagcgc aacgcaatta    2040
atgtgagtta gctcactcat taggcacccc aggctttaca ctttatgctt ccggctcgta    2100
tgttgtgtgg aattgtgagc ggataacaat ttcacacagg aaacagctat gaccatgatt    2160
acgccaagcg cgcaattaac cctcactaaa gggaacaaaa gctggagctg caagcttggc    2220
cattgcatac gttgtatcca tatcataata tgtacattta tattggctca tgtccaacat    2280
taccgccatg ttgacattga ttattgacta gttattaata gtaatcaatt acgggtcat    2340 tagttcatag cccatatatg gagttccgcg ttacataact tacggtaaat ggcccgcctg    2400
gctgaccgcc caacgacccc cgcccattga cgtcaataat gacgtatgtt cccatagtaa    2460
cgccaatagg gactttccat tgacgtcaat gggtggagta tttacggtaa actgcccact    2520
tggcagtaca tcaagtgtat catatgccaa gtacgccccc tattgacgtc aatgacggta    2580
```

```
aatggcccgc ctggcattat gcccagtaca tgaccttatg ggactttcct acttggcagt    2640
acatctacgt attagtcatc gctattacca tggtgatgcg gttttggcag tacatcaatg    2700
ggcgtggata gcggtttgac tcacggggat ttccaagtct ccaccccatt gacgtcaatg    2760
ggagtttgtt ttggcaccaa atcaacggg actttccaaa atgtcgtaac aactccgccc    2820
cattgacgca aatgggcggt aggcgtgtac ggtgggaggt ctatataagc agagctcgtt    2880
tagtgaaccg gggtctctct ggttagacca gatctgagcc tgggagctct ctggctaact    2940
agggaaccca ctgcttaagc ctcaataaag cttgccttga gtgcttcaag tagtgtgtgc    3000
ccgtctgttg tgtgactctg gtaactagag atccctcaga cccttttagt cagtgtggaa    3060
aatctctagc agtggcgccc gaacagggac ctgaaagcga agggaaaacc agagctctct    3120
cgacgcagga ctcggcttgc tgaagcgcgc acggcaagag gcgaggggcg gcgactggtg    3180
agtacgccaa aaattttgac tagcggaggc tagaaggaga gagatgggtg cgagagcgtc    3240
agtattaagc gggggagaat tagatcgcga tgggaaaaaa ttcggttaag gccaggggga    3300
aagaaaaaat ataaattaaa acatatagta tgggcaagca gggagctaga acgattcgca    3360
gttaatcctg gcctgttaga acatcagaa ggctgtagac aaatactggg acagctacaa    3420
ccatcccttc agacaggatc agaagaactt agatcattat ataatacagt agcaaccctc    3480
tattgtgtgc atcaaaggat agagataaaa gacaccaagg aagctttaga caagatagag    3540
gaagagcaaa acaaaagtaa gaccaccgca cagcaagcgg ccgctgatct tcagacctgg    3600
aggaggagat atgagggaca attggagaag tgaattatat aaatataaag tagtaaaaat    3660
tgaaccatta ggagtagcac ccaccaaggc aaagagaaga gtggtgcaga gagaaaaaag    3720
agcagtggga ataggagctt tgttccttgg gttcttggga gcagcaggaa gcactatggg    3780
cgcagcctca atgacgctga cggtacaggc cagacaatta ttgtctggta tagtgcagca    3840
gcagaacaat ttgctgaggg ctattgaggc gcaacagcat ctgttgcaac tcacagtctg    3900
gggcatcaag cagctccagg caagaatcct ggctgtggaa agatacctaa aggatcaaca    3960
gctcctgggg atttggggtt gctctggaaa actcatttgc accactgctg tgccttggaa    4020
tgctagttgg agtaataaat ctctggaaca gattggaatc acacgacctg gatggagtgg    4080
gacagagaaa ttaacaatta cacaagctta atacactcct taattgaaga atcgcaaaac    4140
cagcaagaaa agaatgaaca agaattattg gaattagata atgggcaag tttgtggaat    4200 tggtttaaca taacaaattg gctgtggtat ataaaattat tcataatgat agtaggaggc    4260
ttggtaggtt taagaatagt ttttgctgta ctttctatag tgaatagagt taggcaggga    4320
tattcaccat tatcgtttca gacccacctc ccaaccccga ggggacccga caggcccgaa    4380
ggaatagaag aagaaggtgg agagagagac agagacagat ccattcgatt agtgaacgga    4440
tctcgacggt atcggttaac ttttaaaaga aaggggggga ttgggggta cagtgcaggg    4500 gaaagaatag tagacataat agcaacagac atacaaacta agaattaca aaaacaaatt    4560 acaaaaattc aaaattttat cgatcacgag actagcctcg agagatctga tcataatcag    4620
ccataccaca tttgtagagg ttttacttgc tttaaaaaac ctcccacacc tccccctgaa    4680
cctgaaacat aaaatgaatg caattgttgt tgttaacttg tttattgcag cttataatgg    4740
ttacaaataa ggcaatagca tcacaaattt cacaaataag gcattttttt cactgcattc    4800
tagttttggt ttgtccaaac tcatcaatgt atcttatcat gtctggatct caaatccctc    4860
ggaagctgcg cctgtcttag gttggagtga tacatttta tcactttac ccgtctttgg    4920 attaggcagt agctctgacg gccctcctgt cttaggttag tgaaaaatgt cactctctta    4980
```

```
cccgtcattg gctgtccagc ttagctcgca ggggaggtgg tctggatccg agctcgaatt    5040
ggccgcttta cttgtacagc tcgtccatgc cgagagtgat cccggcggcg gtcacgaact    5100
ccagcaggac catgtgatcg cgcttctcgt tggggtcttt gctcagggcg gactgggtgc    5160
tcaggtagtg gttgtcgggc agcagcacgg ggccgtcgcc gatggggtg ttctgctggt     5220 agtggtcggc gagctgcacg ctgccgtcct cgatgttgtg gcggatcttg aagttcacct    5280
tgatgccgtt cttctgcttg tcggccatga tatagacgtt gtggctgttg tagttgtact    5340
ccagcttgtg ccccaggatg ttgccgtcct ccttgaagtc gatgcccttc agctcgatgc    5400
ggttcaccag ggtgtcgccc tcgaacttca cctcggcgcg gtcttgtag ttgccgtcgt     5460 ccttgaagaa gatggtgcgc tcctggacgt agccttcggg catggcggac ttgaagaagt    5520
cgtgctgctt catgtggtcg gggtagcggc tgaagcactg cacgccgtag gtcagggtgg    5580
tcacgagggt gggccagggc acgggcagct tgccggtggt gcagatgaac ttcagggtca    5640
gcttgccgta ggtggcatcg ccctcgccct cgccggacac gctgaacttg tggccgttta    5700
cgtcgccgtc cagctcgacc aggatgggca ccaccccggt gaacagctcc tcgcccttgc    5760
tcaccatggt gaattccgcg gaggctggat cggtcccggt gtcttctatg gaggtcaaaa    5820
cagcgtggat ggcgtctcca ggcgatctga cggttcacta aacgagctct gcttatatag    5880
gcctcccacc gtacacgcct accctcgaga agcttgatat cgaattccca cggggttggg    5940
gttgcgcctt ttccaaggca gccctgggtt tgcgcaggga cgcggctgct ctgggcgtgg    6000
ttccgggaaa cgcagcggcg ccgacccctgg gtctcgcaca ttcttcacgt ccgttcgcag    6060
cgtcacccgg atcttcgccg ctacccttgt gggccccccg gcgacgcttc ctgctccgcc    6120
cctaagtcgg gaaggttcct tgcggttcgc ggcgtgccgg acgtgacaaa cggaagccgc    6180
acgtctcact agtaccctcg cagacggaca gcgcaggga gcaatggcag cgcgccgacc      6240
gcgatgggct gtggccaata gcggctgctc agcggggcgc gccgagagca gcggccggga    6300
aggggcggtg cggaggcgg ggtgtgggc ggtagtgtgg gccctgttcc tgcccgcgcg        6360
gtgttccgca ttctgcaagc ctccggagcg cacgtcggca gtcggctccc tcgttgaccg    6420
aatcaccgac ctctctcccc agggggatcc cccgggctgc aggaattcgg gccgcggcca    6480
gctccggcgg gcagggggg cgctggagcg cagcgcagcg cagccccatc agtccgcaaa      6540
gcggaccgag ctgaaagtcg agcgctgccg cgggaggcgg gcgatggggg caggtgccac    6600
cggccgcgcc atggacgggc gcgcctgct gctgttgctg cttctggggg tgtcccttgg      6660
aggtgccaag gaggcatgcc ccacaggcct gtacacacac agcggtgagt gctgcaaagc    6720
ctgcaacctg ggcgagggtg tggcccagcc ttgtggagcc aaccagaccg tgtgtgagcc    6780
ctgcctggac agcgtgacgt tctccgacgt ggtgagcgcg accgagccgt gcaagccgtg    6840
caccgagtgc gtggggctcc agagcatgtc ggcgccgtgc gtggaggccg acgacgccgt    6900
gtgccgctgc gcctacggct actaccagga tgagacgact gggcgctgcg aggcgtgccg    6960
cgtgtgcgag gcgggctcgg gcctcgtgtt ctcctgccag gacaagcaga acaccgtgtg    7020
cgaggagtgc cccgacggca cgtattccga cgaggccaac cacgtggacc cgtgcctgcc    7080
ctgcaccgtg tgcgaggaca ccgagcgcca gctccgcgag tgcacacgct gggccgacgc    7140
cgagtgcgag gagatccctg ccgttggat tacacggtcc acacccccag agggctcgga    7200
cagcacagcc cccagcaccc aggagcctga ggcacctcca gaacaagacc tcatagccag    7260
cacggtggca ggtgtggtga ccacagtgat gggcagctcc cagcccgtgg tgacccgagg    7320
caccaccgac aacctcatcc ctgtctattg ctccatcctg gctgctgtgg ttgtgggcct    7380
```

```
tgtggcctac atagccttca agaggtggaa caggggggatc ctctagagtc gagtctagag    7440
tcgacaatca acctctggat tacaaaattt gtgaaagatt gactggtatt cttaactatg    7500
ttgctccttt tacgctatgt ggatacgctg ctttaatgcc tttgtatcat gctattgctt    7560
cccgtatggc tttcattttc tcctccttgt ataaatcctg gttgctgtct ctttatgagg    7620
agttgtggcc cgttgtcagg caacgtggcg tggtgtgcac tgtgtttgct gacgcaaccc    7680
ccactggttg gggcattgcc accacctgtc agctcctttc cgggactttc gctttccccc    7740
tccctattgc cacggcggaa ctcatcgccg cctgccttgc ccgctgctgg acaggggctc    7800
ggctgttggg cactgacaat ccgtggtgt gtcggggaa gctgacgtcc tttccatggc    7860
tgctcgcctg tgttgccacc tggattctgc gcgggacgtc cttctgctac gtcccttcgg    7920
ccctcaatcc agcggacctt ccttcccgcg gcctgctgcc ggctctgcgg cctcttccgc    7980
gtcttcgcct tcgccctcag acgagtcgga tctcccttgg ggccgcctcc ccgcctggaa    8040
ttcgagctcg gtacctttaa gaccaatgac ttacaaggca gctgtagatc ttagccactt    8100
tttaaaagaa agggggggac tggaagggct aattcactcc caacgaagac aagatctgct    8160
ttttgcttgt actgggtctc tctggttaga ccagatctga gcctgggagc tctctggcta    8220
actagggaac ccactgctta agcctcaata agcttgcct tgagtgcttc aagtagtgtg    8280
tgcccgtctg ttgtgtgact ctggtaacta gagatccctc agaccctttt agtcagtgtg    8340
gaaaatctct agcagtagta gttcatgtca tcttattatt cagtatttat aacttgcaaa    8400
gaaatgaata tcagagagtg agaggaactt gtttattgca gcttataatg gttacaaata    8460
aagcaatagc atcacaaatt tcacaaataa agcatttttt tcactgcatt ctagttgtgg    8520
tttgtccaaa ctcatcaatg tatcttatca tgtctggctc tagctatccc gcccctaact    8580
ccgcccagtt ccgcccattc tccgccccat ggctgactaa ttttttttat ttatgcagag    8640
gccgaggccg cctcggcctc tgagctattc cagaagtagt gaggaggctt ttttggaggc    8700
ctaggctttt gcgtcgagac gtacccaatt cgccctatag tgagtcgtat tacgcgcgct    8760
cactggccgt cgttttacaa cgtcgtgact gggaaaaccc tggcgttacc caacttaatc    8820
gccttgcagc acatccccct ttcgccagct ggcgtaatag cgaagaggcc cgcaccgatc    8880
gcccttccca acagttgcgc agcctgaatg gcgaatggcg cgacgcgccc tgtagcggcg    8940
cattaagcgc ggcgggtgtg gtggttacgc gcagcgtgac cgctacactt gccagcgccc    9000
tagcgcccgc tcctttcgct ttcttccctt cctttctcgc cacgttcgcc ggctttcccc    9060
gtcaagctct aaatcggggg ctccctttag ggttccgatt tagtgcttta cggcacctcg    9120
accccaaaaa acttgattag ggtgatggtt cacgtagtgg gccatcgccc tgatagacgg    9180
tttttcgccc tttgacgttg gagtccacgt tctttaatag tggactcttg ttccaaactg    9240
gaacaacact caaccctatc tcggtctatt cttttgattt ataagggatt ttgccgattt    9300
cggcctattg gttaaaaaat gagctgattt aacaaaaatt taacgcgaat tttaacaaaa    9360
tattaacgtt tacaatttcc                                                 9380
```

<210> SEQ ID NO 6  
<211> LENGTH: 9718  
<212> TYPE: DNA  
<213> ORGANISM: Artificial Sequence  
<220> FEATURE:  
<223> OTHER INFORMATION: plasmid  
<220> FEATURE:  
<221> NAME/KEY: misc_feature  
<222> LOCATION: (1)..(9718)  
<223> OTHER INFORMATION:  
<220> FEATURE:

<221> NAME/KEY: misc_feature
<222> LOCATION: (1)..(9718)
<223> OTHER INFORMATION: plasmid containing the lentiviral vector
      construct RRL-MA2-lucif/GFP

<400> SEQUENCE: 6

```
caggtggcac ttttcgggga aatgtgcgcg gaacccctat tgtttatttt ttctaaatac    60
attcaaatat gtatccgctc atgagacaat aaccctgata aatgcttcaa taatattgaa   120
aaaggaagag tatgagtatt caacatttcc gtgtcgccct tattccctttt tttgcggcat  180 tttgccttcc tgtttttgct cacccagaaa cgctggtgaa agtaaaagat gctgaagatc   240
agttgggtgc acgagtgggt tacatcgaac tggatctcaa cagcggtaag atccttgaga   300
gttttcgccc cgaagaacgt tttccaatga tgagcacttt taaagttctg ctatgtggcg   360
cggtattatc ccgtattgac gccgggcaag agcaactcgg tcgccgcata cactattctc   420
agaatgactt ggttgagtac tcaccagtca cagaaaagca tcttacggat ggcatgacag   480
taagagaatt atgcagtgct gccataacca tgagtgataa cactgcggcc aacttacttc   540
tgacaacgat cggaggaccg aaggagctaa ccgcttttttt gcacaacatg ggggatcatg   600
taactcgcct tgatcgttgg gaaccggagc tgaatgaagc cataccaaac gacgagcgtg   660
acaccacgat gcctgtagca atggcaacaa cgttgcgcaa actattaact ggcgaactac   720
ttactctagc ttcccggcaa caattaatag actggatgga ggcggataaa gttgcaggac   780
cacttctgcg ctcggccctt ccggctggct ggtttattgc tgataaatct ggagccggtg   840
agcgtgggtc tcgcggtatc attgcagcac tggggccaga tggtaagccc tcccgtatcg   900
tagttatcta cacgacgggg agtcaggcaa ctatggatga acgaaataga cagatcgctg   960
agataggtgc ctcactgatt aagcattggt aactgtcaga ccaagtttac tcatatatac  1020
tttagattga tttaaaactt catttttaat ttaaaaggat ctaggtgaag atccttttg   1080 ataatctcat gaccaaaatc ccttaacgtg agttttcgtt ccactgagcg tcagaccccg  1140
tagaaaagat caaaggatct cttgagatcc ttttttttct gcgcgtaatc tgctgcttgc  1200
aaacaaaaaa accaccgcta ccagcggtgg tttgtttgcc ggatcaagag ctaccaactc  1260
tttttccgaa ggtaactggc ttcagcagag cgcagatacc aaatactgtc cttctagtgt  1320
agccgtagtt aggccaccac ttcaagaact ctgtagcacc gcctacatac ctcgctctgc  1380
taatcctgtt accagtggct gctgccagtg gcgataagtc gtgtcttacc gggttggact  1440
caagacgata gttaccggat aaggcgcagc ggtcgggctg aacggggggt tcgtgcacac  1500
agcccagctt ggagcgaacg acctacaccg aactgagata cctacagcgt gagctatgag  1560
aaagcgccac gcttcccgaa gggagaaagg cggacaggta tccggtaagc ggcagggtcg  1620
gaacaggaga gcgcacgagg gagcttccag ggggaaacgc ctggtatctt tatagtcctg  1680
tcgggtttcg ccacctctga cttgagcgtc gatttttgtg atgctcgtca ggggggcgga  1740
gcctatggaa aaacgccagc aacgcggcct ttttacggtt cctggccttt tgctggcctt  1800
ttgctcacat gttctttcct gcgttatccc ctgattctgt ggataaccgt attaccgcct  1860
ttgagtgagc tgataccgct cgccgcagcc gaacgaccga gcgcagcgag tcagtgagcg  1920
aggaagcgga agagcgccca atacgcaaac cgcctctccc cgcgcgttgg ccgattcatt  1980
aatgcagctg gcacgacagg tttcccgact ggaaagcggg cagtgagcgc aacgcaatta  2040
atgtgagtta gctcactcat taggcacccc aggctttaca ctttatgctt ccggctcgta  2100
tgttgtgtgg aattgtgagc ggataacaat ttcacacagg aaacagctat gaccatgatt  2160
acgccaagcg cgcaattaac cctcactaaa gggaacaaaa gctggagctg caagcttaat  2220
```

```
gtagtcttat gcaatactct tgtagtcttg caacatggta acgatgagtt agcaacatgc    2280
cttacaagga gagaaaaagc accgtgcatg ccgattggtg gaagtaaggt ggtacgatcg    2340
tgccttatta ggaaggcaac agacgggtct gacatggatt ggacgaacca ctgaattgcc    2400
gcattgcaga gatattgtat ttaagtgcct agctcgatac aataaacggg tctctctggt    2460
tagaccagat ctgagcctgg gagctctctg gctaactagg gaacccactg cttaagcctc    2520
aataaagctt gccttgagtg cttcaagtag tgtgtgcccg tctgttgtgt gactctggta    2580
actagagatc cctcagaccc ttttagtcag tgtggaaaat ctctagcagt ggcgcccgaa    2640
cagggacctg aaagcgaaag ggaaaccaga gctctctcga cgcaggactc ggcttgctga    2700
agcgcgcacg gcaagaggcg aggggcggcg actggtgagt acgccaaaaa ttttgactag    2760
cggaggctag aaggagagag atgggtgcga gagcgtcagt attaagcggg ggagaattag    2820
atcgcgatgg gaaaaaattc ggttaaggcc agggggaaag aaaaaatata aattaaaaca    2880
tatagtatgg gcaagcaggg agctagaacg attcgcagtt aatcctggcc tgttagaaac    2940
atcagaaggc tgtagacaaa tactgggaca gctacaacca tcccttcaga caggatcaga    3000
agaacttaga tcattatata atacagtagc aaccctctat tgtgtgcatc aaaggataga    3060
gataaaagac accaaggaag ctttagacaa gatagaggaa gagcaaaaca aaagtaagac    3120
caccgcacag caagcggccg ctgatcttca gacctggagg aggagatatg agggacaatt    3180
ggagaagtga attatataaa tataaagtag taaaaattga accattagga gtagcaccca    3240
ccaaggcaaa gagaagagtg gtgcagagag aaaaaagagc agtgggaata ggagctttgt    3300
tccttgggtt cttgggagca gcaggaagca ctatgggcgc agcctcaatg acgctgacgg    3360
tacaggccag acaattattg tctggtatag tgcagcagca gaacaatttg ctgagggcta    3420
ttgaggcgca acagcatctg ttgcaactca cagtctgggg catcaagcag ctccaggcaa    3480
gaatcctggc tgtggaaaga tacctaaagg atcaacagct cctggggatt tggggttgct    3540
ctggaaaact catttgcacc actgctgtgc cttggaatgc tagttggagt aataaatctc    3600
tggaacagat tggaatcaca cgacctggat ggagtgggac agagaaatta acaattacac    3660
aagcttaata cactccttaa ttgaagaatc gcaaaaccag caagaaaaga atgaacaaga    3720
attattggaa ttagataaat gggcaagttt gtggaattgg tttaacataa caaattggct    3780
gtggtatata aaattattca taatgatagt aggaggcttg gtaggtttaa gaatagtttt    3840
tgctgtactt tctatagtga atagagttag gcagggatat tcaccattat cgtttcagac    3900
ccacctccca accccgaggg gacccgacag gcccgaagga atagaagaag aaggtggaga    3960
gagagacaga gacagatcca ttcgattagt gaacggatct cgacggtatc ggttaacttt    4020
taaaagaaaa ggggggattg ggggtacag tgcagggaa agaatagtag acataatagc    4080
aacagacata caaactaaag aattacaaaa acaaattaca aaattcaaa attttatcga    4140 tcacgagact agcctcgaga gatctgatca taatcagcca taccacattt gtagaggttt    4200
tacttgcttt aaaaaacctc ccacacctcc cctgaacct gaaacataaa atgaatgcaa    4260
ttgttgttgt taacttgttt attgcagctt ataatggtta caaataaggc aatagcatca    4320
caaatttcac aaataaggca tttttttcac tgcattctag ttttggtttg tccaaactca    4380
tcaatgtatc ttatcatgtc tggatctcaa atccctcgga agctgcgcct gtcttaggtt    4440
ggagtgatac atttttatca cttttacccg tctttggatt aggcagtagc tctgacggcc    4500
ctcctgtctt aggttagtga aaaatgtcac tctcttaccc gtcattggct gtccagctta    4560
gctcgcaggg gaggtggtct ggatccctgg atatcaagaa ttcgtcctcg agctcagatc    4620
```

```
ctctagaatt acacggcgat ctttccgccc ttcttggcct ttatgaggat ctctctgatt    4680
tttcttgcgt cgagttttcc ggtaagacct ttcggtactt cgtccacaaa cacaactcct    4740
ccgcgcaact ttttcgcggt tgttacttga ctggccacgt aatccacgat ctcttttttcc   4800
gtcatcgtct ttccgtgctc caaaacaaca acggcggcgg gaagttcacc ggcgtcatcg    4860
tcgggaagac ctgcgacacc tgcgtcgaag atgttgggt gttggagcaa gatggattcc     4920
aattcagcgg gagccacctg atagcctttg tacttaatca gagacttcag gcggtcaacg    4980
atgaagaagt gttcgtcttc gtcccagtaa gctatgtctc cagaatgtag ccatccatcc    5040
ttgtcaatca aggcgttggt cgcttccgga ttgtttacat aaccggacat aatcatagga    5100
cctctcacac acagttcgcc tctttgatta cgcccagcg ttttcccggt atccagatcc     5160
acaaccttcg cttcaaaaaa tggaacaact ttaccgaccg cgcccggttt atcatccccc    5220
tcgggtgtaa tcagaatagc tgatgtagtc tcagtgagcc catatccttg cctgatacct    5280
ggcagatgga acctcttggc aaccgcttcc ccgacttcct tagagagggg agcgccacca    5340
gaagcaattt cgtgtaaatt agataaatcg tatttgtcaa tcagagtgct tttggcgaag    5400
aaggagaata gggttggcac cagcagcgca ctttgaatct tgtaatcctg aaggctcctc    5460
agaaacagct cttcttcaaa tctatacatt aagacgactc gaaatccaca tatcaaatat    5520
ccgagtgtag taaacattcc aaaaccgtga tggaatggaa caacacttaa aatcgcagta    5580
tccggaatga tttgattgcc aaaaatagga tctctggcat gcgagaatct cacgcaggca    5640
gttctatgag gcagagcgac acctttaggc agaccagtag atccagagga gttcatgatc    5700
agtgcaattg tcttgtccct atcgaaggac tctggcacaa aatcgtattc attaaaaccg    5760
ggaggtagat gagatgtgac gaacgtgtac atcgactgaa atccctggta atccgtttta    5820
gaatccatga taataatttt ttggatgatt gggagctttt tttgcacgtt caaaattttt    5880
tgcaacccct ttttggaaac gaacaccacg gtaggctgcg aaatgcccat actgttgagc    5940
aattcacgtt cattataaat gtcgttcgcg ggcgcaactg caactccgat aaataacgcg    6000
cccaacaccg gcataaagaa ttgaagagag ttttcactgc atacgacgat tctgtgattt    6060
gtattcagcc catatcgttt catagcttct gccaaccgaa cggacatttc gaagtactca    6120
gcgtaagtga tgtccacctc gatatgtgca tctgtaaaag caattgttcc aggaaccagg    6180
gcgtatctct tcatagcctt atgcagttgc tctccagcgg ttccatcttc cagcggatag    6240
aatggcgccg ggccttttctt tatgtttttg gcgtcttcca tggtgaattc cgatcccccct   6300
ggggagagag gtcggtgatt cggtcaacga gggagccgac tgccgacgtg cgctccggag    6360
gcttgcagaa tgcggaacac cgcgcgggca ggaacagggc ccacactacc gccccacacc    6420
ccgcctcccg caccgcccct tcccggccgc tgctctcggc gcgcccgct gagcagccgc     6480
tattggccac agcccatcgc ggtcggcgcg ctgccattgc tccctggcgc tgtccgtctg    6540
cgagggtact agtgagacgt gcggcttccg tttgtcacgt ccggcacgcc gcgaaccgca    6600
aggaaccttc ccgacttagg ggcggagcag gaagcgtcgc cggggggccc acaagggtag    6660
cggcgaagat ccgggtgacg ctgcgaacgg acgtgaagaa tgtgcgagac ccagggtcgg    6720
cgccgctgcg tttcccggaa ccacgcccag agcagccgcg tccctgcgca aacccagggc    6780
tgccttggaa aaggcgcaac cccaacccg tgggaattcg atatcaagct tgcctatgtt     6840
cttttggaat ctatccaagt cttatgtaaa tgcttatgta aaccataata taaaagagtg    6900
ctgatttttt gagtaaactt gcaacagtcc taacattctt ctctcgtgtg tttgtgtctg    6960
ttcgccatcc cgtctccgct cgtcacttat ccttcacttt tcagagggtc cccccgcaga    7020
```

```
tcccggtcac cctcaggtcg ggtcgacaac catggtgagc aagggcgagg agctgttcac    7080
cggggtggtg cccatcctgg tcgagctgga cggcgacgta acggccaca agttcagcgt     7140
gtccggcgag ggcgagggcg atgccaccta cggcaagctg accctgaagt tcatctgcac    7200
caccggcaag ctgcccgtgc cctggcccac cctcgtgacc accctgacct acggcgtgca    7260
gtgcttcagc cgctaccccg accacatgaa gcagcacgac ttcttcaagt ccgccatgcc    7320
cgaaggctac gtccaggagc gcaccatctt cttcaaggac gacggcaact acaagacccg    7380
cgccgaggtg aagttcgagg gcgacaccct ggtgaaccgc atcgagctga agggcatcga    7440
cttcaaggag gacggcaaca tcctggggca caagctggag tacaactaca acagccacaa    7500
cgtctatatc atggccgaca gcagaagaa cggcatcaag gtgaacttca agatccgcca     7560
caacatcgag gacggcagcg tgcagctcgc cgaccactac cagcagaaca cccccatcgg    7620
cgacggcccc gtgctgctgc ccgacaacca ctacctgagc acccagtccg ccctgagcaa    7680
agaccccaac gagaagcgcg atcacatggt cctgctggag ttcgtgaccg ccgccgggat    7740
cactctcggc atggacgagc tgtacaagta aagcggcctc gacaatcaac ctctggatta    7800
caaaatttgt gaaagattga ctggtattct taactatgtt gctccttta cgctatgtgg      7860
atacgctgct ttaatgcctt tgtatcatgc tattgcttcc cgtatggctt tcattttctc    7920
ctccttgtat aaatcctggt tgctgtctct ttatgaggag ttgtggcccg ttgtcaggca    7980
acgtggcgtg gtgtgcactg tgtttgctga cgcaaccccc actggttggg gcattgccac    8040
cacctgtcag ctcctttccg ggactttcgc tttccccctc cctattgcca cggcggaact    8100
catcgccgcc tgccttgccc gctgctggac aggggctcgg ctgttgggca ctgacaattc    8160
cgtggtgttg tcggggaagc tgacgtcctt ccatggctg ctcgcctgtg ttgccacctg     8220
gattctgcgc gggacgtcct tctgctacgt cccttcggcc ctcaatccag cggaccttcc    8280
ttcccgcggc ctgctgccgg ctctgcggcc tcttccgcgt cttcgccttc gccctcagac    8340
gagtcggatc tccctttggg ccgcctcccc gcctggaatt cgagctcggt acctttaaga    8400
ccaatgactt acaaggcagc tgtagatctt agccactttt taaagaaaaa gggggactg     8460
gaagggctaa ttcactccca acgaagacaa gatctgcttt ttgcttgtac tgggtctctc    8520
tggttagacc agatctgagc ctgggagctc tctggctaac tagggaaccc actgcttaag    8580
cctcaataaa gcttgccttg agtgcttcaa gtagtgtgtg cccgtctgtt gtgtgactct    8640
ggtaactaga gatccctcag acccttttag tcagtgtgga aaatctctag cagtagtagt    8700
tcatgtcatc ttattattca gtatttataa cttgcaaaga aatgaatatc agagagtgag    8760
aggaacttgt ttattgcagc ttataatggt tacaaataaa gcaatagcat cacaaatttc    8820
acaaataaag cattttttc actgcattct agttgtggtt tgtccaaact catcaatgta     8880
tcttatcatg tctggctcta gctatcccgc cctaactcc gcccagttcc gcccattctc      8940
cgccccatgg ctgactaatt ttttttattt atgcagaggc cgaggccgcc tcggcctctg    9000
agctattcca gaagtagtga ggaggctttt ttggaggcct aggcttttgc gtcgagacgt    9060
acccaattcg ccctatagtg agtcgtatta cgcgcgctca ctggccgtcg ttttacaacg    9120
tcgtgactgg gaaaccctg gcgttaccca acttaatcgc cttgcagcac atccccctttt    9180
cgccagctgg cgtaatagcg aagaggcccg caccgatcgc ccttcccaac agttgcgcag    9240
cctgaatggc gaatgcgcg acgcgccctg tagcggcgca ttaagcgcgg cgggtgtggt     9300
ggttacgcgc agcgtgaccg ctacacttgc cagcgcccta gcgcccgctc ctttcgcttt    9360
cttcccttcc tttctcgcca cgttcgccgg ctttccccgt caagctctaa atcggggct      9420
```

```
ccctttaggg ttccgattta gtgctttacg gcacctcgac cccaaaaaac ttgattaggg    9480
tgatggttca cgtagtgggc catcgccctg atagacggtt tttcgccctt tgacgttgga    9540
gtccacgttc tttaatagtg gactcttgtt ccaaactgga acaacactca accctatctc    9600
ggtctattct tttgatttat aagggatttt gccgatttcg gcctattggt taaaaaatga    9660
gctgatttaa caaaaattta acgcgaattt taacaaaata ttaacgttta caatttcc      9718
```

<210> SEQ ID NO 7
<211> LENGTH: 9490
<212> TYPE: DNA
<213> ORGANISM: Artificial Sequence
<220> FEATURE:
<223> OTHER INFORMATION: plasmid
<220> FEATURE:
<221> NAME/KEY: misc_feature
<222> LOCATION: (1)..(9490)
<223> OTHER INFORMATION:
<220> FEATURE:
<221> NAME/KEY: misc_feature
<222> LOCATION: (1)..(9490)
<223> OTHER INFORMATION: plasmid containing the lentiviral vector
    construct CCL-MA3-GFP/de ltaLNGFR

<400> SEQUENCE: 7

```
caggtggcac ttttcgggga aatgtgcgcg gaaccgctat ttgtttattt ttctaaatac      60
attcaaatat gtatccgctc atgagacaat aaccctgata aatgcttcaa taatattgaa     120
aaaggaagag tatgagtatt caacatttcc gtgtcgccct tattcccttt tttgcggcat     180
tttgccttcc tgtttttgct cacccagaaa cgctggtgaa agtaaaagat gctgaagatc     240
agttgggtgc acgagtgggt tacatcgaac tggatctcaa cagcggtaag atccttgaga     300
gttttcgccc cgaagaacgt tttccaatga tgagcacttt taaagttctg ctatgtggcg     360
cggtattatc ccgtattgac gccgggcaag agcaactcgg tcgccgcata cactattctc     420
agaatgactt ggttgagtac tcaccagtca cagaaaagca tcttacggat ggcatgacag     480
taagagaatt atgcagtgct gccataacca tgagtgataa cactgcggcc aacttacttc     540
tgacaacgat cggaggaccg aaggagctaa ccgcttttt gcacaacatg ggggatcatg      600
taactcgcct tgatcgttgg gaaccggagc tgaatgaagc cataccaaac gacgagcgtg     660
acaccacgat gcctgtagca atggcaacaa cgttgcgcaa actattaact ggcgaactac     720
ttactctagc ttcccggcaa caattaatag actggatgga ggcggataaa gttgcaggac     780
cacttctgcg ctcggccctt ccggctggct ggtttattgc tgataaatct ggagccggtg     840
agcgtgggtc tcgcggtatc attgcagcac tggggccaga tggtaagccc tcccgtatcg     900
tagttatcta cacgacgggg agtcaggcaa ctatggatga acgaaataga cagatcgctg     960
agataggtgc ctcactgatt aagcattggt aactgtcaga ccaagtttac tcatatatac    1020
tttagattga tttaaaactt cattttaat ttaaaaggat ctaggtgaag atcctttttg      1080
ataatctcat gaccaaaatc ccttaacgtg agttttcgtt ccactgagcg tcagaccccg    1140
tagaaaagat caaaggatct tcttgagatc ctttttttct gcgcgtaatc tgctgcttgc    1200
aaacaaaaaa accaccgcta ccagcggtgg tttgtttgcc ggatcaagag ctaccaactc    1260
tttttccgaa ggtaactggc ttcagcagag cgcagatacc aaatactgtc cttctagtgt    1320
agccgtagtt aggccaccac ttcaagaact ctgtagcacc gcctacatac ctcgctctgc    1380
taatcctgtt accagtggct gctgccagtg gcgataagtc gtgtcttacc gggttggact    1440
caagacgata gttaccggat aaggcgcagc ggtcgggctg aacggggggt tcgtgcacac    1500
```

```
agcccagctt ggagcgaacg acctacaccg aactgagata cctacagcgt gagctatgag     1560
aaagcgccac gcttcccgaa gggagaaagg cggacaggta tccggtaagc ggcagggtcg     1620
gaacaggaga gcgcacgagg gagcttccag ggggaaacgc ctggtatctt tatagtcctg     1680
tcgggtttcg ccacctctga cttgagcgtc gattttttgtg atgctcgtca ggggggcgga    1740
gcctatggaa aaacgccagc aacgcggcct ttttacggtt cctggccttt gctggccttt    1800
ttgctcacat gttctttcct gcgttatccc ctgattctgt ggataaccgt attaccgcct    1860
ttgagtgagc tgataccgct cgccgcagcc gaacgaccga gcgcagcgag tcagtgagcg    1920
aggaagcgga gagcgcccca atacgcaaac cgcctctccc cgcgcgttgg ccgattcatt    1980
aatgcagctg gcacgacagg tttcccgact ggaaagcggg cagtgagcgc aacgcaatta    2040
atgtgagtta gctcactcat taggcacccc aggctttaca ctttatgctt ccggctcgta    2100
tgttgtgtgg aattgtgagc ggataacaat ttcacacagg aaacagctat gaccatgatt    2160
acgccaagcg cgcaattaac cctcactaaa gggaacaaaa gctggagctg caagcttggc    2220
cattgcatac gttgtatcca tatcataata tgtacattta tattggctca tgtccaacat    2280
taccgccatg ttgacattga ttattgacta gttattaata gtaatcaatt acggggtcat    2340
tagttcatag cccatatatg gagttccgcg ttacataact tacggtaaat ggcccgcctg    2400
gctgaccgcc caacgacccc cgcccattga cgtcaataat gacgtatgtt cccatagtaa    2460
cgccaatagg gactttccat tgacgtcaat gggtggagta tttacggtaa actgcccact    2520
tggcagtaca tcaagtgtat catatgccaa gtacgccccc tattgacgtc aatgacggta    2580
aatggcccgc ctggcattat gcccagtaca tgaccttatg gactttcct acttggcagt     2640 acatctacgt attagtcatc gctattacca tggtgatgcg gttttggcag tacatcaatg    2700
ggcgtggata gcggtttgac tcacggggat ttccaagtct ccaccccatt gacgtcaatg    2760
ggagtttgtt ttggcaccaa aatcaacggg actttccaaa atgtcgtaac aactccgccc    2820
cattgacgca aatgggcggt aggcgtgtac ggtgggaggt ctatataagc agagctcgtt    2880
tagtgaaccg ggtctctct ggttagacca gatctgagcc tgggagctct ctggctaact    2940
agggaaccca ctgcttaagc ctcaataaag cttgccttga gtgcttcaag tagtgtgtgc    3000
ccgtctgttg tgtgactctg gtaactagag atccctcaga cccttttagt cagtgtggaa    3060
aatctctagc agtggcgccc gaacaggac ctgaaagcga aagggaaacc agagctctct     3120
cgacgcagga ctcggcttgc tgaagcgcgc acggcaagag gcgaggggcg gcgactggtg    3180
agtacgccaa aaattttgac tagcggaggc tagaaggaga gagatgggtg cgagagcgtc    3240
agtattaagc gggggagaat tagatcgcga tgggaaaaaa ttcggttaag gccaggggga    3300
aagaaaaaat ataaattaaa acatatagta tgggcaagca gggagctaga acgattcgca    3360
gttaatcctg gcctgttaga acatcagaa ggctgtagac aaatactggg acagctacaa     3420
ccatcccttc agacaggatc agaagaactt agatcattat ataatacagt agcaaccctc    3480
tattgtgtgc atcaaaggat agagataaaa gacaccaagg aagctttaga caagatagag    3540
gaagagcaaa acaaaagtaa gaccaccgca cagcaagcgg ccgctgatct tcagacctgg    3600
aggaggagat atgagggaca attggagaag tgaattatat aaatataaag tagtaaaaat    3660
tgaaccatta ggagtagcac ccaccaaggc aaagagaaga gtggtgcaga gagaaaaaag    3720
agcagtggga ataggagctt tgttccttgg gttcttggga gcagcaggaa gcactatggg    3780
cgcagcctca atgacgctga cggtacaggc cagacaatta ttgtctggta tagtgcagca    3840
gcagaacaat ttgctgaggg ctattgaggc gcaacagcat ctgttgcaac tcacagtctg    3900
```

```
gggcatcaag cagctccagg caagaatcct ggctgtggaa agatacctaa aggatcaaca    3960
gctcctgggg atttggggtt gctctggaaa actcatttgc accactgctg tgccttggaa    4020
tgctagttgg agtaataaat ctctggaaca gatttggaat cacacgacct ggatggagtg    4080
ggacagagaa attaacaatt acacaagctt aatacactcc ttaattgaag aatcgcaaaa    4140
ccagcaagaa aagaatgaac aagaattatt ggaattagat aaatgggcaa gtttgtggaa    4200
ttggtttaac ataacaaatt ggctgtggta tataaaatta ttcataatga tagtaggagg    4260
cttggtaggt ttaagaatag tttttgctgt actttctata gtgaatagag ttaggcaggg    4320
atattcacca ttatcgtttc agacccacct cccaaccccg aggggacccg acaggcccga    4380
aggaatagaa gaagaaggtg gagagagaga cagagacaga tccattcgat tagtgaacgg    4440
atctcgacgg tatcggttaa cttttaaaag aaaaggggga attgggggt acagtgcagg    4500 ggaaagaata gtagacataa tagcaacaga catacaaact aaagaattac aaaaacaaat    4560
tacaaaaatt caaaatttta tcgatcacga gactagcctc gaggagatct gatcataatc    4620
agccatacca catttgtaga ggttttactt gctttaaaaa acctcccaca cctcccctg    4680 aacctgaaac ataaaatgaa tgcaattgtt gttgttaact tgtttattgc agcttataat    4740
ggttacaaat aaggcaatag catcacaaat ttcacaaata aggcattttt ttcactgcat    4800
tctagttttg gtttgtccaa actcatcaat gtatcttatc atgtctggat ctcaaatccc    4860
tcggaagctg cgcctgtctt aggttggagt gatacatttt tatcactttt acccgtcttt    4920
ggattaggca gtagctctga cggccctcct gtcttaggtt agtgaaaaat gtcactctct    4980
tacccgtcat tggctgtcca gcttagctcg caggggaggt ggtctggatc caccatgtct    5040
agagaatagg aacttcggaa taggaacttc gcggccgctt tacttgtaca gctcgtccat    5100
gccgagagtg atcccggcgg cggtcacgaa ctccagcagg accatgtgat cgcgcttctc    5160 gttgggtct ttgctcaggg cggactgggt gctcaggtag tggttgtcgg gcagcagcac    5220
ggggccgtcg ccgatggggg tgttctgctg gtagtggtcg gcgagctgca cgctgccgtc    5280
ctcgatgttg tggcggatct tgaagttcac cttgatgccg ttcttctgct tgtcggccat    5340
gatatagacg ttgtggctgt tgtagttgta ctccagcttg tgccccagga tgttgccgtc    5400
ctccttgaag tcgatgccct tcagctcgat gcggttcacc agggtgtcgc cctcgaactt    5460
cacctcggcg cgggtcttgt agttgccgtc gtccttgaag aagatggtgc gctcctggac    5520
gtagccttcg ggcatggcgg acttgaagaa gtcgtgctgc ttcatgtggt cggggtagcg    5580
gctgaagcac tgcacgccgt aggtcagggt ggtcacgagg gtgggccagg gcacgggcag    5640
cttgccggtg gtgcagatga acttcagggt cagcttgccg taggtggcat cgccctcgcc    5700
ctcgccggac acgctgaact tgtggccgtt tacgtcgccg tccagctcga ccaggatggg    5760
caccaccccg gtgaacagct cctcgccctt gctcaccatg gttgtcgacc cgacctgagg    5820
gtgaccggga tctgcggggg gaccctctga aaagtgaagg ataagtgacg agcggagacg    5880
ggatggcgaa cagacacaaa cacgcgagag aagaatgtta ggactgttgc aagtttactc    5940
aaaaaatcag cactctttta tattatggtt tacataagca tttacataag acttggatag    6000
attccaaaag aacataggca agcttgatat cgaattccca cggggttggg gttgcgcctt    6060
ttccaaggca gccctgggtt tgcgcaggga cgcggctgct ctgggcgtgg ttccgggaaa    6120
cgcagcggcg ccgaccctgg gtctcgcaca ttcttcacgt ccgttcgcag cgtcacccgg    6180
atcttcgccg ctaccttgt gggcccccg gcgacgcttc ctgctccgcc ctaagtcgg    6240 gaaggttcct tgcggttcgc ggcgtgccgg acgtgacaaa cggaagccgc acgtctcact    6300
```

```
agtaccctcg cagacggaca gcgccaggga gcaatggcag cgcgccgacc gcgatgggct   6360
gtggccaata gcggctgctc agcggggcgc gccgagagca gcggccggga aggggcggtg   6420
cgggaggcgg ggtgtggggc ggtagtgtgg gccctgttcc tgcccgcgcg gtgttccgca   6480
ttctgcaagc ctccggagcg cacgtcggca gtcggctccc tcgttgaccg aatcaccgac   6540
ctctctcccc aggggatcc cccgggctgc aggaattcgg gccgcggcca gctccggcgg   6600 gcagggggg cgctgagcg cagcgcagcg cagccccatc agtccgcaaa gcggaccgag   6660
ctggaagtcg agcgctgccg cgggaggcgg gcgatggggg caggtgccac cggccgcgcc   6720
atggacgggc cgcgcctgct gctgttgctg cttctggggg tgtcccttgg aggtgccaag   6780
gaggcatgcc ccacaggcct gtacacacac agcggtgagt gctgcaaagc ctgcaacctg   6840
ggcgagggtg tggcccagcc ttgtggagcc aaccagaccg tgtgtgagcc ctgcctggac   6900
agcgtgacgt tctccgacgt ggtgagcgcg accgagccgt gcaagccgtg caccgagtgc   6960
gtggggctcc agagcatgtc ggcgccgtgc gtggaggccg acgacgccgt gtgccgctgc   7020
gcctacggct actaccagga tgagacgact gggcgctgcg aggcgtgccg cgtgtgcgag   7080
gcgggctcgg gcctcgtgtt ctcctgccag gacaagcaga acaccgtgtg cgaggagtgc   7140
cccgacggca cgtattccga cgaggccaac cacgtggacc cgtgcctgcc ctgcaccgtg   7200
tgcgaggaca ccgagcgcca gctccgcgag tgcacacgct gggccgacgc cgagtgcgag   7260
gagatccctg gccgttggat tacacggtcc acaccccag agggctcgga cagcacagcc   7320
cccagcaccc aggagcctga ggcacctcca gaacaagacc tcatagccag cacggtggca   7380
ggtgtggtga ccacagtgat gggcagctcc cagcccgtgg tgacccgagg caccaccgac   7440
aacctcatcc ctgtctattg ctccatcctg gctgctgtgg ttgtgggcct tgtggcctac   7500
atagccttca gaggtggaa caggggggatc ctctagagtc gagtctagag tcgacaatca   7560
acctctggat tacaaaattt gtgaaagatt gactggtatt cttaactatg ttgctccttt   7620
tacgctatgt ggatacgctg ctttaatgcc tttgtatcat gctattgctt cccgtatggc   7680 tttcatttc tcctccttgt ataaatcctg gttgctgtct ctttatgagg agttgtggcc   7740
cgttgtcagg caacgtggcg tggtgtgcac tgtgtttgct gacgcaaccc ccactggttg   7800
gggcattgcc accacctgtc agctcctttc cgggactttc gctttccccc tccctattgc   7860
cacggcggaa ctcatcgccg cctgccttgc ccgctgctgg acaggggctc ggctgttggg   7920
cactgacaat tccgtggtgt tgtcggggaa gctgacgtcc tttccatggc tgctcgcctg   7980
tgttgccacc tggattctgc gcgggacgtc cttctgctac gtcccttcgg ccctcaatcc   8040
agcggacctt ccttcccgcg gcctgctgcc ggctctgcgg cctcttccgc gtcttcgcct   8100
tcgccctcag acgagtcgga tctccctttg ggccgcctcc ccgcctggaa ttcgagctcg   8160
gtacctttaa gaccaatgac ttacaaggca gctgtagatc ttagccactt tttaaagaa   8220 aagggggac tggaagggct aattcactcc caacgaagac aagatctgct ttttgcttgt   8280
actgggtctc tctggttaga ccagatctga gcctgggagc tctctggcta actagggaac   8340
ccactgctta agcctcaata aagcttgcct tgagtgcttc aagtagtgtg tgcccgtctg   8400
ttgtgtgact ctggtaacta gagatccctc agaccctttt agtcagtgtg gaaaatctct   8460
agcagtagta gttcatgtca tcttattatt cagtatttat aacttgcaaa gaatgaata   8520 tcagagagtg agaggaactt gtttattgca gcttataatg gttacaaata aagcaatagc   8580
atcacaaatt tcacaaataa agcattttt tcactgcatt ctagttgtgg tttgtccaaa   8640
ctcatcaatg tatcttatca tgtctggctc tagctatccc gcccctaact ccgcccagtt   8700
```

-continued

```
ccgcccattc tccgcccat ggctgactaa ttttttttat ttatgcagag gccgaggccg    8760
cctcggcctc tgagctattc cagaagtagt gaggaggctt ttttggaggc ctaggctttt    8820
gcgtcgagac gtacccaatt cgccctatag tgagtcgtat tacgcgcgct cactggccgt    8880
cgttttacaa cgtcgtgact gggaaaaccc tggcgttacc caacttaatc gccttgcagc    8940
acatccccct ttcgccagct ggcgtaatag cgaagaggcc cgcaccgatc gcccttccca    9000
acagttgcgc agcctgaatg gcgaatggcg cgacgcgccc tgtagcggcg cattaagcgc    9060
ggcgggtgtg gtggttacgc gcagcgtgac cgctacactt gccagcgccc tagcgcccgc    9120
tcctttcgct ttcttccctt cctttctcgc cacgttcgcc ggctttcccc gtcaagctct    9180
aaatcggggg ctccctttag ggttccgatt tagtgcttta cggcacctcg accccaaaaa    9240
acttgattag ggtgatggtt cacgtagtgg gccatcgccc tgatagacgg ttttcgccc     9300 tttgacgttg gagtccacgt tctttaatag tggactcttg ttccaaactg gaacaacact    9360 caacccctatc tcggtctatt cttttgattt ataagggatt tgccgatttt cggcctattg    9420
gttaaaaaat gagctgattt aacaaaaatt taacgcgaat tttaacaaaa tattaacgtt    9480
tacaatttcc                                                           9490
```

<210> SEQ ID NO 8
<211> LENGTH: 10086
<212> TYPE: DNA
<213> ORGANISM: Artificial Sequence
<220> FEATURE:
<223> OTHER INFORMATION: plasmid
<220> FEATURE:
<221> NAME/KEY: misc_feature
<222> LOCATION: (1)..(10086)
<223> OTHER INFORMATION:
<220> FEATURE:
<221> NAME/KEY: misc_feature
<222> LOCATION: (1)..(10086)
<223> OTHER INFORMATION: plasmid containing the lentiviral vector
      construct CCL-MA4-GFP/de ltaLNGFR

<400> SEQUENCE: 8

```
caggtggcac ttttcgggga aatgtgcgcg gaacccctat ttgtttattt ttctaaatac      60
attcaaatat gtatccgctc atgagacaat aaccctgata aatgcttcaa taatattgaa     120
aaaggaagag tatgagtatt caacatttcc gtgtcgccct tattcccttt tttgcggcat     180
tttgccttcc tgttttgct cacccagaaa cgctggtgaa agtaaaagat gctgaagatc      240
agttgggtgc acgagtgggt tacatcgaac tggatctcaa cagcggtaag atccttgaga     300
gttttcgccc cgaagaacgt tttccaatga tgagcacttt taaagttctg ctatgtggcg     360
cggtattatc ccgtattgac gccgggcaag agcaactcgg tcgccgcata cactattctc     420
agaatgactt ggttgagtac tcaccagtca cagaaaagca tcttacggat ggcatgacag     480
taagagaatt atgcagtgct gccataacca tgagtgataa cactgcggcc aacttacttc     540
tgacaacgat cggaggaccg aaggagctaa ccgcttttt gcacaacatg ggggatcatg      600
taactcgcct tgatcgttgg gaaccggagc tgaatgaagc cataccaaac gacgagcgtg     660
acaccacgat gcctgtagca atggcaacaa cgttgcgcaa actattaact ggcgaactac     720
ttactctagc ttcccggcaa caattaatag actggatgga ggcggataaa gttgcaggac     780
cacttctgcg ctcggccctt ccggctggct ggtttattgc tgataaatct ggagccggtg     840
agcgtgggtc tcgcggtatc attgcagcac tggggccaga tggtaagccc tcccgtatcg     900
tagttatcta cacgacgggg agtcaggcaa ctatggatga acgaaataga cagatcgctg     960
agataggtgc ctcactgatt aagcattggt aactgtcaga ccaagtttac tcatatatac    1020
```

```
tttagattga tttaaaactt cattttaat ttaaaaggat ctaggtgaag atccttttg    1080 ataatctcat gaccaaaatc ccttaacgtg agttttcgtt ccactgagcg tcagaccccg  1140
tagaaaagat caaaggatct tcttgagatc ctttttttct gcgcgtaatc tgctgcttgc  1200
aaacaaaaaa accaccgcta ccagcggtgg tttgtttgcc ggatcaagag ctaccaactc  1260
tttttccgaa ggtaactggc ttcagcagag cgcagatacc aaatactgtc cttctagtgt  1320
agccgtagtt aggccaccac ttcaagaact ctgtagcacc gcctacatac ctcgctctgc  1380
taatcctgtt accagtggct gctgccagtg gcgataagtc gtgtcttacc gggttggact  1440
caagacgata gttaccggat aaggcgcagc ggtcgggctg aacggggggt tcgtgcacac  1500
agcccagctt ggagcgaacg acctacaccg aactgagata cctacagcgt gagctatgag  1560
aaagcgccac gcttcccgaa gggagaaagg cggacaggta tccggtaagc ggcagggtcg  1620
gaacaggaga gcgcacgagg gagcttccag ggggaaacgc ctggtatctt tatagtcctg  1680
tcgggtttcg ccacctctga cttgagcgtc gatttttgtg atgctcgtca ggggggcgga  1740
gcctatggaa aaacgccagc aacgcggcct ttttacggtt cctggccttt tgctggcctt  1800
ttgctcacat gttctttcct gcgttatccc ctgattctgt ggataaccgt attaccgcct  1860
ttgagtgagc tgataccgct cgccgcagcc gaacgaccga gcgcagcgag tcagtgagcg  1920
aggaagcgga gagcgccca atacgcaaac cgcctctccc cgcgcgttgg ccgattcatt  1980
aatgcagctg gcacgacagg tttcccgact ggaaagcggg cagtgagcgc aacgcaatta  2040
atgtgagtta gctcactcat taggcacccc aggctttaca ctttatgctt ccggctcgta  2100
tgttgtgtgg aattgtgagc ggataacaat ttcacacagg aaacagctat gaccatgatt  2160
acgccaagcg cgcaattaac cctcactaaa gggaacaaaa gctggagctg caagcttggc  2220
cattgcatac gttgtatcca tatcataata tgtacattta tattggctca tgtccaacat  2280
taccgccatg ttgacattga ttattgacta gttattaata gtaatcaatt acggggtcat  2340
tagttcatag cccatatatg gagttccgcg ttacataact tacggtaaat ggcccgcctg  2400
gctgaccgcc caacgacccc cgcccattga cgtcaataat gacgtatgtt cccatagtaa  2460
cgccaatagg gactttccat tgacgtcaat gggtggagta tttacggtaa actgcccact  2520
tggcagtaca tcaagtgtat catatgccaa gtacgccccc tattgacgtc aatgacggta  2580
aatggcccgc ctggcattat gcccagtaca tgaccttatg gactttcct acttggcagt   2640 acatctacgt attagtcatc gctattacca tggtgatgcg gttttggcag tacatcaatg  2700
ggcgtggata gcggtttgac tcacggggat ttccaagtct ccaccccatt gacgtcaatg  2760
ggagtttgtt ttggcaccaa aatcaacggg actttccaaa atgtcgtaac aactccgccc  2820
cattgacgca aatgggcggt aggcgtgtac ggtgggaggt ctatataagc agagctcgtt  2880
tagtgaaccg ggtctctct ggttagacca gatctgagcc tgggagctct ctggctaact   2940
agggaaccca ctgcttaagc ctcaataaag cttgccttga gtgcttcaag tagtgtgtgc  3000
ccgtctgttg tgtgactctg gtaactagag atccctcaga cccttttagt cagtgtggaa  3060
aatctctagc agtggcgccc gaacagggac ctgaaagcga agggaaacc agagctctct   3120 cgacgcagga ctcggcttgc tgaagcgcgc acggcaagag gcgaggggcg gcgactggtg  3180
agtacgccaa aaattttgac tagcggaggc tagaaggaga gagatgggtg cgagagcgtc  3240
agtattaagc gggggagaat tagatcgcga tgggaaaaaa ttcggttaag gccaggggga  3300
aagaaaaaat ataaattaaa acatatagta tgggcaagca gggagctaga acgattcgca  3360
gttaatcctg gcctgttaga acatcagaa ggctgtagac aaatactggg acagctacaa   3420
```

```
ccatcccttc agacaggatc agaagaactt agatcattat ataatacagt agcaaccctc    3480
tattgtgtgc atcaaaggat agagataaaa gacaccaagg aagctttaga caagatagag    3540
gaagagcaaa acaaaagtaa gaccaccgca cagcaagcgg ccgctgatct tcagacctgg    3600
aggaggagat atgagggaca attggagaag tgaattatat aaatataaag tagtaaaaat    3660
tgaaccatta ggagtagcac ccaccaaggc aaagagaaga gtggtgcaga gagaaaaaag    3720
agcagtggga ataggagctt tgttccttgg gttcttggga gcagcaggaa gcactatggg    3780
cgcagcctca atgacgctga cggtacaggc cagacaatta ttgtctggta tagtgcagca    3840
gcagaacaat ttgctgaggg ctattgaggc gcaacagcat ctgttgcaac tcacagtctg    3900
gggcatcaag cagctccagg caagaatcct ggctgtggaa agatacctaa aggatcaaca    3960
gctcctgggg atttggggtt gctctggaaa actcatttgc accactgctg tgccttggaa    4020
tgctagttgg agtaataaat ctctggaaca gattggaatc acacgacctg gatggagtgg    4080
gacagagaaa ttaacaatta cacaagctta atacactcct taattgaaga tcgcaaaac    4140 cagcaagaaa agaatgaaca agaattattg gaattagata aatgggcaag tttgtggaat    4200
tggtttaaca taacaaattg gctgtggtat ataaaattat tcataatgat agtaggaggc    4260
ttggtaggtt taagaatagt ttttgctgta ctttctatag tgaatagagt taggcaggga    4320
tattcaccat tatcgtttca gacccacctc ccaaccccga ggggacccga caggcccgaa    4380
ggaatagaag aagaaggtgg agagagagac agagacagat ccattcgatt agtgaacgga    4440
tctcgacggt atcggttaac ttttaaaaga aagggggga ttgggggggta cagtgcaggg    4500 gaaagaatag tagacataat agcaacagac atacaaacta agaattaca aaaacaaatt    4560 acaaaaattc aaaattttat cgatcacgag actagcctcg agagatctga tcataatcag    4620
ccataccaca tttgtagagg ttttacttgc tttaaaaaac ctcccacacc tccccctgaa    4680
cctgaaacat aaaatgaatg caattgttgt tgttaacttg tttattgcag cttataatgg    4740
ttacaaataa ggcaatagca tcacaaattt cacaaataag gcatttttt cactgcattc    4800 tagttttggt ttgtccaaac tcatcaatgt atcttatcat gtctggatct caaatccctc    4860
ggaagctgcg cctgtcttag gttggagtga tacattttta tcactttac ccgtctttgg    4920 attaggcagt agctctgacg gccctcctgt cttaggttag tgaaaaatgt cactctctta    4980
cccgtcattg gctgtccagc ttagctcgca ggggaggtgg tctggatccg agctcgaatt    5040
ggccgcttta cttgtacagc tcgtccatgc cgagagtgat cccggcggcg gtcacgaact    5100
ccagcaggac catgtgatcg cgcttctcgt tgggtctttt gctcagggcg gactgggtgc    5160
tcaggtagtg gttgtcgggc agcagcacgg ggccgtcgcc gatgggggtg ttctgctggt    5220
agtggtcggc gagctgcacg ctgccgtcct cgatgttgtg gcggatcttg aagttcacct    5280
tgatgccgtt cttctgcttg tcggccatga tatagacgtt gtggctgttg tagttgtact    5340
ccagcttgtg ccccaggatg ttgccgtcct ccttgaagtc gatgcccttc agctcgatgc    5400
ggttcaccag ggtgtcgccc tcgaacttca cctcggcgcg ggtcttgtag ttgccgtcgt    5460
ccttgaagaa gatggtgcgc tcctggacgt agccttcggg catggcggac ttgaagaagt    5520
cgtgctgctt catgtggtcg gggtagcggc tgaagcactg cacgccgtag gtcagggtgg    5580
tcacgagggt gggccagggc acgggcagct tgccggtggt gcagatgaac ttcagggtca    5640
gcttgccgta ggtggcatcg ccctcgccct cgccggacac gctgaacttg tggccgttta    5700
cgtcgccgtc cagctcgacc aggatgggca ccaccccgt gaacagctcc tcgcccttgc    5760
tcaccatggt gaattccgcg gaggctggat cggtcccggt gtcttctatg gaggtcaaaa    5820
```

```
cagcgtggat ggcgtctcca ggcgatctga cggttcacta aacgagctct gcttatatag    5880
gcctcccacc gtacacgcct accctcgaga agcttgatta cccgtgtcg gctccagatc     5940 tggcctccgc gccgggtttt ggcgcctccc gcgggcgccc ccctcctcac ggcgagcgct    6000
gccacgtcag acgaagggcg cagcgagcgt cctgatcctt ccgcccggac gctcaggaca    6060
gcggcccgct gctcataaga ctcggcctta aaccccagt atcagcagaa ggacatttta    6120
ggacgggact tgggtgactc tagggcactg gttttctttc cagagagcgg aacaggcgag    6180
gaaaagtagt cccttctcgg cgattctgcg gagggatctc cgtggggcgg tgaacgccga    6240
tgattatata aggacgcgcc gggtgtggca cagctagttc cgtcgcagcc gggatttggg    6300
tcgcggttct tgtttgtgga tcgctgtgat cgtcacttgg tgagttgcgg gctgctgggc    6360
tggccggggc tttcgtggcc gccgggccgc tcggtgggac ggaagcgtgt ggagagaccg    6420
ccaagggctg tagtctgggt ccgcgagcaa ggttgccctg aactgggggt tgggggagc     6480 gcacaaaatg gcggctgttc ccgagtcttg aatggaagac gcttgtaagg cgggctgtga    6540
ggtcgttgaa acaaggtggg gggcatggtg ggcggcaaga acccaaggtc ttgaggcctt    6600
cgctaatgcg ggaaagctct tattcgggtg agatgggctg gggcaccatc tggggaccct    6660
gacgtgaagt ttgtcactga ctggagaact cgggtttgtc gtctggttgc ggggcggca    6720 gttatgcggt gccgttgggc agtgcacccg tacctttggg agcgcgcgcc tcgtcgtgtc    6780
gtgacgtcac ccgttctgtt ggcttataat gcagggtggg gccacctgcc ggtaggtgtg    6840
cggtaggctt ttctccgtcg caggacgcag ggttcgggcc tagggtaggc tctcctgaat    6900
cgacaggcgc cggacctctg gtgaggggag ggataagtga ggcgtcagtt tctttggtcg    6960
gttttatgta cctatcttct taagtagctg aagctccggt tttgaactat gcgctcgggg    7020
ttggcgagtg tgttttgtga agttttttag gcaccttttg aaatgtaatc atttgggtca    7080
atatgtaatt ttcagtgtta gactagtaaa ttgtccgcta aattctgcc gttttttggct    7140 tttttgttag acgaagcttg ggctgcagga attcgggccg cggccagctc cggcgggcag    7200 gggggcgct ggagcgcagc gcagcgcagc cccatcagtc cgcaaagcgg accgagctgg     7260
aagtcgagcg ctgccgcggg aggcgggcga tgggggcagg tgccaccggc cgcgccatgg    7320
acgggccgcg cctgctgctg ttgctgcttc tgggggtgtc ccttggaggt gccaaggagg    7380 catgcccac aggcctgtac acacacagcg gtgagtgctg caaagcctgc aacctgggcg     7440
agggtgtggc ccagccttgt ggagccaacc agaccgtgtg tgagccctgc ctggacagcg    7500
tgacgttctc cgacgtggtg agcgcgaccg agccgtgcaa gccgtgcacc gagtgcgtgg    7560
ggctccagag catgtcggcg ccgtgcgtgg aggccgacga gccgtgtgc cgctgcgcct     7620 acggctacta ccaggatgag acgactgggc gctgcgaggc gtgccgcgtg tgcgaggcgg    7680
gctcgggcct cgtgttctcc tgccaggaca gcagaacac cgtgtgcgag gagtgccccg     7740
acggcacgta ttccgacgag gccaaccacg tggacccgtg cctgccctgc accgtgtgcg    7800
aggacaccga gcgccagctc cgcgagtgca cacgctgggc cgacgccgag tgcgaggaga    7860
tccctggccg ttggattaca cggtccacac ccccagaggg ctcggacagc acagccccca    7920
gcacccagga gcctgaggca cctccagaac aagacctcat agccagcacg gtggcaggtg    7980
tggtgaccac agtgatgggc agctcccagc cgtggtgac ccgaggcacc accgacaacc     8040
tcatccctgt ctattgctcc atcctggctg ctgtggttgt gggccttgtg gcctacatag    8100
ccttcaagag gtgaacagg gggatcctct agagtcgagt ctagagtcga caatcaacct    8160
ctggattaca aaatttgtga agattgact ggtattctta actatgttgc tccttttacg     8220
```

```
ctatgtggat acgctgcttt aatgcctttg tatcatgcta ttgcttcccg tatggctttc    8280
attttctcct ccttgtataa atcctggttg ctgtctcttt atgaggagtt gtggcccgtt    8340
gtcaggcaac gtggcgtggt gtgcactgtg tttgctgacg caaccccac tggttggggc     8400
attgccacca cctgtcagct cctttccggg actttcgctt tcccctccc tattgccacg     8460
gcggaactca tcgccgcctg ccttgcccgc tgctggacag gggctcggct gttgggcact    8520
gacaattccg tggtgttgtc ggggaagctg acgtcctttc catggctgct cgcctgtgtt   8580
gccacctgga ttctgcgcgg gacgtccttc tgctacgtcc cttcggccct caatccagcg   8640
gaccttcctt cccgcggcct gctgccggct ctgcggcctc ttccgcgtct tcgccttcgc   8700
cctcagacga gtcggatctc cctttgggcc gcctccccgc ctggaattcg agctcggtac   8760
ctttaagacc aatgacttac aaggcagctg tagatcttag ccacttttta aaagaaaagg   8820
ggggactgga agggctaatt cactcccaac gaagacaaga tctgcttttt gcttgtactg   8880
ggtctctctg gttagaccag atctgagcct gggagctctc tggctaacta gggaacccac   8940
tgcttaagcc tcaataaagc ttgccttgag tgcttcaagt agtgtgtgcc cgtctgttgt   9000
gtgactctgg taactagaga tccctcagac ccttttagtc agtgtggaaa atctctagca   9060
gtagtagttc atgtcatctt attattcagt atttataact tgcaaagaaa tgaatatcag   9120
agagtgagag gaacttgttt attgcagctt ataatggtta caaataaagc aatagcatca   9180
caaatttcac aaataaagca ttttttttcac tgcattctag ttgtggtttg tccaaactca   9240
tcaatgtatc ttatcatgtc tggctctagc tatcccgccc ctaactccgc ccagttccgc   9300
ccattctccg ccccatggct gactaatttt ttttatttat gcagaggccg aggccgcctc   9360
ggcctctgag ctattccaga agtagtgagg aggcttttt ggaggcctag gcttttgcgt    9420
cgagacgtac ccaattcgcc ctatagtgag tcgtattacg cgcgctcact ggccgtcgtt   9480
ttacaacgtc gtgactggga aaaccctggc gttacccaac ttaatcgcct tgcagcacat   9540
ccccctttcg ccagctggcg taatagcgaa gaggcccgca ccgatcgccc ttcccaacag   9600
ttgcgcagcc tgaatggcga atggcgcgac gcgcctgta gcggcgcatt aagcgcggcg    9660
ggtgtggtgg ttacgcgcag cgtgaccgct acacttgcca gcgccctagc gcccgctcct   9720
ttcgctttct tcccttcctt tctcgccacg ttcgccggct ttccccgtca gctctaaat   9780
cggggctcc ctttagggtt ccgatttagt gctttacggc acctcgaccc caaaaaactt    9840
gattagggtg atggttcacg tagtgggcca tcgccctgat agacggtttt tcgccctttg   9900
acgttggagt ccacgttctt taatagtgga ctcttgttcc aaactggaac aacactcaac   9960
cctatctcgg tctattcttt tgatttataa gggattttgc cgatttcggc ctattggtta  10020
aaaaatgagc tgatttaaca aaaatttaac gcgaatttta acaaaatatt aacgtttaca  10080
atttcc                                                             10086
```